US010864278B2

(12) United States Patent
Kontermann et al.

(10) Patent No.: US 10,864,278 B2
(45) Date of Patent: *Dec. 15, 2020

(54) ANTIBODY-DRUG CONJUGATES AND IMMUNOTOXINS

(71) Applicant: Oncomatryx Biopharma, S.L., Derio (ES)

(72) Inventors: Roland Kontermann, Nurtingen (DE); Klaus Pfizenmaier, Tiefenbronn (DE); Cristina Ferrer, Madrid (ES); Myriam Fabre, Barcelona (ES); Laureano Simon, Derio (ES)

(73) Assignee: Oncomatryx Biopharma, S.L., Derio (ES)

( * ) Notice: Subject to any disclaimer, the term of this patent is extended or adjusted under 35 U.S.C. 154(b) by 154 days.

This patent is subject to a terminal disclaimer.

(21) Appl. No.: 16/162,211

(22) Filed: Oct. 16, 2018

(65) Prior Publication Data

US 2019/0105406 A1    Apr. 11, 2019

Related U.S. Application Data

(63) Continuation of application No. 15/116,430, filed as application No. PCT/EP2015/052341 on Feb. 4, 2015, now Pat. No. 10,137,202.

(30) Foreign Application Priority Data

Feb. 6, 2014 (GB) .................................. 1402006.9

(51) Int. Cl.
| | |
|---|---|
| *A61K 39/00* | (2006.01) |
| *A61K 47/68* | (2017.01) |
| *C07K 16/30* | (2006.01) |
| *C07K 16/40* | (2006.01) |
| *A61K 45/06* | (2006.01) |
| *C12N 9/24* | (2006.01) |

(52) U.S. Cl.
CPC .......... *A61K 47/6871* (2017.08); *A61K 45/06* (2013.01); *A61K 47/6815* (2017.08); *A61K 47/6825* (2017.08); *A61K 47/6829* (2017.08); *A61K 47/6847* (2017.08); *C07K 16/30* (2013.01); *C07K 16/303* (2013.01); *C07K 16/3015* (2013.01); *C07K 16/3023* (2013.01); *C07K 16/3038* (2013.01); *C07K 16/40* (2013.01); *C12N 9/2497* (2013.01); *C12Y 302/02022* (2013.01); *A61K 2039/505* (2013.01); *C07K 2317/24* (2013.01); *C07K 2317/33* (2013.01); *C07K 2317/52* (2013.01); *C07K 2317/565* (2013.01); *C07K 2317/622* (2013.01); *C07K 2317/77* (2013.01); *C07K 2317/92* (2013.01); *C07K 2319/00* (2013.01)

(58) Field of Classification Search
CPC ................................................ A61K 47/6871
See application file for complete search history.

(56) References Cited

U.S. PATENT DOCUMENTS

| 10,137,202 B2 * | 11/2018 | Kontermann .......... C07K 16/40 |
| 2002/0099180 A1 | 7/2002 | Pfizenmaier et al. |
| 2009/0304718 A1 | 12/2009 | Adolf et al. |

FOREIGN PATENT DOCUMENTS

| EP | 0953639 | 11/1999 |
| JP | 2007538099 | 12/2007 |
| JP | 2010521485 | 6/2010 |
| WO | WO 97/45450 | 12/1997 |
| WO | WO 01/68708 | 9/2001 |
| WO | WO 2005/108419 | 11/2005 |
| WO | WO 2005/112919 | 12/2005 |
| WO | WO 2007/014744 | 2/2007 |
| WO | WO 2008/112873 | 9/2008 |
| WO | WO 2008/138561 | 11/2008 |
| WO | WO 2012/020006 | 2/2012 |
| WO | WO 2013/085925 | 6/2013 |
| WO | WO 2013/173393 | 11/2013 |
| WO | WO 2014/009774 | 1/2014 |
| WO | WO 2015/113760 | 8/2015 |

OTHER PUBLICATIONS

George et al. (Circulation. 1998; 97: 900-906), (Year: 1998).*
Acharyya et al. "A CXCL1 paracrine network links cancer chemoresistance and metastasis." *Cell* 150(1): 165-178, 2012.
Barbieri et al. "Purification and conjugation of type 1 ribosome-inactivating proteins." *Methods in Molecular Biology: Immunotoxin Methods and Protocols* 166: 71-85, 2001.
Brocks et al. "Species-crossreactive scFv against the tumor stroma marker "fibroblast activation protein" selected by phage display from an immunized FAP-/-knock-out mouse." *Molecular Medicine* 7(7): 461, 2001.
Brown et al., "Tolerance to Single, but Not Multiple, Amino Acid Replacements in Antibody $v_H$ CDR2," *J. Immunol.*, vol. 156, No. 9, pp. 3285-3291, 1996.
Crawford et al. "PDGF-C mediates the angiogenic and tumorigenic properties fibroblasts associated with tumors refractory to anti-VEGF treatment." *Cancer Cell* 15(1): 21-34, 2001.

(Continued)

*Primary Examiner* — Sheela J. Huff
(74) *Attorney, Agent, or Firm* — Klarquist Sparkman, LLP

(57) ABSTRACT

The present invention relates to conjugates, in particular antibody-drug conjugates and immunotoxins, having the formula I:

A-(L-D)p    (I)

or a pharmaceutically acceptable salts or solvates thereof, wherein:
A is an antibody that selectively binds FAP;
L is a linker;
D is a drug comprising a cytolysin or a Nigrin-b A-chain; and
p is 1 to 10, and to use of such conjugates in the therapeutic treatment of tumors. Methods of producing such conjugates and components for use in such methods are disclosed.

17 Claims, 28 Drawing Sheets

Specification includes a Sequence Listing.

(56) References Cited

OTHER PUBLICATIONS

Erez et al. "Cancer-associated fibroblasts are activated in incipient neoplasia to orchestrate tumor-promoting inflammation in an NF-κB-dependent manner." *Cancer Cell* 17(2): 135-147, 2010.
Fracasso et al. "Immunotoxins and other conjugates: Preparation and general characteristics." *Mini Reviews in Medicinal Chemistry* 4(5): 545-562, 2004.
GenBank Accession No. AZZ32107, Oct. 25, 2012, 1 page.
GenBank Accession No. BAT67876, Nov. 21, 2013, 1 page.
Ghetie & Vitetta. "Chemical construction of immunotoxins." *Molecular Biotechnology* 18(3): 251-268, 2001.
Gualberto. "Brentuximab vedotin (SGN-35), an antibody-drug conjugate for the treatment of CD30-positive malignancies." *Expert Opinion on Investigational Drugs* 21(2): 205-216, 2012.
Gupta et al. "Cancer metastasis: building a framework." *Cell* 127(4): 679-695, 2006.
Hanahan & Coussens. "Accessories to the crime: functions of cells recruited to the tumor microenvironment." *Cancer Cell* 21(3): 309-322, 2012.
Hanahan & Weinberg. "Hallmarks of cancer: the next generation." *Cell* 144(5): 646-674, 2011.
Horimoto et al. "Emerging roles of the tumor-associated stroma in promoting tumor metastasis." *Cell Adhesion & Migration* 6(3): 193-203, 2012.
Hu et al. "Role of COX-2 in epithelial-stromal cell interactions and progression of ductal carcinoma in situ of the breast." *Proc. Nat. Academy of Sci.* 106(9): 3372-3377, 2009.
Hwang et al. "Cancer-associated stromal fibroblasts promote pancreatic tumor progression." *Cancer Research* 68(3): 918-926, 2008.
Joyce & Pollard. "Microenvironmental regulation of metastasis." *Nature Reviews Cancer* 9(4): 239-252, 2009.
Joyce. "Therapeutic targeting of the tumor microenvironment." *Cancer Cell* 7(6): 513-520, 2005.
Kalluri & Zeisberg. "Fibroblasts in cancer." *Nature Reviews Cancer* 6(5): 392-401, 2006.
Kaur et al. "Biological evaluation of tubulysin A: a potential anticancer and antiangiogenic natural product." *Biochemical J* 396(2): 235-242, 2006.
Lambert & Blättler. "Purification and biochemical characterization of immunotoxins." *Immunotoxins*: Chapter 18, pp. 323-348. Kluwer Academic Publishers, Springer US, 1988.
Malanchi et al. "Interactions between cancer stem cells and their niche govern metastatic colonization." *Nature* 481(7379): 85-89, 2012.
Marsh et al. "Antibody-toxin conjugation." *Immunotoxins*: 213-237. Springer US, 1988.
Meads et al. "Environment-mediated drug resistance: a major contributor to minimal residual disease." *Nature Reviews Cancer* 9(9): 665-674, 2009.
Medema et al. "Microenvironmental regulation of stem cells in intestinal homeostasis and cancer." *Nature* 474(7351): 318-326, 2011.
Mersmann et al. "Human antibody derivatives against the fibroblast activation protein for tumor stroma targeting of carcinomas." *International J Cancer* 92(2): 240-248, 2001.
Messerschmidt et al. "Targeted lipid-coated nanoparticles: delivery of tumor necrosis factor-functionalized particles to tumor cells." *J Controlled Release* 137(1): 69-77, 2009.
Muñoz et al. "In vitro and in vivo effects of an anti-mouse endoglin (CD105)—immunotoxin on the early stages of mouse B16MEL4A5 melanoma tumours." *Cancer Immunology, Immunotherapy* 62(3): 541-551, 2013.
Muñoz et al. "Sensitivity of cancer cell lines to the novel non-toxic type 2 ribosome-inactivating protein nigrin b." *Cancer Letters* 167(2): 163-169, 2001.
Muñoz et al. "Targeting a marker of the tumour neovasculature using a novel anti-human CD105-immunotoxin containing the non-toxic type 2 ribosome-inactivating protein nigrin b." *Cancer Letters* 256(1): 73-80, 2007.

Nieman et al. "Adipocytes promote ovarian cancer metastasis and provide energy for rapid tumor growth." *Nature Medicine* 17(11): 1498-1503, 2011.
Olive et al. "Inhibition of Hedgehog signaling enhances delivery of chemotherapy in a mouse model of pancreatic cancer." *Science* 324(5933): 1457-1461, 2009.
Olumi et al. "Carcinoma-associated fibroblasts direct tumor progression of initiated human prostatic epithelium." *Cancer Research* 59(19): 5002-5011, 1999.
Orimo et al. "Stromal fibroblasts present in invasive human breast carcinomas promote tumor growth and angiogenesis through elevated SDF-1/CXCL12 secretion." *Cell* 121(3): 335-348, 2005.
Ostermann et al. "Effective immunoconjugate therapy in cancer models targeting a serine protease of tumor fibroblasts." *Clinical Cancer Research* 14(14): 4584-4592, 2008.
Perez-Soler et al. "Response and determinants of sensitivity to paclitaxel in human non-small cell lung cancer tumors heterotransplanted in nude mice." *Clinical Cancer Research* 6(12): 4932-4938, 2000.
Pietras & Ostman. "Hallmarks of cancer: interactions with the tumor stroma." *Experimental cell research* 316(8): 1324-1331, 2010.
Reddy et al. "In Vivo Structural Activity and Optimization Studies of Folate-Tubulysin Conjugates." *Molecular pharmaceutics* 6(5): 1518-1525, 2009.
Riddles et al. "Ellman's reagent: 5, 5'-dithiobis (2-nitrobenzoic acid)—a reexamination." *Analytical biochemistry* 94(1): 75-81, 1979.
Riener et al. "Quick measurement of protein sulfhydryls with Ellman's reagent and with 4, 4'-dithiodipyridine." *Analytical and Bioanalytical Chemistry* 373(4-5): 266-276, 2002.
Sasse et al. "Tubulysins, new cytostatic peptides from myxobacteria acting on microtubuli. Production, isolation, physico-chemical and biological properties." *The Journal of Antibiotics* 53(9): 879-885, 2009.
Schluep et al. "Polymeric tubulysin-peptide nanoparticles with potent antitumor activity." *Clinical Cancer Research* 15(1): 181-189, 2009.
Schmidt et al. "Generation of human high-affinity antibodies specific for the fibroblast activation protein by guided selection." *European Journal of Biochemistry* 268(6): 1730-1738, 2001.
Shi et al. "Expression of fibroblast activation protein in human pancreatic adenocarcinoma and its clinicopathological significance." *World J Gastroenterol* 18(8): 840-846, 2012.
Straussman et al. "Tumor microenvironment induces innate RAF-inhibitor resistance through HGF secretion." *Nature* 487(7408): 500, 2012.
Strell et al. "Fibroblasts—a key host cell type in tumor initiation, progression, and metastasis." *Upsala J Med Sci* 117(2): 187-195, 2012.
Tejuca et al., "Construction of an immunotoxin with the pore forming protein StI and ior C5, a monoclonal antibody against a colon cancer cell line," *International Immunopharmacology*, vol. 4, No. 6, pp. 731-744, 2004.
Thorpe et al. "New coupling agents for the synthesis of immunotoxins containing a hindered disulfide bond with improved stability in vivo." *Cancer Research* 47(22): 5924-5931, 1987.
Thrush et al. "Immunotoxins: an update." *Annual Review of Immunology* 14(1): 49-71, 1996.
Vajdos et al., "Comprehensive Functional Maps of the Antigen binding Site of an Anti-ErbB2 Antibody Obtained with Shotgun Scanning Mutagenesis," *J. Mol. Biol.*, vol. 320, No. 2, pp. 415-428, 2002.
Valastyan & Weinberg. "Tumor metastasis: molecular insights and evolving paradigms." *Cell* 147(2): 275-292, 2011.
Weinberg. Excerpts from "Dialogue Replaces Monologue: Heterotypic Interactions and the Biology of Angiogenesis." *The Biology of Cancer*: Chapter 13, pp. 527-530, 546, 547, New York: Garland Science, 2007.
Wu et al. "Anti-angiogenic therapeutic drugs for treatment of human cancer." *J Cancer Mol* 4, No. 2 (2008): 37-45.
Yabuuchi et al. "Notch signaling pathway targeted therapy suppresses tumor progression and metastatic spread in pancreatic cancer." *Cancer Letters* 335(1): 41-51, 2013.

(56) References Cited

OTHER PUBLICATIONS

Yang et al. "The chemokine growth-regulated oncogene 1 (Gro-1) links RAS signaling to the senescence of stromal fibroblasts and ovarian tumorigenesis." *Proceedings of the National Academy of Sciences* 103(44): 16472-16477, 2006.

Muñoz et al., "Transient Injury-Dependent Up-Regulation of CD105 and its Specific Targeting with Anti-Vascular Anti-Mouse Endoglin-Nigrin b Immunotoxin," *Medicinal Chemistry*, vol. 8, pp. 996-1002, 2012.

Tejuca et al., "Sea anemone cytolysins as toxic components of immunotoxins," *Toxicon*, vol. 54, pp. 1206-1214, 2009.

\* cited by examiner

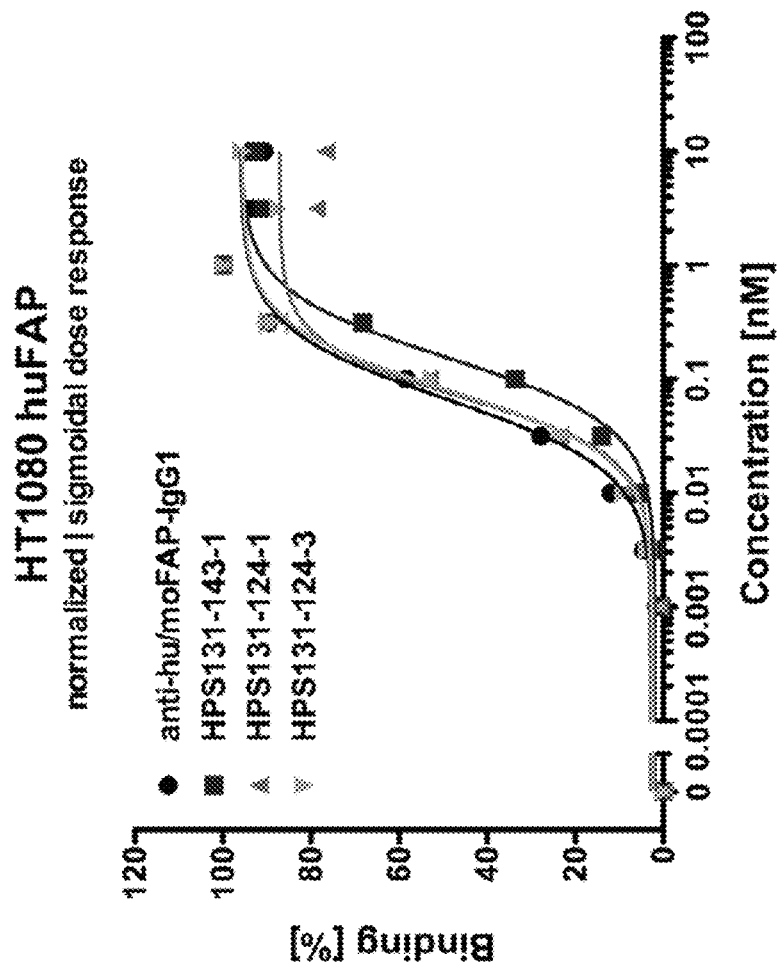

ANTIBODY-DRUG CONJUGATES AND IMMUNOTOXINS

CROSS REFERENCE TO RELATED APPLICATIONS

This is the continuation of co-pending U.S. patent application Ser. No. 15/116,430, filed Dec. 5, 2016, which is the § 371 U.S. National Stage of International Application No. PCT/EP2015/052341, filed Feb. 4, 2015, which was published in English under PCT Article 21(2), which in turn claims the benefit of GB Application No. 1402006.9, filed Feb. 6, 2014, which is incorporated by reference herein in its entirety.

JOINT RESEARCH AGREEMENT

This application describes and claims certain subject matter that was developed under a written joint research agreement between TUBE Pharmaceuticals, GmbH and ONCOMATRYX BIOPHARMA, S.L. (previously ONCOMATRIX, S.L.), having an effective date of May 20, 2013.

SEQUENCE LISTING

The Sequence Listing is submitted as an ASCII text file in the form of the file named Sequence_Listing.txt, which was created on Oct. 16, 2018, and is ~32 kilobytes, which is incorporated by reference herein.

FIELD OF THE INVENTION

The present invention relates to antibody-drug conjugates (ADCs) and Immunotoxins that target Fibroblast Activating Protein a (FAP), and to their use in medicine, e.g. in the treatment of certain cancers.

BACKGROUND TO THE INVENTION

Malignant epithelial tumors are the main cancer-related cause of human death. These solid tumors frequently exhibit significant stromal reactions such as the so-called "desmoplastic stroma" or "reactive stroma", which represents 20-60% of total tumor mass and is characterized by the existence of large numbers of stromal cells and dense extracellular matrix (ECM). Recent studies have indicated the tumor-promoting roles of stromal cells, as exemplified by vascular cells, immune cells, fibroblasts, myofibroblasts, adipocytes and bone marrow-derived progenitors (1-6). In particular, considerable numbers of cancer-associated fibroblasts (CAFs) are frequently observed within tumor-associated stroma of various human cancers, including breast, lung, colon, and pancreas carcinomas (14,15). Interacting coordinately with the different components of the stroma, CAFs have the ability to promote neoangiogenesis and tumor growth; CAFs have also been shown as crucial for the development of aggressive tumors and tumor invasiveness during cancer progression (16-25); CAFs facilitate the spreading and infiltration of tumor cells in distant organs, thus contributing to formation of metastases. Importantly, the relevance of stromal cells to the failure of systemic drug delivery to tumors and to the development of drug resistance has also been indicated (7-11).

The identification of cellular and molecular targets abrogating stromal-tumor cell interactions and thus attenuating tumorigenesis is currently one of the most important subjects in translational oncology. Indeed, targeting the peritumoral stroma is a fairly new strategy to treat metastatic tumors, which represent more than 90% of cancer patient mortality: only a few products have obtained therapeutic approval up to now, most of them being anti-angiogenic drugs (Avastin®; 26). Identifying and targeting other new molecules within the tumor microenvironment is then essential for increasing the efficacy of conventional therapies in combination with the stroma-based therapeutic approaches, and represent a powerful approach for cancer and metastasis treatment (12, 13).

Monoclonal antibody (MAb)—based drugs represent a great promise in the fight against cancer. This is because they allow the treatment to be aimed at a molecular level in a precise and specific way. These advantages, together with their commercial appeal (short development times, restricted competence and being easily exportable to other cancer types once they have been approved), have pushed many pharmaceutical companies to invest heavily in the development of new antibody-based molecules, as well as in the in-licensing of new molecules or technologies from biotech companies.

However, despite the clinical success of therapeutic antibodies, naked MAbs targeting cell surface tumor antigens rarely present sufficient efficacy on their own. To increase the low activity of the MAbs, novel strategies are focusing on binding them to toxic molecules. Plant and bacterial toxins as well as small chemotherapeutic molecules can be good candidates, since they are very potent and active in very small quantities.

The field of immunotoxins (ITs) and Antibody-Drug conjugates (ADCs) for the treatment of cancer has recently experienced a growing development activity by pharmaceutical companies, due to the technological advances performed during the last years, aimed at solving the problems they initially presented about immunogenicity, undesirable toxicity, production, half-life and resistance.

Immunoconjugates are made of a human, humanized or chimeric recombinant antibody, covalently linked to a cytotoxic drug. The main goal of such a structure is joining the power of small cytotoxic (300 to 1000 Da) and the high specificity of tumor-associated antigen targeted (TAA) MAbs.

The Ab must be very selective to reach the antigen, whose expression must be restricted in normal cells. The Ab also must be internalized efficiently into the cancerous cells.

The cytotoxic agent selected as the effector moiety must kill cells only after internalization and release into the cell cytoplasm. The most commonly used payloads in ADCs are DNA-harming drugs such as calicheamicins, duocarmicins, or microtubule-targeting compounds like auristatins and maitansinoids.

The Ab-cytotoxic linkers are designed to be stable systemically and to release the cytotoxic within the target cells.

TAAs are frequently cell membrane proteins that are overexpressed in diseased tissues or at least expressed sufficiently to facilitate the internalization-activated cytotoxicity. Ideally the antigen presents a restricted expression in normal tissues with a low or absent expression in vital organs. On top of this, the tumor antigen must be recognized selectively and with high affinity by an Ab.

In many types of human cancer, fibroblast response is characterized by the induction of a cell surface protein, Fibroblast Activating Protein a (FAPα), a serine protease of 95 kDa whose expression is highly restricted to developing organs, wound-healing and tissue remodeling.

FAP presents the following characteristics:
Type II membrane glycoprotein with SER-protease activity (collagenase+DPP)
89% human-murine protein homology
Tumor stroma-expressed in >90% carcinomas (breast, pancreas, lung, bladder and colon)
Transitory and highly restricted expression in normal adult tissues during wound-healing and developing organs.
FAP(+) fibroblasts located closed to tumor vasculature
Very focal expression
Internalization
Implication in extracellular matrix remodeling, tumor growth and metastasis.

FAP expression has been recently found in Pancreas tumor cells as well as tumor-associated stromal fibroblasts. FAP expression was correlated with shorter patient survival and worse prognosis, suggesting a possible FAP-based autocrine/paracrine loop in this type of tumor (32).

During the last 10 years, Kontermann and Pfizenmaier (IZI, University of Stuttgart, Germany) have developed anti-FAP MAb derivatives against both human and murine proteins (27, 28). They have shown in vitro that anti-FAP scFv immunoliposomes bind specifically FAP+ cells and get internalized (29). In a recent study they demonstrated the anti-tumoral effect of nanoparticles covered with lipids and anti-FAP scFvs and loaded with TNFα (30).

Treatment with murine MAb FAPS-DM1 immunotoxin induced long lasting inhibition of tumor growth and full regression in pancreas and lung cancer xenograft models, without any intolerance-related effect (31).

Despite these advances, there remains an unmet need for further therapeutic strategies for the treatment of tumors, including epithelial tumors, and for components for use in such therapeutic strategies. The present invention addresses these and other needs.

BRIEF DESCRIPTION OF THE INVENTION

Broadly, the present invention relates to anti-FAP antibodies, conjugates thereof and optimised payloads for use in antibody conjugate strategies. In particular, the present inventors have found that anti-FAP antibodies as described herein exhibit highly specific binding, and fast and efficient internalisation. Moreover, the present inventors have found that the A chain of Nigrin b can be isolated and produced in bacterial host cells, yet retains in vitro Ribosome Inactivating activity in the absence of the Nigrin-b B-chain and, only once conjugated to an antibody, exhibits both the ability to translocate into cells and the resulting cytotoxic activity without Nigrin-b B-chain.

The Nigrin-b A-chain described herein and/or cytolysin derivatives are advantageously conjugated to anti-FAP antibodies for use in the treatment of tumors.

Accordingly, in a first aspect the present invention provides a conjugate having the formula I:

$$A\text{-}(L\text{-}D)_p \qquad (I)$$

or a pharmaceutically acceptable salt or solvate thereof, wherein:

A is an antibody that selectively binds FAP;

L is a linker;

D is a drug comprising a cytolysin or a Nigrin-b A-chain; and p is 1 to 10.

In some cases in accordance with this and other aspects of the present invention A is a monoclonal antibody or binding fragment thereof that selectively binds to an extracellular region of human FAP. In some case, A may cross-react to both human and murine FAP. In particular cases A may comprise heavy chain complementarity determining regions 1-3 (CDRH1-3) and light chain complementarity determining regions 1-3 (CDRL1-3) having the following amino acid sequences:

(i) CDRH1: SEQ ID NO: 7 or a variant thereof having up to 1 or 2 amino acid substitutions compared with the sequence of SEQ ID NO: 7;

(ii) CDRH2: SEQ ID NO: 8 or a variant thereof having up to 1 or 2 amino acid substitutions compared with the sequence of SEQ ID NO: 8;

(iii) CDRH3: SEQ ID NO: 9 or a variant thereof having up to 1 or 2 amino acid substitutions compared with the sequence of SEQ ID NO: 9;

(iv) CDRL1: SEQ ID NO: 10 or a variant thereof having up to 1 or 2 amino acid substitutions compared with the sequence of SEQ ID NO: 10;

(v) CDRL2: SEQ ID NO: 11 or a variant thereof having up to 1 or 2 amino acid substitutions compared with the sequence of SEQ ID NO: 11; and (vi) CDRL3: SEQ ID NO: 12 or a variant thereof having up to 1 or 2 amino acid substitutions compared with the sequence of SEQ ID NO: 12.

In certain cases, CDRH1-3 comprise the amino acid sequences of SEQ ID NOS: 7-9, respectively and CDRL1-3 comprise the amino acid sequences of SEQ ID NOS: 10-12, respectively.

In certain cases, A comprises a heavy chain variable region (VH) comprising an amino acid sequence having at least 90%, 95% or 99% sequence identity with the full-length sequence of SEQ ID NO: 5.

In certain cases, A comprises a heavy chain variable region (VH) comprising the amino acid sequence of SEQ ID NO: 5.

In certain cases, A comprises a light chain variable region (VL) comprising an amino acid sequence having at least 90%, 95% or 99% sequence identity with the full-length sequence of SEQ ID NO: 6. In particular, A may comprise a light chain variable region (VL) comprising the amino acid sequence of SEQ ID NO: 6.

In certain cases, A comprises a heavy chain comprising an amino acid sequence having at least 90%, 95% or 99% sequence identity with the full-length sequence of SEQ ID NO: 3. In particular, A may comprise a heavy chain comprising the amino acid sequence of SEQ ID NO: 3.

In certain cases, A comprises a light chain comprising an amino acid sequence having at least 90%, 95% or 99% sequence identity with the full-length sequence of SEQ ID NO: 4. In particular, A may comprise a light chain comprising the amino acid sequence of SEQ ID NO: 4.

In certain cases, A may be a competitively binding anti-FAP antibody that is structurally different from the anti-FAP antibody molecules exemplified herein. For example, A may be an anti-FAP antibody molecule that competes with the anti-FAP IgG1 antibody identified herein as "hu36" for binding to immobilized recombinant human FAP. hu36 has the heavy chain amino acid sequence of SEQ ID NO: 3 and the light chain amino acid sequence of SEQ ID NO: 4. The anti-FAP antibody may, in some case, bind to the same epitope as hu36. Methods for determining antibody binding competition and for epitope mapping are well known in the art, see for example "Epitope Mapping by Competition Assay" Ed Harlow and David Lane, Cold Spring Harb Protoc; 2006; doi:10.1101/pdb.prot4277.

In accordance with this and other aspects of the present invention, D may be a cytolysin. The cytolysin may, in some cases, be a compound disclosed in WO 2008/138561 A1, the entire contents of which is expressly incorporated herein by reference (compounds disclosed therein are also referred to as Tubulysine derivatives). The cytolysin may be synthesised as described in WO 2008/138561. In certain cases, the cytolysin may be as defined in Formula I or Formula IV of WO 2008/138561 A1. In certain cases, the cytolysin may be of formula IV:

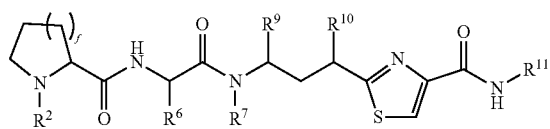

(IV)

wherein:
$R^2$ (i) is directly or indirectly attached to linker L or (ii) is H or is $C_1$-$C_4$ alkyl;
$R^6$ is $C_1$-$C_5$ alkyl;
$R^7$ is $C_1$-$C_5$ alkyl, $CH_2OR^{19}$ or $CH_2OCOR^{20}$, wherein $R^{19}$ is alkyl, $R^{20}$ is $C_2$-$C_6$-alkenyl, phenyl, or $CH_2$-phenyl;
$R^9$ is $C_1$-$C_5$ alkyl;
$R^{10}$ is H, OH, O-alkyl or O-acetyl;
f is 1 or 2;
$R^{11}$ has the following structure:

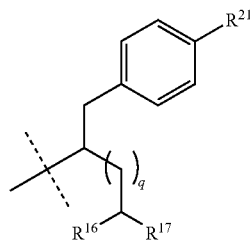

wherein
$R^{21}$ is H, OH, halogen, $NH_2$, alkyloxy, phenyl, alkyl amino or dialkyl amino;
$R^{16}$ is H or a $C_1$-$C_6$-alkyl group;
$R^{17}$ (i) is directly or indirectly attached to linker L or (ii) is $CO_2H$, $CO_2R^{18}$, $CONHNH_2$, OH, $NH_2$, SH or a optionally substituted alkyl, cycloalkyl, heteroalkyl or heterocycloalkyl group, wherein $R^{18}$ is an optionally substituted alkyl, heteroalkyl or hetercycloalkyl group; and
q is 0, 1, 2 or 3;
and wherein the term "optionally substituted" relates to groups,
wherein one or several H atoms can be replaced by F, Cl, Br or I or OH, SH, $NH_2$, or $NO_2$; the term "optionally substituted" further relates to groups, which can be exclusively or additionally substituted with unsubstituted $C_1$-$C_5$ alkyl, $C_2C_6$ alkenyl, $C_2$-$C_6$ alkynyl, $C_1$-$C_6$ heteroalkyl, $C_3$-$C_{10}$ cycloalkyl, $C_2$-$C_9$ heterocycloalkyl, $C_6$-$C_{10}$ aryl, $C_1$-$C_9$ heteroaryl, $C_2$-$C_{12}$ aralkyl or $C_2$-$C_{11}$ heteroaralkyl groups.

In some cases $R^2$ is a bond to linker L.
In some cases $R^{17}$ is C(O)X, CONHNHX, OX, NHX or SX, wherein X is a bond to linker L.
In some cases linker L may further comprise a spacer.
In some cases the spacer has a chain length of 2 to 30 atoms.
In some cases the spacer comprises or consists of an alkylene (i.e. divalent alkyl) or heteroalkylene (i.e. divalent heteroalkyl) group. In some cases the spacer comprises or consists of an alkylene or oxyalkylene group.
In some cases the spacer comprises or consists of a group —$(CH_2)_n$— or —$(OCH_2CH_2)_n$—, wherein n 1.
In some cases the spacer comprises or consists of a group —$(OCH_2CH_2)_n$—, wherein n 1. In particular, n may be 1 to 15, 1 to 10, 1 to 6, or 2 to 5. For example, n may be 3 or 4.
In some cases the spacer comprises between one and six ethylene glycol units, e.g. a triethylene glycol.
In some cases the spacer may be directly attached to group $R^{17}$, or may be attached to group $R^{17}$ via a bridging group.
In some cases the spacer is attached to group $R^{17}$ via a —C(O)X bridging group, wherein X is a bond to $R^{17}$.
In some cases $R^{17}$ is CONHNHX and the spacer is attached to group $R^{17}$ via a —C(O)X bridging group, wherein X represents the bond between the spacer and $R^{17}$.
In some cases $R^{17}$ is CONHNHX and the spacer is a —$(OCH_2CH_2)_n$— attached to $R^{17}$ via a —C(O)X bridging group, wherein n=2, 3 or 4.
In some cases D comprises a cytolysin having the following structure:

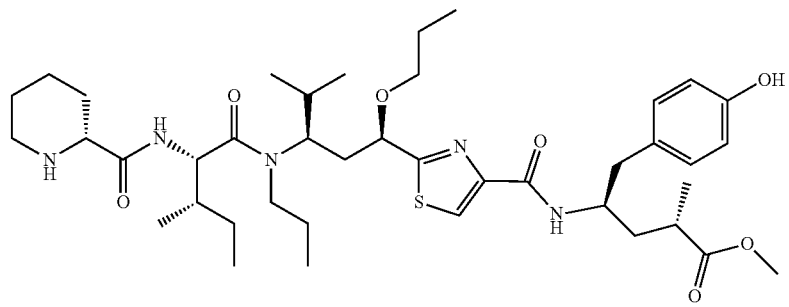 [SMILES: CCCO[C@H](C[C@H](C(C)C)N(CCC)C(=O)[C@@H](NC(=O)[C@H]1CCCCN1)[C@@H](C)CC)c1nc(C(=O)N[C@@H](Cc2ccc(O)cc2)C[C@H](C)C(=O)OC)cs1]

In some cases D comprises a cytolysin having the following structure:
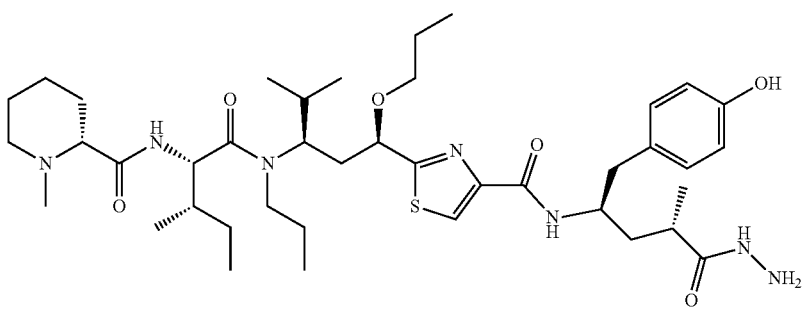 [SMILES: CCCO[C@H](C[C@H](C(C)C)N(CCC)C(=O)[C@@H](NC(=O)[C@H]1CCCCN1C)[C@@H](C)CC)c1nc(C(=O)N[C@@H](Cc2ccc(O)cc2)C[C@H](C)C(=O)NN)cs1]

In certain cases L comprises an attachment group for attachment to A and protease cleavable portion. For example, L may comprise a valine-citrulline unit. In particular, L may comprise maleimidocaproyl-valine-citrulline-p-aminobenzylcarbamate.

In some cases the double bond of the maleimide is reacted with a thiol group of a cysteine residue of the antibody A to form a sulphur-carbon bond in order to effect linkage of the linker L to the antibody A.

In some cases -L-D has a structure selected from the group consisting of:

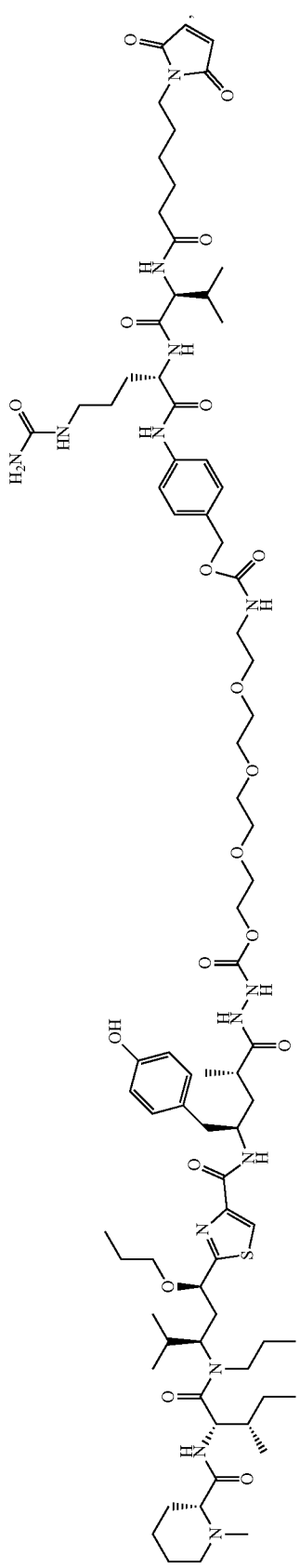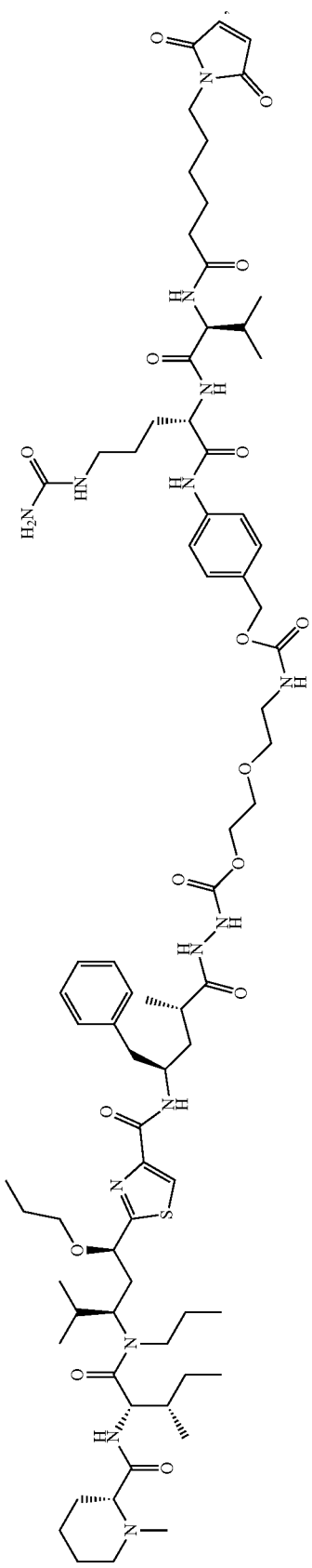

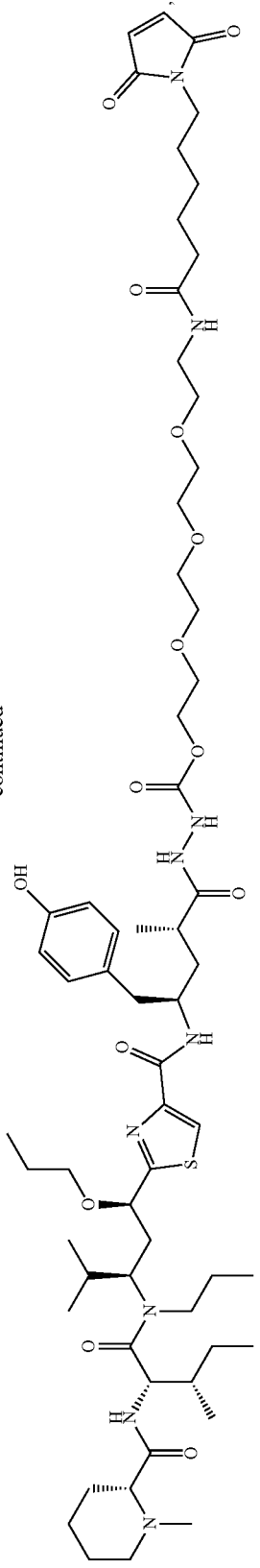
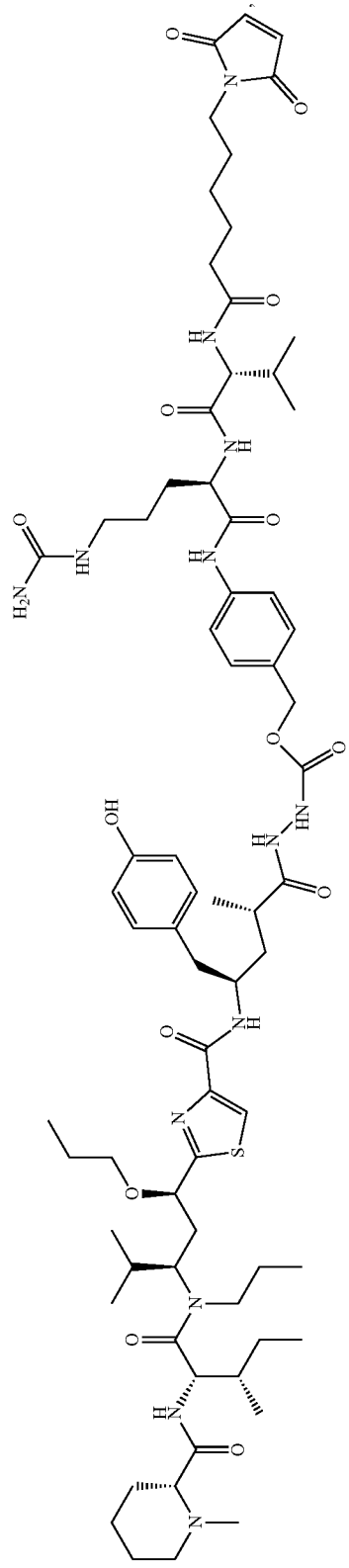
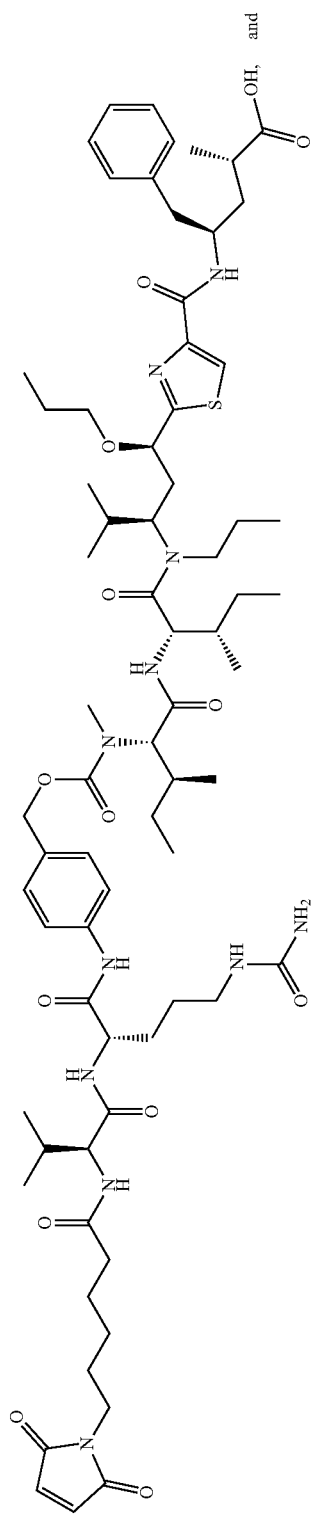

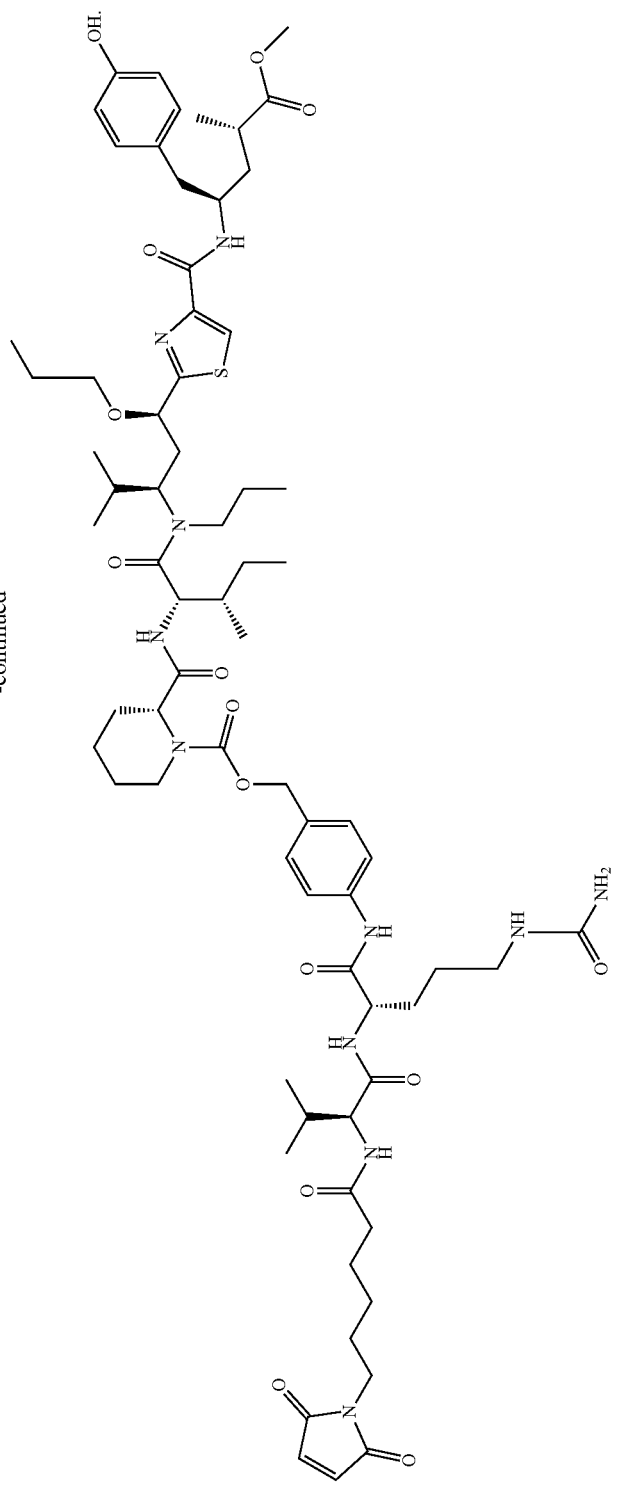

In certain cases -L-D may have the following structure:

*Exact Mass: 1369,74*

In certain cases -L-D may have the following structure:

*Exact Mass: 1383,76*
*Mol. Wt.: 1384,73*

In accordance with this and other aspects of the present invention p may, in some cases, lie in the range 1 to 5, e.g. 1 to 4, or 1 to 3. In particular cases p may be 1 or 2. In particular, cases p may be 3 or 4.

In accordance with this and other aspects of the present invention D may be a Nigrin-b A-chain. Preferably, the Nigrin-b A-chain is in the absence of a Nigrin-b B-chain. The Nigrin-b A-chain may comprise or consist of the sequence of SEQ ID NO: 13.

In certain cases, the Nigrin-b A-chain may be or may have been recombinantly-produced, e.g. in a bacterial host cell. The present inventors have surprisingly found that Nigrin-b A-chain retains its activity (e.g. cytotoxic and/or ribosome inhibiting activity) despite loss of or alteration of native glycosylation such as is the case when the Nigrin-b A-chain is produced recombinantly in a bacterial host cell.

When the conjugate of the present invention comprises a Nigrin-b A-chain as the toxic payload (i.e. D), L may simply be a disulphide bond between a sulphur atom on A and a sulphur atom on D. Therefore, L may comprise or consist of a disulphide bond.

In a second aspect the present invention provides a conjugate as defined in accordance with the first aspect of the invention for use in medicine.

In a third aspect the present invention provides a conjugate as defined in accordance with the first aspect of the invention for use in a method of treatment of a tumor in a mammalian subject.

In some cases the conjugate is for simultaneous, sequential or separate administration with one or more other antitumor drugs. The one or more other antitumor drugs comprise a cytotoxic chemotherapeutic agent or an antiangiogenic agent or an immunotherapeutic agent. In some cases the one or more other antitumor drugs comprise Gemcitabine, Abraxane bevacizumab, itraconazole, carboxyamidotriazole, an anti-PD-1 molecule or an anti-PD-L1 molecule (for example, nivolumab or pembrolizumab).

In certain cases the conjugate is for use in the treatment of a solid tumor. In particular, the conjugate may be for use in the treatment of pancreatic cancer, breast cancer, melanoma, lung cancer, head & neck cancer, ovarian cancer, bladder cancer or colon cancer.

In a fourth aspect the present invention provides a method of treating a tumor in a mammalian subject, comprising administering a therapeutically effective amount of a conjugate as defined in accordance with the first aspect of the invention to the subject in need thereof. In some cases the method may be for treating a solid tumor. In particular, the method may be for treating pancreatic cancer, breast cancer, melanoma, lung cancer, head & neck cancer, ovarian cancer, bladder cancer or colon cancer.

In a fifth aspect the present invention provides use of a cytolysin in the preparation of an antibody-drug conjugate, wherein the antibody is an FAP-specific antibody, e.g., an FAP-specific antibody in accordance with the eighth aspect of the invention. In some case the use may be of a cytolysin in the preparation of an antibody-drug conjugate as defined in accordance with the first aspect of the invention.

In a sixth aspect the present invention provides a conjugate of the first aspect of the invention for use in the treatment of an inflammatory condition (e.g. rheumatoid arthritis).

In a seventh aspect the present invention provides a method of treating an inflammatory condition (e.g. rheumatoid arthritis) in a mammalian subject, comprising administering a therapeutically effective amount of a conjugate of the first aspect of the invention to the subject in need thereof.

In an eighth aspect the present invention provides an isolated Nigrin-b A-chain in the absence of the Nigrin-b B-chain. The amino acid sequence of the Nigrin-b A-chain may comprise or consist of the sequence of SEQ ID NO: 13.

In a ninth aspect the present invention provides use of an isolated Nigrin-b A-chain in accordance with the eighth aspect of the invention in the preparation of an immunotoxin. In some cases, the immunotoxin comprises a monoclonal antibody conjugated and/or bound to said isolated Nigrin-b A-chain (in the absence of the Nigrin-b B-chain).

In some cases the immunotoxin comprises an antibody, such as a monoclonal antibody, e.g. a human monoclonal antibody, that selectively binds FAP. In some cases, the immunotoxin comprises an antibody in accordance with the tenth aspect of the invention.

In a tenth aspect the present invention provides a monoclonal antibody, e.g. a human monoclonal antibody, that selectively binds FAP and which comprises a heavy chain comprising the amino acid sequence of SEQ ID NO: 3 and a light chain comprising the amino acid sequence of SEQ ID NO: 4.

In an eleventh aspect the present invention provides the antibody of the tenth aspect of the invention for use in medicine. The antibody may be for use in the treatment of an inflammatory condition (e.g. rheumatoid arthritis).

In a twelfth aspect the present invention provides use of a monoclonal antibody in accordance with the tenth aspect of the invention in the preparation of an antibody-drug conjugate or an immunotoxin.

In a thirteenth aspect the present invention provides a host cell comprising a vector comprising a polynucleotide that encodes at least one polypeptide having an amino acid sequence selected from the group consisting of: SEQ ID NOS: 1-6 and 13. In some cases the polynucleotide may comprise the nucleic acid sequence of SEQ ID NO: 14.

In a fourteenth aspect the present invention provides a process for the production of a conjugate in accordance with the first aspect of the invention, comprising:
(a) derivatising the antibody that selectively binds FAP to introduce at least one sulphydryl group; and
(b) reacting the derivatised antibody with an appropriate residue (e.g. a cysteine amino acid) on a Nigrin-b A-chain (absent Nigrin-b B-chain) under conditions which permit the formation of a disulphide bond linkage between the antibody and the Nigrin-b A-chain thereby producing the conjugate. The process may further comprise a step (c) of purifying and/or isolating the conjugate.

In some cases step (a) may comprise reacting the antibody with 4-succynimidyloxycarbonyl-α-methyl-α-(2-pyridyl-dithio)toluene (SMPT), N-succynimidyl 3-(2-pyridyl-dithiopropionate) (SPDP) or methyl 4-mercaptobutyrimidate.

In a fifteenth aspect the present invention provides a process for the production of a conjugate in accordance with the first aspect of the invention, comprising:
(a) linking the antibody that selectively binds FAP to the linker via a thiol group; and
(b) linking the cytolysin to the linker via an appropriate group on the cytolysin molecule. In some cases, the cytolysin is linked to the linker via position $R_2$ or position $R_{17}$. Steps (a) and (b) can be performed in either order. In an optional further step (c), the process may comprise purifying and/or isolating the conjugate.

The present invention includes the combination of the aspects and preferred features described except where such a combination is clearly impermissible or is stated to be expressly avoided. These and further aspects and embodiments of the invention are described in further detail below and with reference to the accompanying examples and figures.

BRIEF DESCRIPTION OF THE FIGURES

FIG. 1A) SDS-PAGE analysis of purified scFv fragments. Coomassie staining. R-reducing, NR—non reducing. FIG. 1B) Flow cytometry analysis of binding of hu36 (humanized) and mo36 (chimeric) to HT1080-huFAP cells. Bound antibodies were detected with an anti-His-tag antibody (n=2). FIG. 1C) ELISA of binding of hu36 scFv and mo36 scFv to immobilized recombinant human FAP (coated at 100 ng/ml). Bound antibodies were detected with an HRP-conjugated anti-Myc-tag antibody.

FIGS. 15A-15C show ELISA and FACS analysis of ADC471 binding to FAP target. ELISA detection of ADC-471 binding to huFAP fusion protein compared to naked anti-hu/mo FAP hu36 antibody; EC50 values are indicated for HPS124-3 ADC-471 molecule with DAR=3.48 (FIG. 15A); FACS analysis of binding on HT1080-huFAP, HT1080-wt and HEK293 cells of HPS131-143-1 (ADC-471; DAR 4), HPS131-124-1 (ADC-467; DAR 1.2) and HPS131-124-3 (ADC-471; DAR 3.48) ADCs (FIGS. 15B and 15C). $EC_{50}$ values are indicated for this latter (FIG. 15B).

DETAILED DESCRIPTION OF THE INVENTION

Figure 1A:
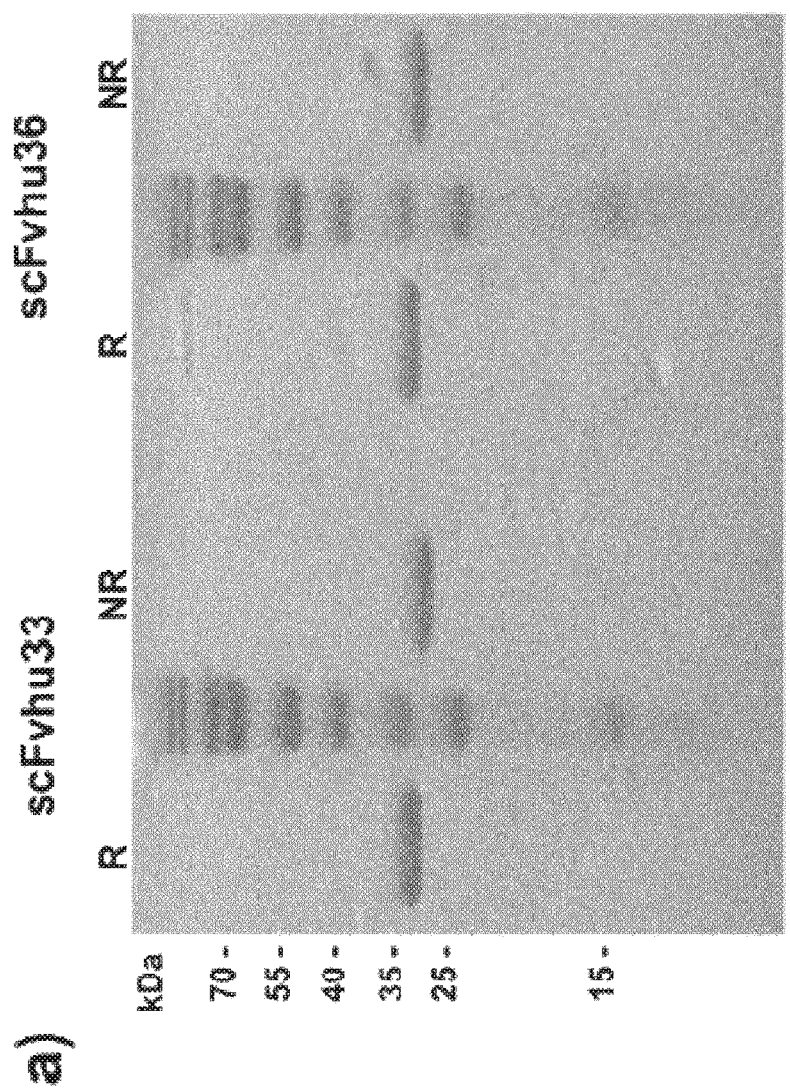
FIGS. 1A-1C show characterization of humanized scFv hu33 and hu36.

In describing the present invention, the following terms will be employed, and are intended to be defined as indicated below.

FAP

As used herein "Fibroblast activation protein", "fibroblast activating protein", "FAP" and "FAPα" are used interchangeably. The FAP may be an FAP of any mammalian species. In some cases FAP is human FAP (also known as Seprase, 170 kDa melanoma membrane-bound gelatinase, fibroblast activation protein alpha or integral membrane serine protease), the amino acid sequence of which is disclosed at UniProt accession No. Q12884 (Version 140, dated 11 Dec. 2013) (SEQ ID NO: 15). In some cases, a molecule that binds FAP (e.g. an antibody molecule or a conjugate thereof) may bind to a region of the extracellular domain of FAP. The extracellular domain of human FAP comprises residues 26-760 of the full-length human FAP protein. In some cases FAP is murine FAP (also known as fibroblast activation protein alpha or integral membrane serine protease), the amino acid sequence of which is disclosed at UniProt accession No. P97321 (Version 117, dated 11 Dec. 2013) (SEQ ID NO: 16). The extracellular domain of murine FAP comprises residues 26-761 of the full-length murine FAP protein.

Conjugate

As used herein "conjugate" includes the resultant structure formed by linking molecules and specifically includes antibody-drug conjugates (ADCs) and immunotoxins (ITs).

Selectively Binds

The terms selectively binds and selective binding refer to binding of an antibody, or binding fragment thereof, to a predetermined molecule (e.g. an antigen) in a specific manner. For example, the antibody, or binding fragment thereof, may bind to FAP, e.g. an extracellular portion thereof, with an affinity of at least about $1\times10^7 M^{-1}$, and may bind to the predetermined molecule with an affinity that is at least two-fold greater (e.g. five-fold or ten-fold greater) than its affinity for binding to a molecule other than the predetermined molecule.

Antibody Molecule

As used herein with reference to all aspects of the invention, the term "antibody" or "antibody molecule" includes any immunoglobulin whether natural or partly or wholly synthetically produced. The term "antibody" or "antibody molecule" includes monoclonal antibodies (mAb) and polyclonal antibodies (including polyclonal antisera).

Antibodies may be intact or fragments derived from full antibodies (see below). Antibodies may be human antibodies, humanised antibodies or antibodies of non-human origin. "Monoclonal antibodies" are homogeneous, highly specific antibody populations directed against a single antigenic site or "determinant" of the target molecule. "Polyclonal antibodies" include heterogeneous antibody populations that are directed against different antigenic determinants of the target molecule. The term "antiserum" or "antisera" refers to blood serum containing antibodies obtained from immunized animals.

It has been shown that fragments of a whole antibody can perform the function of binding antigens. Thus reference to antibody herein, and with reference to the methods, arrays and kits of the invention, covers a full antibody and also covers any polypeptide or protein comprising an antibody binding fragment. Examples of binding fragments are (i) the Fab fragment consisting of $V_L$, $V_H$, $C_L$ and $C_H1$ domains; (ii) the Fd fragment consisting of the $V_H$ and $C_H1$ domains; (iii) the Fv fragment consisting of the $V_L$ and $V_H$ domains of a single antibody; (iv) the dAb fragment which consists of a $V_H$ domain; (v) isolated CDR regions; (vi) $F(ab')_2$ fragments, a bivalent fragment comprising two linked Fab fragments (vii) single chain Fv molecules (scFv), wherein a $V_H$ domain and a $V_L$ domain are linked by a peptide linker which allows the two domains to associate to form an antigen binding site; (viii) bispecific single chain Fv dimers (WO 93/11161) and (ix) "diabodies", multivalent or multispecific fragments constructed by gene fusion (WO94/13804; 58). Fv, scFv or diabody molecules may be stabilised by the incorporation of disulphide bridges linking the VH and VL domains. Minibodies comprising a scFv joined to a CH3 domain may also be made.

In relation to a an antibody molecule, the term "selectively binds" may be used herein to refer to the situation in which one member of a specific binding pair will not show any significant binding to molecules other than its specific binding partner(s). The term is also applicable where e.g. an antigen-binding site is specific for a particular epitope that is carried by a number of antigens, in which case the specific binding member carrying the antigen-binding site will be able to bind to the various antigens carrying the epitope.

In some cases in accordance with the present invention the antibody may be a fully human antibody.

Cytotoxic Chemotherapeutic Agents

In some cases in accordance with any aspect of the present invention, the conjugate of the invention may administered with, or for administration with, (whether simultaneously, sequentially or separately) one or more other antitumor drugs, including, but not limited to, a cytotoxic chemotherapeutic agent or an anti-angiogenic agent or an immunotherapeutic agent.

Cytotoxic chemotherapeutic agents are well known in the art and include anti-cancer agents such as: Alkylating agents including nitrogen mustards such as mechlorethamine (HN2), cyclophosphamide, ifosfamide, melphalan (L-sarcolysin) and chlorambucil; 10 ethylenimines and methylmelamines such as hexamethylmelamine, thiotepa; alkyl sulphonates such as busulfan; nitrosoureas such as carmustine (BCNU), lomustine (CCNLJ), semustine (methyl-CCN-U) and streptozoein (streptozotocin); and triazenes such as decarbazine (DTIC; dimethyltriazenoimidazolecarboxamide); Antimetabolites including folic acid analogues such as methotrexate (amethopterin); pyrimidine analogues such as fluorouracil (5-fluorouracil; 5-FU), floxuridine (fluorodeoxyuridine; FUdR) and cytarabine (cytosine arabinoside); and purine analogues and related inhibitors such as mercaptopurine (6-mercaptopurine; 6-MP), thioguanine (6-thioguanine; TG) and pentostatin (2'-deoxycofonnycin). Natural Products including vinca alkaloids such as vinblastine (VLB) and vincristine; epipodophyllotoxins such as etoposide and teniposide; antibiotics such as dactinomycin (actinomycin D), daunorabicin (daunomycin; rubidomycin), doxorubicin, bleomycin, plicamycin (mithramycin) and mitomycin (mitomycin Q; enzymes such as L-asparaginase; and biological response modifiers such as interferon alphenomes. Miscellaneous agents including platinum coordination complexes such as cisplatin (cis-DDP) and carboplatin; anthracenedione such as mitoxantrone and antbracycline; substituted urea such as hydroxyurea; methyl hydrazine derivative such as procarbazine (N-methylhydrazine, MIH); and adrenocortical suppressant such as mitotane (o, p'-DDD) and aminoglutethimide; taxol and analogues/derivatives; and hormone agonists/antagonists such as flutamide and tamoxifen. A further preferred cytotoxic agent is Gemcitabine (Gemzar®). A further preferred cytotoxic agent is Paclitaxel bound to human serum albumin (Abraxane®).

Anti-angiogenic agents are well known in the art and include anti-cancer agents such as bevacizumab, itraconazole, and carboxyamidotriazole.

Immunotherapeutic agents are known in the art and include, for example, anti-programmed cell death protein 1 (PD-1) antibodies and anti-programmed death-ligand 1 (PD-L1) antibodies, including Nivolumab (MDX1106) and Pembrolizumab (MK-3475).

Pharmaceutical Compositions

The conjugates of the present invention may be comprised in pharmaceutical compositions with a pharmaceutically acceptable excipient.

A pharmaceutically acceptable excipient may be a compound or a combination of compounds entering into a pharmaceutical composition which does not provoke secondary reactions and which allows, for example, facilitation of the administration of the conjugate, an increase in its lifespan and/or in its efficacy in the body or an increase in its solubility in solution. These pharmaceutically acceptable vehicles are well known and will be adapted by the person skilled in the art as a function of the mode of administration of the conjugate.

In some embodiments, conjugates of the present invention may be provided in a lyophilised form for reconstitution prior to administration. For example, lyophilised conjugates may be re-constituted in sterile water and mixed with saline prior to administration to an individual.

Conjugates of the present invention will usually be administered in the form of a pharmaceutical composition, which may comprise at least one component in addition to the conjugate. Thus pharmaceutical compositions may comprise, in addition to the conjugate, a pharmaceutically acceptable excipient, carrier, buffer, stabilizer or other materials well known to those skilled in the art. Such materials should be non-toxic and should not interfere with the efficacy of the conjugate. The precise nature of the carrier or other material will depend on the route of administration, which may be by bolus, infusion, injection or any other suitable route, as discussed below.

For intra-venous administration, e.g. by injection, the pharmaceutical composition comprising the conjugate may be in the form of a parenterally acceptable aqueous solution which is pyrogen-free and has suitable pH, isotonicity and stability. Those of relevant skill in the art are well able to prepare suitable solutions using, for example, isotonic vehicles, such as Sodium Chloride Injection, Ringer's Injection, Lactated Ringer's Injection. Preservatives, stabilizers, buffers, antioxidants and/or other additives may be employed as required including buffers such as phosphate, citrate and other organic acids; antioxidants, such as ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3'-pentanol; and m-cresol); low molecular weight polypeptides; proteins, such as serum albumin, gelatin or immunoglobulins; hydrophilic polymers, such as polyvinylpyrrolidone; amino acids, such as glycine, glutamine, asparagines, histidine, arginine, or lysine; monosaccharides, disaccharides and other carbohydrates including glucose, mannose or dextrins; chelating agents, such as EDTA; sugars, such as sucrose, mannitol, trehalose or sorbitol; salt-forming counter-ions, such as sodium; metal complexes (e.g. Zn-protein complexes); and/or non-ionic surfactants, such as TWEEN™, PLURONICS™ or polyethylene glycol (PEG).

Subject

The subject may be a human, a companion animal (e.g. a dog or cat), a laboratory animal (e.g. a mouse, rat, rabbit, pig or non-human primate), a domestic or farm animal (e.g. a pig, cow, horse or sheep). Preferably, the subject is a human. In some cases the subject may be a human diagnosed with or classified as being at risk of developing a cancer, e.g., an epithelial tumor. In certain cases the subject may be a laboratory animal, e.g., a mouse model of a cancer. In certain cases the subject may be a mammal (e.g. a human) that has been diagnosed with or classified as being at risk of developing an inflammatory condition, such as rheumatoid arthritis (RA). In particular, the subject may be a human having RA.

Cancer

The anti-FAP conjugates described herein find use in the treatment of a tumor in a mammalian subject. The tumor may be a solid tumor. In particular, the tumor may be a pancreatic cancer, breast cancer, melanoma, lung cancer, head & neck cancer, ovarian cancer, bladder cancer or colon cancer.

Inflammatory Condition

In some cases in accordance with the present invention, the anti-FAP antibody or the antibody drug conjugate may be for use in the treatment of an inflammatory condition. FAP expression has been reported in fibroblast-like synoviocytes (FLSs) in rheumatoid arthritis (RA) patients (see, e.g., Bauer et al., *Arthritis Res. Therp.* (2006):8(6); R171). The present inventors believe that the anti-FAP antibodies described herein, and/or conjugates thereof described herein, are able to ameliorate RA and/or symptoms of RA.

The following is presented by way of example and is not to be construed as a limitation to the scope of the claims.

EXAMPLES

Example 1—Production of Anti-FAP Antibodies

Anti-FAP scFvs selected by phage display from an immunized FAP$^{-/-}$ knock-out mouse have been described previously (28). Two scFvs, "MO36" and "MO33", cross-reactive for human and murine FAP (28) were converted into full-length IgG for subsequent characterisation studies and for generation of immunotoxins and ADCs. These scFv (scFv33 and scFv36) were used to generate chimeric antibodies, fusing heavy and light chain constant domains to VH and VL, respectively. In addition, both were humanized by CDR grafting and tested for binding to FAP-expressing cells and recombinant FAP in comparison to the parental scFv. From this comparison, the best binder was used to generate full-length IgG. All scFvs were produced in *E. coli* and purified by IMAC, IgGs were produced in mammalian cells (CHO) using the Lonza GS expression vectors pEE6.4 and pEE14.4 developed for antibody production. Features of the scFvs are summarized in Table 1.

TABLE 1 antibodies, specificities, subclass, and vectors used as starting material

| Format | Species | Antigen | V1 Clone | Subclass | Vector | Plasmid DNA # |
|---|---|---|---|---|---|---|
| scFv | mouse | hu/mo FAP | mo33 | lambda | pAB1 | 376 |
| scFv | mouse | hu/mo FAP | mo36 | kappa | pAB1 | 277 |
| scFv | humanized | hu/mo FAP | hu33 | lambda | pAB1 | 1214 |
| scFv | humanized | hu/mo FAP | hu36 | kappa | pAB1 | 1215 |

Figure 1B:
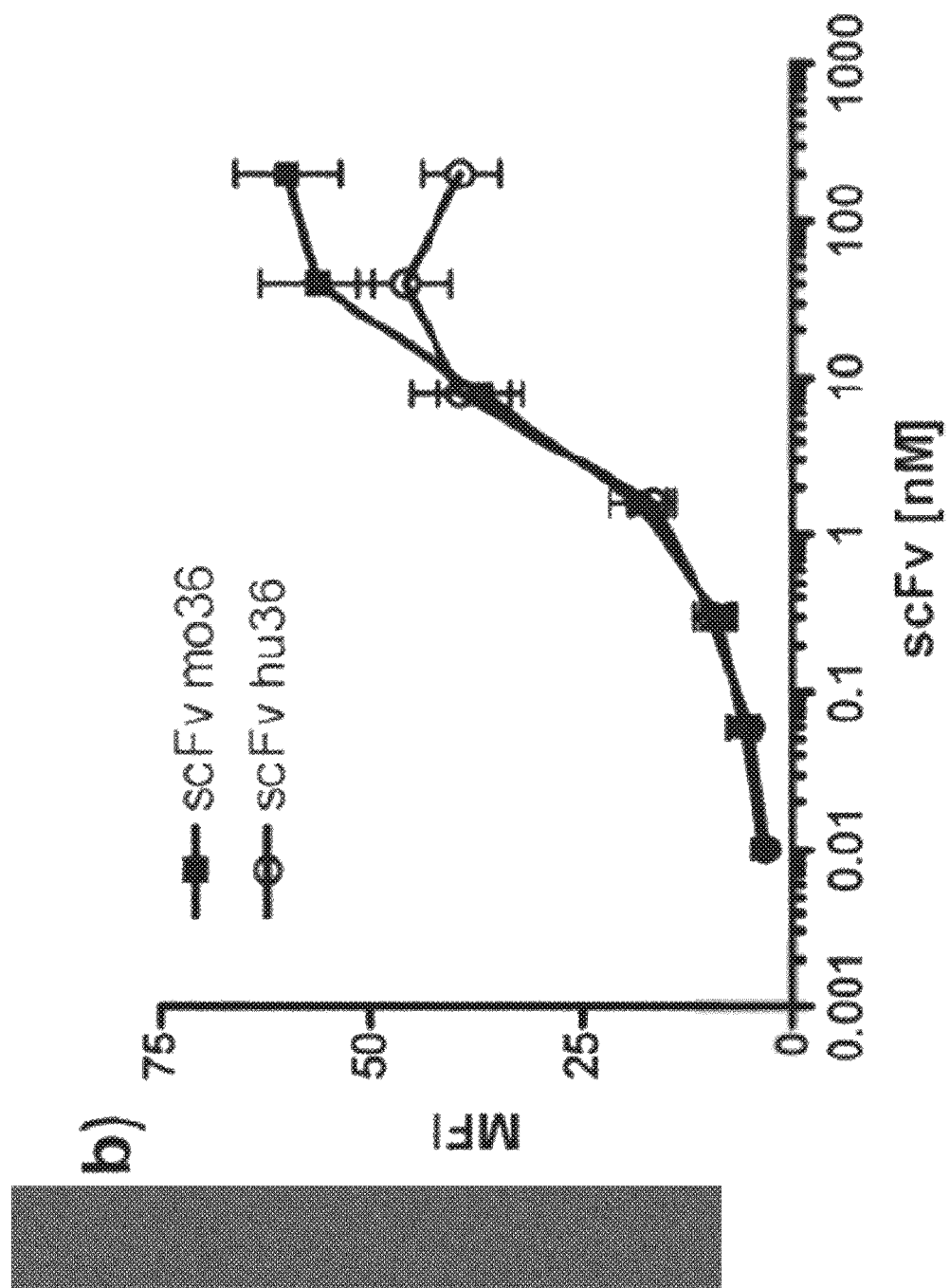
Figure 1C:
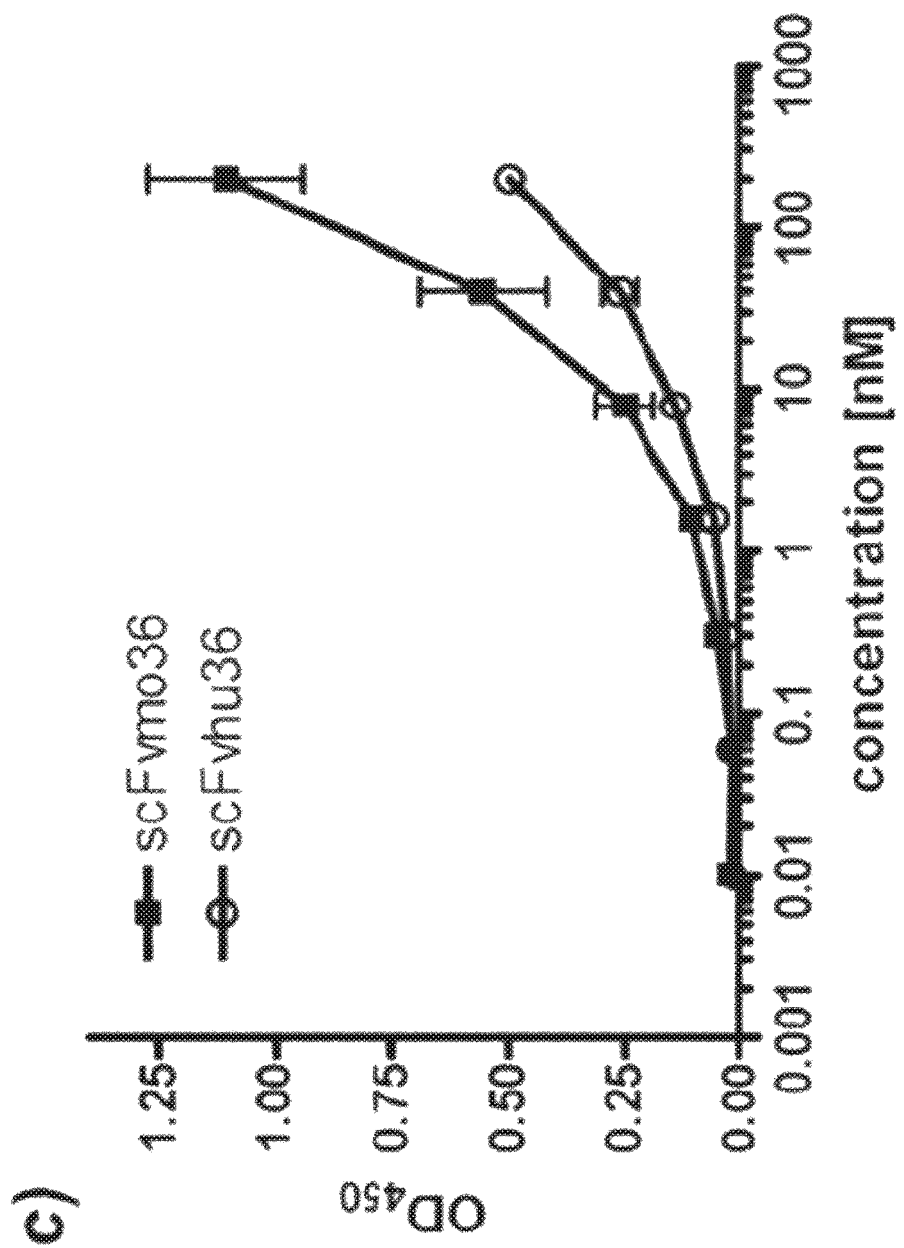

All scFvs were bacterially produced in *E. coli* TG1 and purified from the periplasmic extracts of 1 L cultures by IMAC. Both humanized antibodies (scFv hu33 and hu36) were purified in soluble form with yields of approximately 0.6 mg/L culture. In SDS-PAGE the proteins migrated with the expected size of approximately 30 kDa (FIG. 1A). Purity was estimated to be >90%. In flow cytometry experiments using HT1080 cells expressing human FAP (stable transfectants), a similar binding was observed for scFv hu36 and mo36 scFv, which was also produced in bacteria (not shown). $EC_{50}$ values were in the low nanomolar range. Some differences were observed at higher concentrations (FIG. 1B). scFv hu33 showed no binding or only marginal binding in these experiments. Further development therefore focused on hu36. Binding of hu36 scFv was also observed by ELISA with recombinant human FAP (extracellular region aa 26-760; R&D systems), although binding was somewhat weaker than that seen for mo36 scFv (FIG. 1C).

Plasmids corresponding to full length IgG1 antibodies were generated and transfected into CHO cells for production of antibodies in Lonza's CHO expressing system with yields of approximately 1 mg/L of cell culture (lab scale). Antibodies were purified from cell culture supernatant by protein A chromatography. Purified proteins were characterized by SDS-PAGE and size exclusion chromatography. Bioactivity was analyzed by ELISA using recombinant FAP and detection of bound antibodies with HRP-conjugated anti-human IgG antibodies. Cell binding was analyzed by flow cytometry using HT1080-FAP cell line.

Results:

Plasmids generated (and sequenced):

mo36 IgG1: pEE14.4 mo36-IgG1   OCMTX001p (chimeric anti-FAP IgG1)
hu36 IgG1: pEE14.4 hu36-IgG1   OCMTX002p (humanized anti-FAP IgG1)

Example 2—Characterisation of Anti-FAP Antibodies

The amino acid sequences of humanized anti-FAP IgG1 hu36 (hu36-IgG1) heavy chain (HC) and light chain (LC), respectively are shown below:

Anti-FAP hu36-IgG1-HC:

(SEQ ID NO: 1)

METDTLLLWVLLLWVPGSTG

QVQLVQSGAEVKKPGASVKVSCKASGYTFTENIIHWVRQAPGQGLEWMGWFHPGSGSIKYNEKFKDRVTM

TADTSTSTVYMELSSLRSEDTAVYYCARHGGTGRGAMDYWGQGTLVTVSSASTKGPSVFPLAPSSKSTSG

GTAALGCLVKDYFPEPVTVSWNSGALTSGVHTFPAVLQSSGLYSLSSVVTVPSSSLGTQTYICNVNHKPS

NTKVDKKVEPKSCDKTHTCPPCPAP*PVA*GPSVFLFPPKPKDTLMISRTPEVTCVVVDVSHEDPEVKFNWY

VDGVEVHNAKTKPREEQYNSTYRVVSVLTVLHQDWLNGKEYKCKVSNK*G*LP*SS*IEKTISKAKGQPREPQV

YTLPPSRDELTKNQVSLTCLVKGFYPSDIAVEWESNGQPENNYKTTPPVLDSDGSFFLYSKLTVDKSRWQ

QGNVFSCSVMHEALHNHYTQKSLSLSPGK

```
aa                          449
MW of processed HC          49,069
Theoretical pI              8.69
```
Potential glycosylation site (double underlined): N297
Mutations leading to ADCC and CDC deficiency are shown in bold italics
(see also WO 99/58572)
Signal sequence is shown boxed
VH domain is underlined; CDRH1-H3 are shown in bold and curved
underlined.

Anti-FAP hu36-IgG1-LC:

(SEQ ID NO: 2)

METDTLLLWVLLLWVPGSTG

DIQMTQSPSSLSASVGDRVTITCRASKSVSTSAYSYMHWYQQKPGKAPKLLIYLASNLESGVPSRFSGSG

SGTDFTLTISSLQPEDFATYYCQHSRELPYTFGQGTKLEIKRTVAAPSVFIFPPSDEQLKSGTASVVCLL

NNFYPREAKVQWKVDNALQSGNSQESVTEQDSKDSTYSLSSTLTLSKADYEKHKVYACEVTHQGLSSPVT

KSFNRGEC

```
aa                          218
MW of processed HC          23,919
theoretical pI              7.77
```
signal sequence is boxed
VL domain is underlined; CDRL1-L3 are shown in bold and curved
underlined.

hu36-IgG1-HC—without signal sequence:

(SEQ ID NO: 3)

QVQLVQSGAEVKKPGASVKVSCKASGYTFTENIIHWVRQAPGQGLEWMGWFHPGSGSIKYNEKFKDRVTM

TADTSTSTVYMELSSLRSEDTAVYYCARHGGTGRGAMDYWGQGTLVTVSSASTKGPSVFPLAPSSKSTSG

GTAALGCLVKDYFPEPVTVSWNSGALTSGVHTFPAVLQSSGLYSLSSVVTVPSSSLGTQTYICNVNHKPS

NTKVDKKVEPKSCDKTHTCPPCPAP*PVA*GPSVFLFPPKPKDTLMISRTPEVTCVVVDVSHEDPEVKFNWY

VDGVEVHNAKTKPREEQYNSTYRVVSVLTVLHQDWLNGKEYKCKVSNK*G*LP*SS*IEKTISKAKGQPREPQV

YTLPPSRDELTKNQVSLTCLVKGFYPSDIAVEWESNGQPENNYKTTPPVLDSDGSFFLYSKLTVDKSRWQ

QGNVFSCSVMHEALHNHYTQKSLSLSPGK hu36-IgG1-LC—without signal sequence:

(SEQ ID NO: 4)

DIQMTQSPSSLSASVGDRVTITCRASKSVSTSAYSYMHWYQQKPGKAPKLLIYLASNLESGVPSRFSGSG

-continued

```
SGTDFTLTISSLQPEDFATYYCQHSRELPYTFGQGTKLEIKRTVAAPSVFIFPPSDEQLKSGTASVVCLL

NNFYPREAKVQWKVDNALQSGNSQESVTEQDSKDSTYSLSSTLTLSKADYEKHKVYACEVTHQGLSSPVT

KSFNRGEC
``` hu36-VH:
(SEQ ID NO: 5)
```
QVQLVQSGAEVKKPGASVKVSCKASGYTFTENIIHWVRQAPGQGLEWMGWFHPGSGSIKYNEKFKDRVTM

TADTSTSTVYMELSSLRSEDTAVYYCARHGGTGRGAMDYWGQGTLVTVSS
``` hu36-VL:
(SEQ ID NO: 6)
```
DIQMTQSPSSLSASVGDRVTITCRASKSVSTSAYSYMHWYQQKPGKAPKLLIYLASNLESGVPSRFSGSG

SGTDFTLTISSLQPEDFATYYCQHSRELPYTFGQGTKLEIKR
``` hu36-CDRH1:
(SEQ ID NO: 7)
ENIIH hu36-CDRH2:
(SEQ ID NO: 8)
WFHPGSGSIKYNEKFKD hu36-CDRH3:
(SEQ ID NO: 9)
HGGTGRGAMDY hu36-CDRL1:
(SEQ ID NO: 10)
RASKSVSTSAYSYMH hu36-CDRL2:
(SEQ ID NO: 11)
LASNLES hu36-CDRL3:
(SEQ ID NO: 12)
QHSRELPYT

```
Parameters of the full hu36-IgG are as follows:
Total length of full-length IgG (aa): 1,334
Calculated molecular mass of full-length IgG: 145,922
Calculated extinction coefficient of full-length IgG: 209,420
Abs 0.1% (=g/l)              1.435
theoretical pI:              8.60
potential glycosylation site: N297
```

Figure 2A:
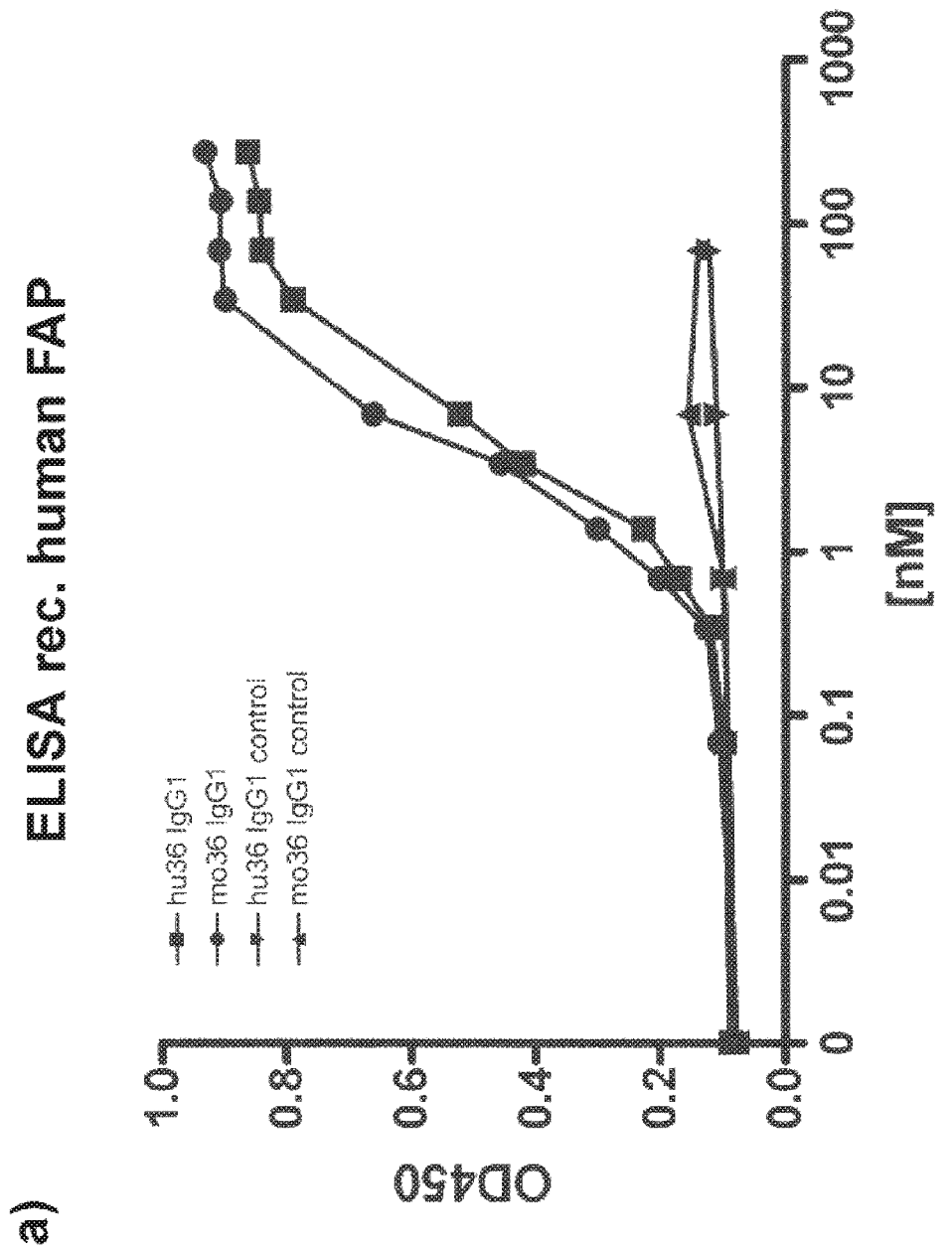
FIGS. 2A and 2B show ELISA of anti-FAP mo36-IgG1 (circles) and hu36-IgG1 (squares) for binding to recombinant human FAP (rhFAP) or control protein (BSA) (triangles and inverted triangles, respectively) (FIG. 2A). 50 ng protein were coated per well. Bound antibodies were detected with HRP-conjugated anti-human IgG-Fc. Flow cytometry analysis of anti-FAP mo36-IgG1 (triangles and stars) and hu36-IgG1 (squares and circles) for binding to HT1080-FAP (FIG. 2B). Bound proteins were detected with a PE-labeled anti-hu IgG-Fc antibody.
Figure 2B:
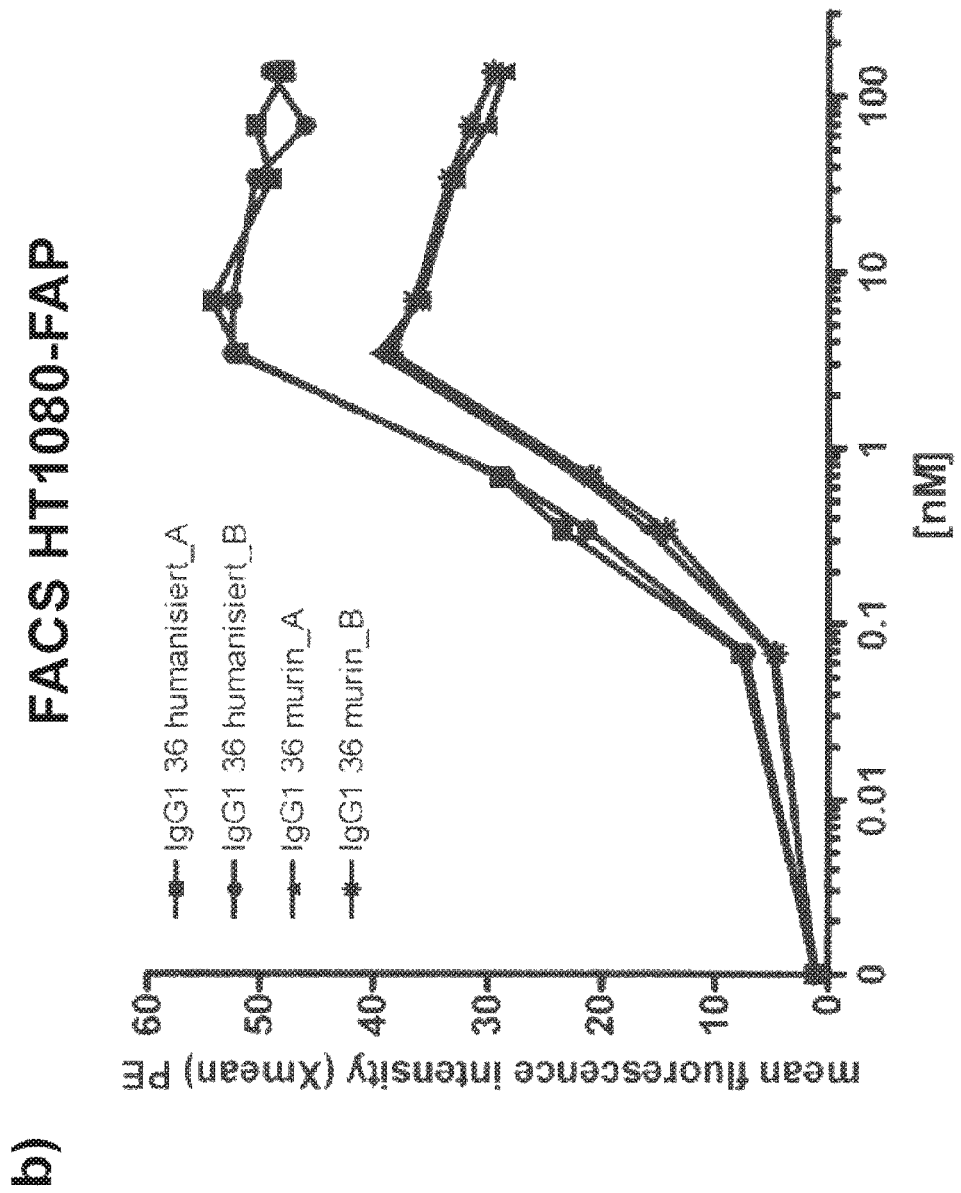
Figure 3A:
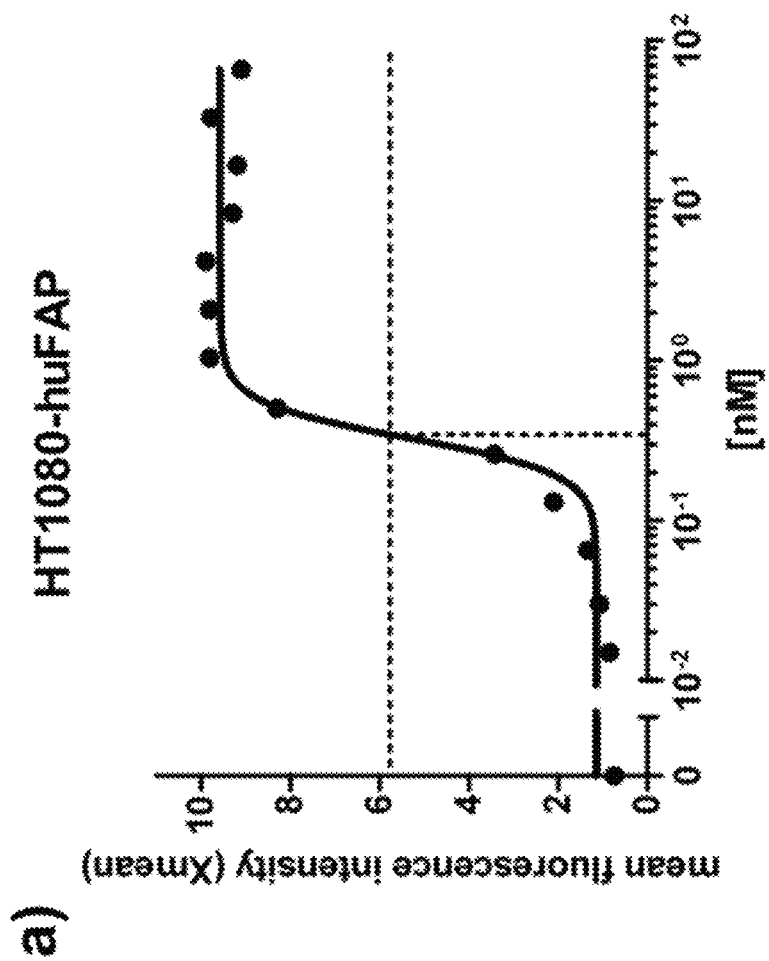
FIGS. 3A and 3B show flow cytometry analysis of binding of hu36-IgG1 to stably transfected HT1080 to express human FAP (HT1080-huFAP) (FIG. 3A) and mouse FAP (HT1080-moFAP) (FIG. 3B). Bound antibodies were detected with a PE-labeled anti-human Fc antibody.
Figure 3B:
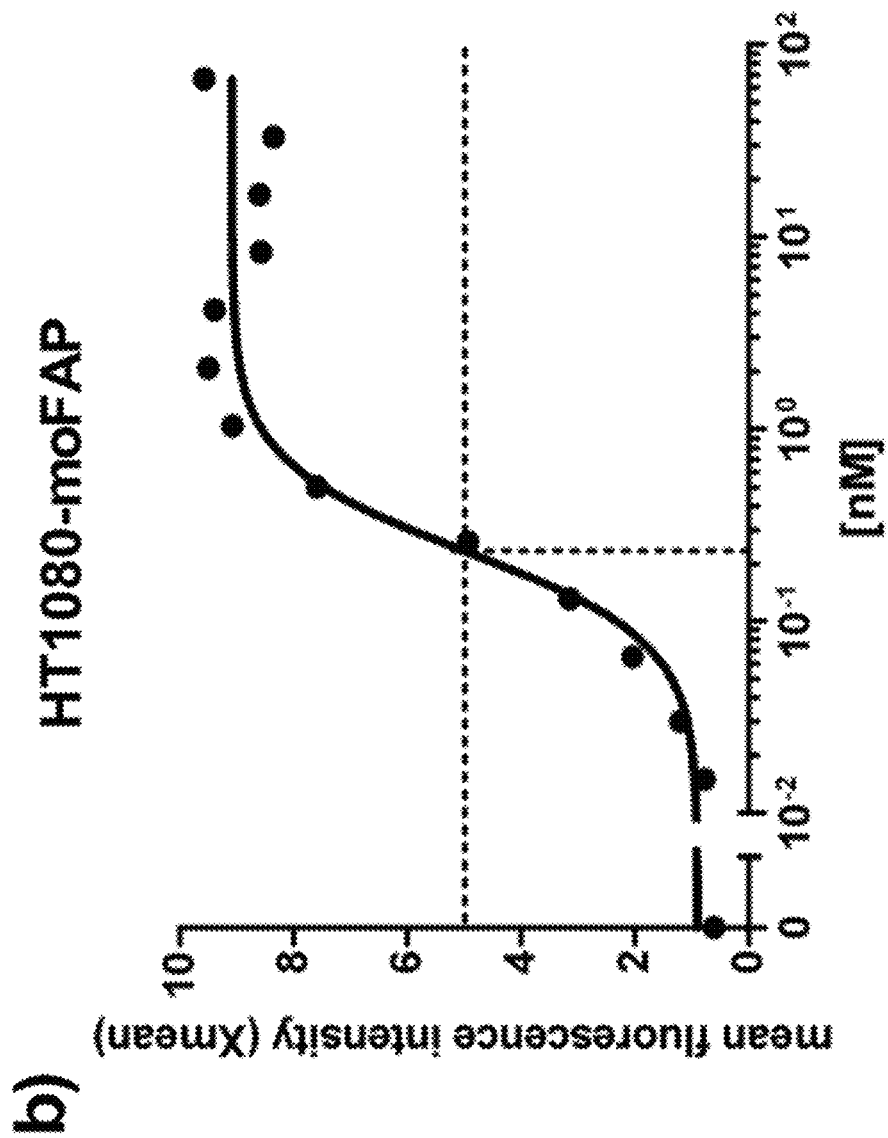

Purified chimeric and human anti-FAP antibodies mo36 and hu36 were analyzed in ELISA for binding to recombinant FAP. Both anti-FAP antibodies showed specific and strong binding to recombinant FAP with similar $EC_{50}$ values (around 5 nM) (FIG. 2A). Furthermore, both antibodies showed binding to HTP1080-FAP expressing human FAP on their cell surface (FIG. 2B). The humanized IgG gave stronger signals compared with the chimeric IgG, however, with similar $EC_{50}$ values. The humanized hu36 anti-FAP antibody was able to cross-react to both human and murine FAP as shown by FACS analysis (FIGS. 3A and 3B). Hu36-IgG1 bound in a concentration-dependent manner to both cell lines with subnanomolar EC50 values (0.33 and 0.25 nM).

For scale-up the antibody constructs were cloned in GS double vectors (pEE14.4). The DNA plasmids were transformed, amplified, and transiently transfected into CHOK1SV cells for expression evaluation at a volume of 200 ml. In a second step the antibodies were transiently expressed in 5-10 L large scale cultures. Clarified culture supernatant was purified using one-step Protein A chromatography. Product quality analysis through SE-HPLC, SDS-PAGE and LAL was carried out using purified material at a concentration of 1 mg/ml, alongside an in-house human antibody as a control sample.

The purified protein samples were filtered through a 0.2 µm filter and analysed by SE-HPLC chromatograms. The antibodies were purified to >98.8%. The endotoxin levels were <0.5 EU/mg.

All purified proteins were analyzed by SDS-PAGE in reducing and non-reducing conditions (data not shown).

Purified proteins hu36-IgG and mu36-IgG were characterized by SDS-PAGE and size exclusion chromatography. Bioactivity was analyzed by ELISA, using recombinant FAP and detection of bound antibodies with HRP-conjugated anti-human IgG antibodies. Cell binding was analyzed by flow cytometry, using HT1080-FAP cell line. Melting points were determined by dynamic light scattering using a zetasizer nano. Affinities were determined by QCM using an Attana A100. Internalization study was performed by indirect immunofluorescence confocal microscopy on permeabilized cells, detecting bound and internalized antibodies with a FITC-labeled secondary antibody.

The full-length IgG1 purified antibodies were successfully produced at both lab scale and large scale, for the generation of immunoconjugates. A summary of antibody properties is shown in Table 2. The antibodies retained their specificity, as shown by ELISA and flow cytometry experiments. The antibodies bound FAP-expressing cells with subnanomolar $EC_{50}$ values. Affinities, as determined by QCM, were comparable with that of parental antibodies. QCM measurements indicated the contribution of avidity effects to high-affinity binding. Thermal stability differed between the different IgGs (77-80° C.)

Figure 4:
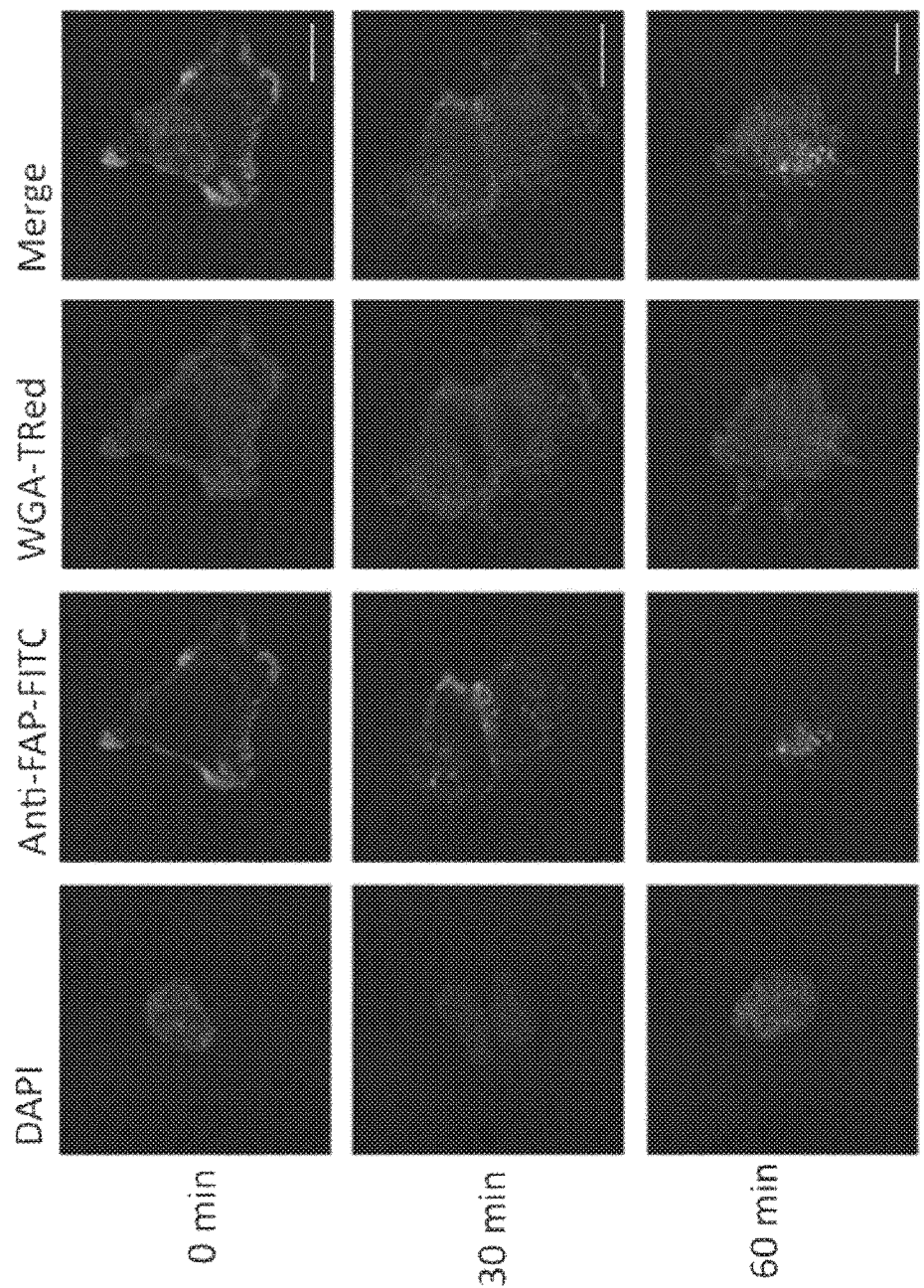
FIG. 4 shows confocal microscopy of HT1080-FAP cells, incubated with hu36-IgG1 for various times (0, 30 and 60 mins) and stained with FITC-labelled anti-IgG antibody, WGA-TRed (membrane staining), and DAPI (nucleus). The right-hand panels show a merged image of the three stains.
Figure 5:
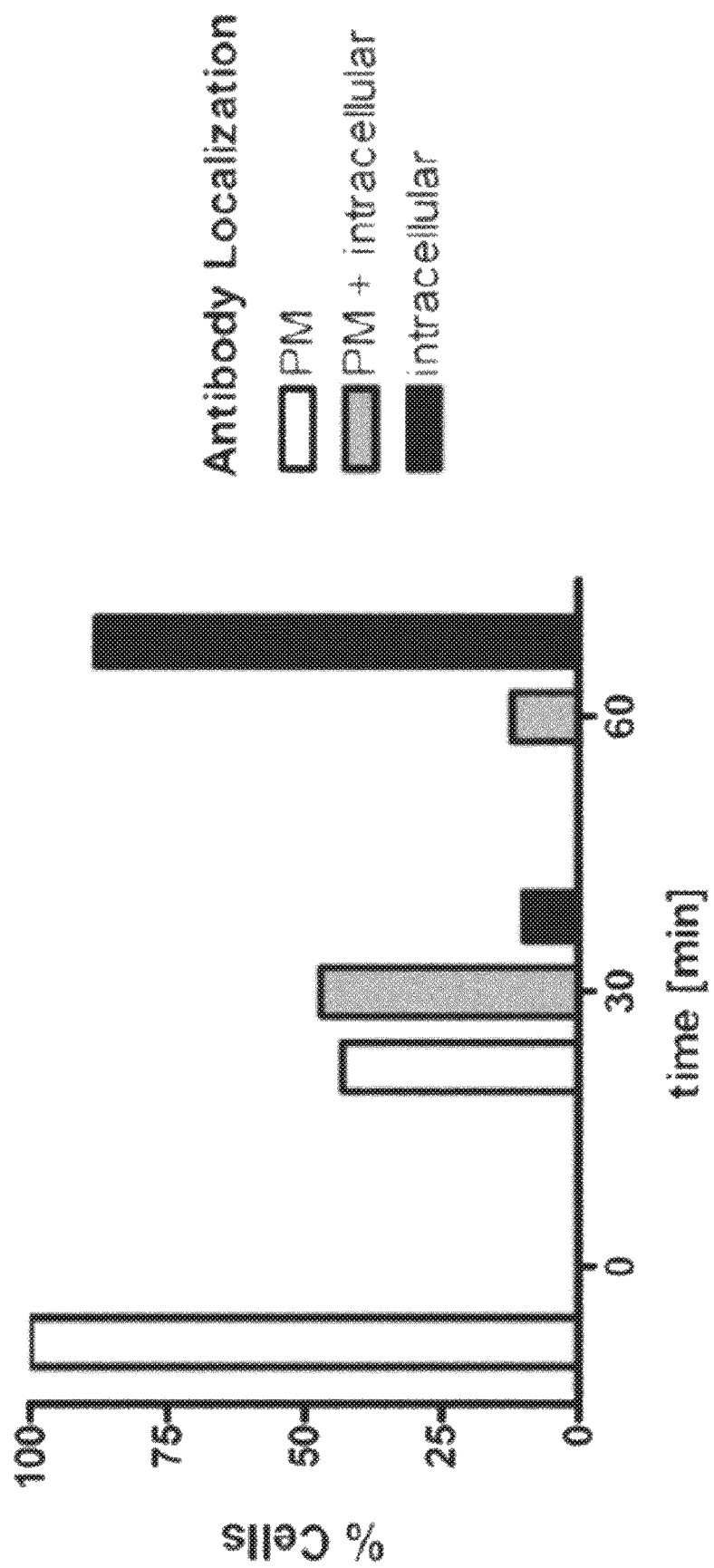
FIG. 5 shows analysis of internalization of hu36-IgG1 by discrimination of cells (n=10-30) showing only membrane staining (PM; open bars), PM and intracellular staining (shaded bars), or only intracellular staining (filled bars). A clear time-dependent internalization is evidenced.
Figure 6:
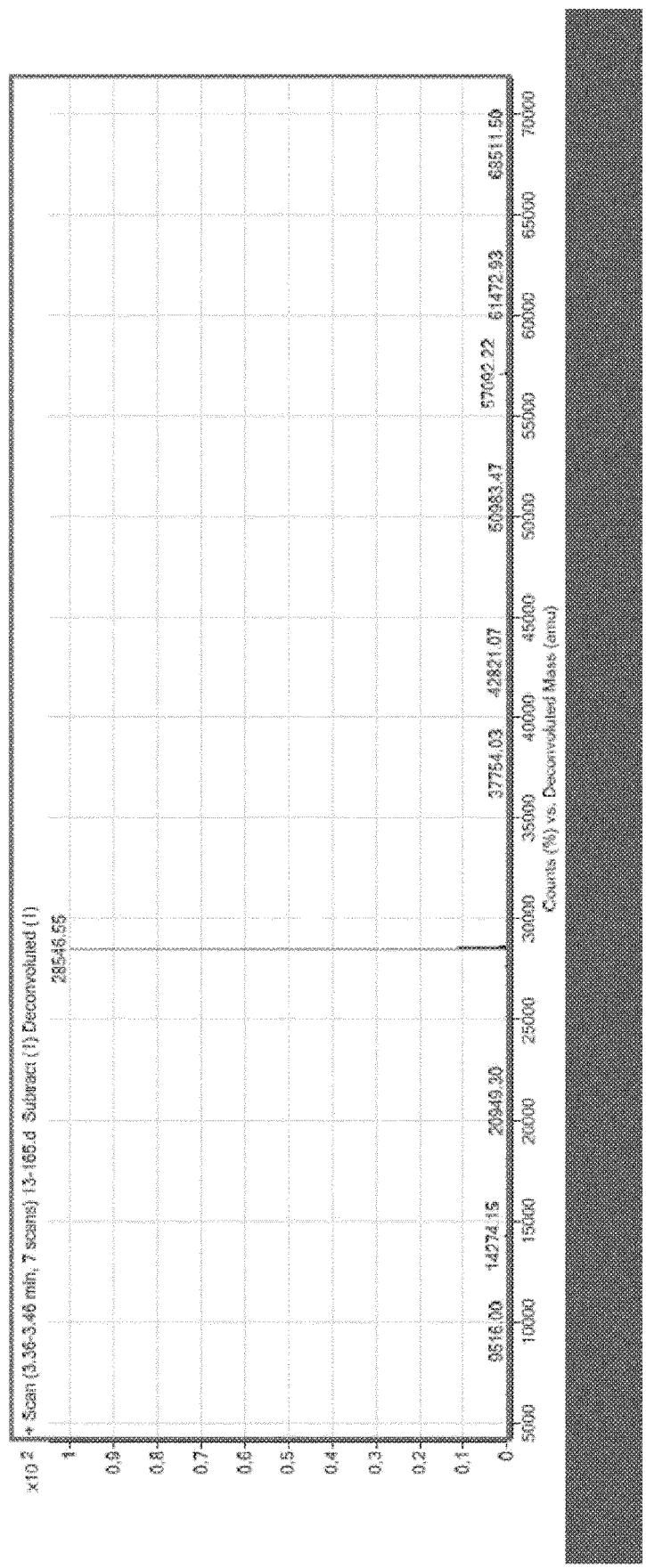
FIG. 6 shows MALDI-Tof profile of recombinant nigrin-b A-chain. Observed mass (Da): 28546.55; Expected mass (Da): 28546.09; Mass deviation: 0.5; Mass Accuracy: 16 ppm.
Figure 7:
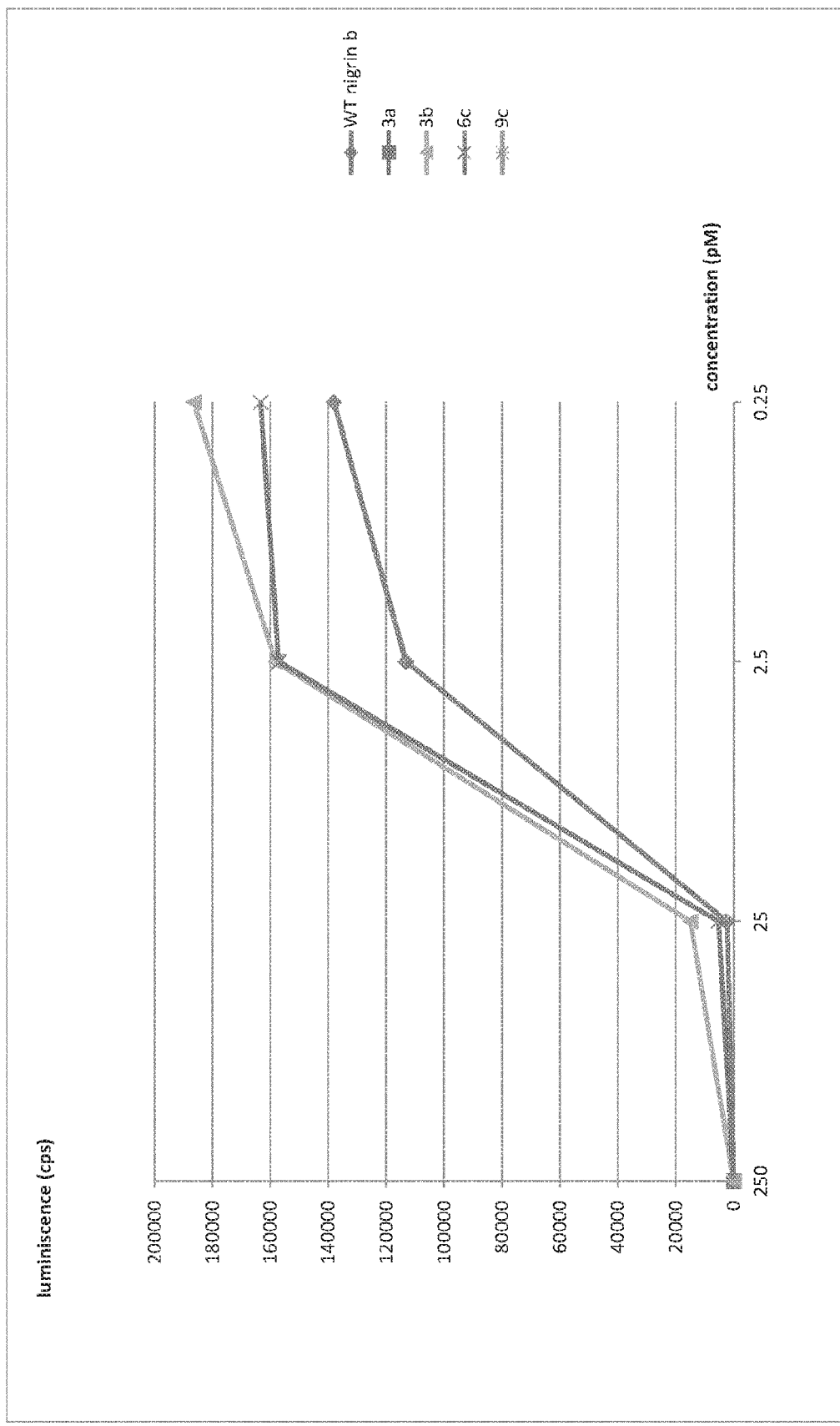
FIG. 7 shows ribosome inactivating protein (RIP) activity of recombinant Nigrin-b A-chain (recNgA) tested in rabbit reticulocyte cell-free lysates (RRL) versus native (WT) Nigrin-b. (3a, 3b, 6c, 9c) represent different formulations of recNgA.

Rapid internalisation was shown for hu36-IgG1 (humanized anti-FAP antibody) on HT1080-FAP cells (see FIGS. 4 and 5).

TABLE 2

Summary of antibody properties

| antibody | mo36-IgG1 | hu36-IgG1 |
|---|---|---|
| antigen | hu and mo FAP | hu and mo FAP |
| isotype | γ1*/κ | γ1*/κ |
| IgG type | chimeric | humanized |
| plasmid | OCMTX001p | OCMTX002p |
| purity (SEC) | minor aggregates | ✓ |
| Tm (DLS) | 77° C. | 80° C. |
| $EC_{50}$ ELISA | 3 nM (rhFAP) | 3 nM (rhFAP) |
| $EC_{50}$ FACS | 0.5 nM (HT1080-huFAP) | 0.3 nM (HT1080-huFAP) 0.2 nM (HT1080-moFAP) |
| binding to primary tumor fibroblasts | n.d. | + |
| binding constants $K_D$ (QCM) | rhFAP: $K_D1 = 112$ nM $K_D2 = 0.6$ nM | rhFAP: $K_D1 = 218$ nM $K_D2 = 0.4$ nM |
| internalization | n.d. | HT1080-FAP 30-60 min |

γ1* = deficient for ADCC and CDC (see Amour et al., 1999; Richter et al., 2013).

Anti-FAP IgG1 In Vivo Binding.

Figure 12:
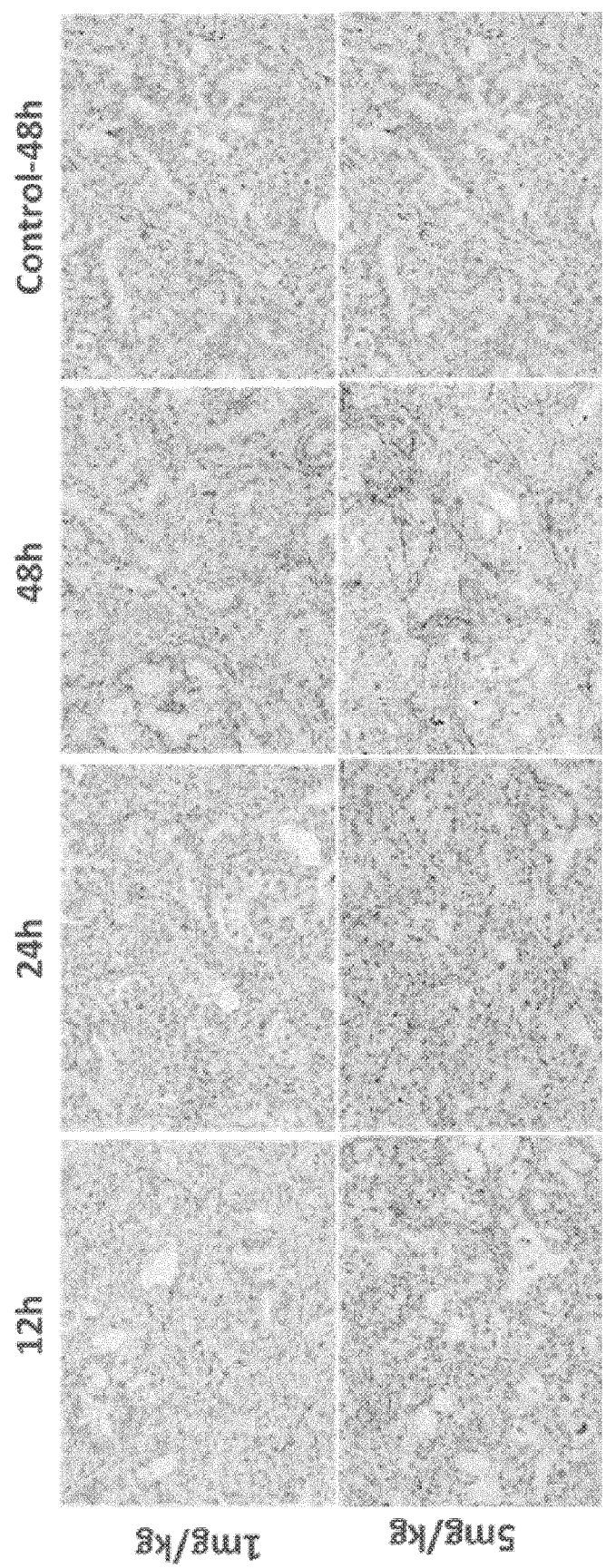
FIG. 12 shows immunodetection of anti-FAP hu36 tumour sections of patient-derived xenograft (PDX) mice (pancreatic tumour). Specific Dose- and Time-dependent staining of stroma is observed in subcutaneous tumors from PDX mouse model for pancreas cancer (Panc185)—Single dose (1 & 5 mg/kg) of anti-hu/moFAP hu36 IgG1 was administrated intraperitoneally in PDX mice Panc-185; immunodetection was performed with an anti-human IgG1 secondary antibody—20× scale pictures are shown. Control-48 h: Mice administrated with Vehicle and tumors excised after 48 h.

Anti-FAP IgG1 hu36 was administrated intraperitoneally to patient-derived xenograft mice for pancreas cancer at a single dose of 1 and 5 mg/kg. Tumors were excised after 12, 24, and 48 h administration, formalin-fixed and paraffin-embedded. Immunodetection of anti-FAP hu36 was performed with an anti-human IgG secondary antibody. FIG. 12 shows the specific dose- and time-dependent staining of stroma, only in tumor samples from treated mice.

Example 3—Nigrin-b A-Chain

In order to avoid side effects of free toxin that could be released in the bloodstream and to reduce potential immunogenicity of the RIP toxin, as extensively described with ricin, the enzymatic domain of Nigrin b, the A chain, was cloned and expressed in bacteria. The present inventors hypothesized that, if the A chain produced in bacteria was able to retain its activity, it would not be able to enter the cells, unless conjugated to a vehicle molecule, such as an antibody.

Production

Nigrin-b A-chain was synthetized taking into account codon optimization for bacterial expression and the synthetized gene was cloned in two different vectors, Nigrin_pET30b-3 and Nigrin_pET33b-1 (+/−His tag) for expression in two different E. coli strains, E. coli BLR(DE3) and E. coli HMS174(DE3). Different culture media were used to check different expression conditions. Process purification was established using Capto Q chromatography and SP Sepharose High Performance. Purified recombinant Nigrin-b A-chain (recNgA) was formulated at 5 mg/ml in PBS 1× pH7.4, DTT 0.5 mM, glycerol 10%. Endotoxin levels were <1 EU/mg of Nigrin and the purity >99% in monomeric form.

Eldman N-terminal sequencing revealed that N-terminal end of recNgA corresponded to the expected sequence.

Recombinant Nigrin-b A-chain amino acid sequence:
(SEQ ID NO: 13)
MIDYPSVSFNLDGAKSATYRDFLSNLRKTVATGTYEVNGLPVLRRESEVQ

VKSRFVLVPLTNYNGNTVTLAVDVTNLYVVAFSGNANSYFFKDATEVQKS

NLFVGTKQNTLSFTGNYDNLETAANTRRESIELGPSPLDGAITSLYHGDS

VARSLLVVIQMVSEAARFRYIEQEVRRSLQQATSFTPNALMLSMENNWSS

MSLEIQQAGNNVSPFFGTVQLLNYDHTHRLVDNFEELYKITGIAILLFRC

SSPSND

The recombinant Nigrin-b A-chain has the following characteristics:
Number of amino acids: 256
Molecular weight: 28546.0
Theoretical pI: 5.45
The nucleotide sequence encoding recombinant Nigrin-b A-chain is as follows:

(SEQ ID NO: 14)
```
atagactatc cctccgtctc cttcaacttg gatggagcca agtcggctac atacagggac ttcctcagca acctgcgaaa aacagtggca actggcacct atgaagtaaa cggtttacca gtactgaggc gcgaaagtga agtacaggtc aagagtcggt tcgttctcgt ccctctcacc aattacaatg gaaacaccgt cacgttggca gtagatgtga ccaaccttta cgtggtggct tttagtggaa atgcaaactc ctactttttc aaggacgcta cggaagttca aaagagtaat ttattcgttg gcaccaagca aaatacgtta tccttcacgg gtaattatga caaccttgag actgcggcga atactaggag ggagtctatc gaactgggac ccagtccgct agatggagcc attacaagtt tgtatcatgg tgatagcgta gcccgatctc tcctttgtggt aattcagatg gtctcggaag cggcaaggtt cagatacatt gagcaagaag tgcgccgaag cctacagcag gctacaagct tcacaccaaa tgctttgatg ctgagcatgg agaacaactg gtcgtctatg tccttggaga tccagcaggc gggaaataat gtatcaccct tctttgggac cgttcagctt ctaaattacg atcacactca ccgcctagtt
```

-continued

```
gacaactttg aggaactcta taagattacg gggatagcaa ttcttctctt ccgttgctcc tcaccaagca atgat
```

Materials

Nigrin_pET30b-3 genetic construct.

*Escherichia coli* (Migula) Castellani and Palmers BLR (DE3)

Culture media: auto induced medium (AIM)

Extraction culture buffer: Glycine/NaOH 10 mM, Leupeptine 1 μg/ml, Pepstatine 1 μg/ml, pH 9.5.

Extraction supernatant buffer Tris-HCl 50 mM, NaCl 200 mM, $MgCl_2$ 2 mM, leupeptine 1 $\mu g ml^{-1}$, pepstatine 1 $\mu g ml^{-1}$, lysozyme 0.1 $mg ml^{-1}$, pH8.0.

Dialysis solution: Citric acid/NaOH 25 mM pH5.0. -Capto Q FPLC: Equilibration buffer A: Glycine/NaOH 50 mM pH9.5. Elution buffer B: Glycine/NaOH 50 mM pH9.5, NaCl 1 M.

Pooled fractions from Capto Q step (+80 ml extraction).

SP Sepharose HP FPLC: Equilibration buffer A: Citric acid 25 mM pH4.0.Elution buffer B: Citric acid 25 mM pH4.0, NaCl 1 M.

Methods

*E. coli* BLR(DE3) holding expression Nigrin_pET30b-3 cultivated in 1 L format of Auto Inducible Medium (AIM) with 30 $\mu g ml^{-1}$ Kanamycin. Protein expression was triggered by lactose activation and glucose depletion after about 3-4 hours of growth. Then, the temperature was lowered to 20° C. for an overnight duration.

For extraction, each cell pellet was initially resuspended in 80 ml of extraction buffer per liter of culture, and 3 cycles of 7 minutes disintegration at 1100-110 Bar were performed after 30 minutes of incubation at 8° C. under shaking. Then the extract underwent 60 minutes centrifugation at 15,900 g, 8° C. The supernatant was the purification's starting material.

Capto Q FPLC: 160 ml of extracted product from 81 culture were loaded into 160 ml Capto Q and equilibrated using 4CV of equilibration buffer and washed with 15 CV of equilibration buffer. Elution was carried in three steps: 15 CV at 1.5 mS/cm (7.6% B); 20 CV at 23.8 mS/cm (18.9% B); 20 CV 100% B.

Dialysis was performed at the following conditions: 650 ml of the product were dialyzed in 4×5Lbathsin in citric acid/NaOH 25 mM pH5.0, cut-off 6-8000 Da. Dialysis factor 3500, <24 h. After dialysis, a 30 minutes centrifugation at 20,500 g and 8° C. allowed to separate soluble from insoluble fractions. SDS-PAGE was performed on the total and soluble fractions both pre and post dialysis (10 μl loaded on SDS-PAGE). The eluent was dialysed into PBS pH7.4 and filtered T=0.22 μm using 2×20 $cm^2$ EKV filters.

SP Sepharose HP: 610 ml of dialyzed pool of Capto Q in Citric acid 25 mM pH5.0 were loaded into 240 ml SP Sepharose High Performance with 4 CV of equilibration buffer and washed with 15CV of equilibration buffer and eluted at 25 Cv gradient to 20% B; 4 CV step of 100% B.

Pooled fractions from SP Sepharose HP step were dialysed in PBS pH7.4, DTT 0.5 mM (5×4 L baths, pooled fractions of 950 mL at 0.97 mg/ml). Cut off was 6-8000 Da, dialysis factor was ~3130, time >24 h. Afterwards a 30 min centrifugation at 20,55 g and 8° C. allowed to separate soluble from insoluble fractions. 10% glycerol was added afterwards.

Finally the eluent was dialysed into PBS pH7.4 (5 baths ~3100) and filtered φ=0.2 μm, then the recNg b A batch was snap frozen at −80° C. A SEC in Semi-Preparative 5200 Superdex was later carried out.

Size exclusion chromatography and mass spectrometry analysis demonstrated monomeric and purification status of the obtained recombinant nigrin-b A-chain (recNgA) (FIG. 6).

Stability studies were performed to evaluate pH and temperature effect on nigrin-b A-chain protein itself and its activity. recNgA is stable at pH ranging from 5 to 9, and in presence or not of glycerol (from 10 to 45%) (data not shown).

Activity

The ribosome-inactivating protein (RIP) activity of recombinant Nigrin-b A-chain was tested in rabbit reticulocyte cell-free lysates: $IC_{50}$ value obtained was similar to native nigrin-b and within 2.5 to 25 pM range (see FIG. 7). Thus, the A chain from Nigrin-b, expressed as a recombinant protein in bacteria, maintains its enzymatic activity, supporting that glycosylation is not required for RIP activity of Nigrin-b A-chain.

RecNgA retains its activity in rabbit reticulocyte cell-free lysates if stored frozen at (−80° C.) and below 3 freeze-thaw cycles (not shown).

The cytotoxic activity of recNgA was tested on cell cultures through crystal violet-based viability assay. recNgA, lacking the B chain to translocate within cells, presents a 100 to 1000 less toxic activity than native Nigrin-b, as shown in FIG. 8. Native nigrin b showed an $IC_{50}\approx 2\times 10^{-8}$M (similar to previous published data; see 33), while recNgA showed an $IC_{50}\approx 2\times 10^{-6}$M.

Previously published studies showed that native Nigrin b presents higher RIP activity than Ricin in RRL assay, while it is much less toxic (30-10,000 time, approximately) in cells or in vivo (see $IC_{50}$ and $LD_{50}$ values in Table 3).

Upon removing of B chain, Ricin A chain loses activity in both RRL assay and cytotoxicity assay. Unexpectedly, Nigrin b A chain, generated for the first time in this present invention, only loses activity in cell cytotoxicity assay, while it was even increased in RRL assay with respect to native Nigrin b. These data were suggesting that, in the case of Ricin, removing B chain was affecting not only binding and translocation of A chain, but also its RIP activity, while this was not the case for Nigrin b A chain that retains and even increases its RRL activity with respect to its native counterpart. As a result, Nigrin b A chain is 50 times more active than the Ricin A chain in RRL.

Consequently, upon conjugation, Nigrin b A chain conjugates present higher cytotoxic activity ($IC_{50}$ within pM range) than Ricin A chain conjugates (nM range) (data not shown).

TABLE 3

In vitro and in vivo activity data for Ricin and Nigrin (native and A chain).

| | Rabbit Lysate $IC_{50}$ (pM) | HeLa Cells $IC_{50}$ (pM) | Mouse $LD_{50}$ ($\mu g kg^{-1}$) |
|---|---|---|---|
| Nigrin b | 30 | 27,600.00 (20-2300 nM; dpt cell line) | 12,000.00 |
| Nigrin b A chain | 6.5 | 750,000.00 (HT1080-FAP) 300,000.00 (HT1080) | ND |
| Ricin | 100 | 0.67 | 3.00 |
| Ricin A chain | 300 | 260,000.00 (T cells) | ND |

(Inventors' Own data - Nigrin b A chain; see also Ferreras J. M. et al., Toxins, 3: 420, 2011; Svinth M. et al., BBRC, 249: 637, 1998)

Example 4—Conjugation of Nigrin-b A-Chain to Anti-FAP Antibodies

For immunoconjugates containing RIPs to exhibit maximal cytotoxicity the RIP must be released from the targeting vehicle in fully active form, which requires avoiding steric hindrance (34)). The disulfide bond is the only type of linkage that fit this criterium (35, 36). This bond allows conjugation using reagents for the introduction of free sulfhydryl groups such as N-succynimidyl 3(2-pyridyl-dithiopropionate) (SPDP) and 4-succynimidyloxycarbonyl-α-methyl-α (2-pyridyl-dithio)toluene (SMPT). Immunotoxins consisting of mAbs covalently bound to toxins by hindered disulfide linkers, often labeled as second generation immunotoxins, are stable, long lived and display potent cytotoxicity to target cells (37).

SPDP has already been used in the making of immunotoxins (ITs) containing nigrin b (38, 39). Moreover SMPT protects the disulfide bond from attack by thiolate anions, improving in vivo stability of the linkage (40, 41).

Material
Recombinant nigrin b A chain in PBS, pH7.4, 10% glycerol, 0,5 mM DTT, 4.92 $gl^{-1}$, stored at 5° C.
- 5,5'-dithio-bis-(2-nitrobenzoic acid)
- GE PD MiniTrap G-10 desalting columns.
- 0.2 μm 28 mm sterile Minisart filters.
- Sciclone ALH 3000 workstation.
- Sarstedt Microtest Plate 96-Well Flat Bottom, ref n° 82.1581.

Methods

Dithiothreitol (DTT, Cleland's reagent) is a redox agent that will be used to free the thiol groups present in the protein sample. Once said groups have been freed and so are available for reacting 5,5'-dithio-bis-(2-nitrobenzoic acid) (Ellman reagent) will be added. Ellman reagent disulphide bridge will be cleaved and the 2 resulting thio-nitrobenzoate molecules (TNB) will attach to the protein at the thiol group sites. To titrate the TNBs absorbance values will be taken at λ=412 nm, a wavelength at which DTT is not absorbed, rendering the concentration of thiol groups. The proportion of these with the concentration of the protein taken from its absorbance at λ=280 will yield the number of free thiol groups per protein molecule.

Direct thiol titration was performed as follows: 204 μl recNg b A were dissolved in 796 μl 20 mM phosphate 250 mM NaCl 1 mM EDTA pH 7.0 (assay buffer) (1.0033 $gl^{-1}$=final concentration). Ellman reagent was dissolved in phosphate 0.2 M at 3 $gl^{-1}$. For both buffers monobasic and dibasic sodium phosphate were added in a 1.61 to 1 mass proportion. PH was adjusted at room temperature and buffers were filtered. 100 ml Ellman buffer and 500 ml assay buffer were prepared. Ellman reagent was completely resuspended rather than weighed.

The recNgA sample was incubated in the presence of 4.8 mM DTT at room temperature for 30 min. The recNgbA sample was then purified in the column and the first 10 ml of the eluent aliquoted (V=0.5 ml). The $A_{280}$ of the aliquots was taken and the two most concentrated mixed. $A_{280}$ was taken again. 10 μl of 3 $gl^{-1}$ DTNB were added and $A_{412}$ measured after 2 min (n=1), using Ellman diluted in assay buffer in the same concentration as a blank ($n_b$=3). Readings belonged to the 0.1-3 AU linear range. Protein solutions were pipetted right beneath the meniscus after vortexing. 100 μl were pipetted per well. The results of this study show that the thiol group belonging to recNgA's single cysteine residue is free and available for reaction, not being blocked by its tertiary structure. This will allow recNgbA to be conjugated using a linker that requires a hindered inter-chain disulfide bond.

It is well established that immunoconjugates which contain ribosome-inactivating proteins exhibit maximal cytotoxicity only when the toxin molecule is released from the targeting vehicle in a fully active form. The separation of the RIP molecule from the carrier is required to avoid steric hindrance and to allow an effective translocation of the toxin into the cytoplasm (34)). At present, the disulfide bond is the only type of linkage which appears to fit these criteria (36).

The coupling of two different protein macromolecules, that results in heterodimer formation, requires that each protein is modified prior to mixing them to react. In the case of the A chains of type 2 RIPs, the modification is limited to the reductive cleavage of the native cysteine residue that links the active (A) and the binding (B) chains of the molecule.

For IgG molecules, this is not possible because cysteine residues are involved in maintaining the tertiary and/or quaternary structure of the protein, so that it is not possible to reduce them without loss of the specific protein functions. Moreover, presumably some of the cysteine residues are not sterically accessible, as it was demonstrated by the 10 thiols groups per immunoglobulin that had to be generated for an optimal conjugation to an activated RIP (42).

For these reasons, in most IgG molecules, thiol groups are chemically inserted using hetero-bifunctional reagents, and several methods have been developed in order to generate hetero-conjugates avoiding or reducing to a minimum the formation of homopolymers. In most cases, the reagents used to introduce thiol groups react with amino groups, forming amide or amidine bonds. Amino groups are reactive, abundant and, in a limited way for most proteins, expendable. That is, a limited number of amino groups can be modified without diminishing the biological activity of the protein (36).

The most commonly used reagents for the introduction of free sulphydryl groups are N-succinimidyl 3-(2-pyridyl-dithiopropionate) (SPDP) and 4-succynimidyloxycarbonyl-α-methyl-α-(2-pyridyl-dithio)toluene (SMPT), that introduce 2-pyridyl disulphide groups into the protein by reacting with amino groups to form neutral amides, and methyl 4-mercaptobutyrimidate (2-iminothiolane.Traut's reagent) that introduces mercaptobutyrimidoyl groups, reacting to form charged amidines, thus preserving the positive charge of the derivatized amino acid (36, 41).

SPDP and SMPT introduce hindered disulphide bond, while 2-iminothiolane —SH must be protected by reacting it with 5,5'-dithiobis-2-nitrobenzoic acid (Ellman's reagent). The reaction with Ellman's reagent is also used for the quick measurement of protein sulphydryl groups (43, 44).

SMPT has a methyl group and a benzene ring attached to the carbon atom adjacent to disulphide bond that protects it from attack by thiolate anions, thus improving the in vivo stability of the linkage (40, 41).

Based on these data, IgG proteins can be modified with SMPT, which do not significantly affect the antigen binding property of the molecules in the following conditions, even if they change the charge of the protein in the reaction site.

In the present study the inventors investigated conjugating humanized anti-FAP-IgGls with recNgA, using 2 different recNgA:mAb molar ratios of 2.5 and 3.5, after derivatization using an SMPT:mAb molar ratio of 6, following conjugation protocols (36). Purification was performed by Size Exclusion chromatography on Sephacryl 5200 (37).

Under the described conditions, the immunotoxin is predominantly a mixture of antibody linked to one or two toxin molecules, with the presence of high molecular weight components (IgG linked to several RIP proteins), as well as free and polymeric RIPs (dimeric in the case of recNgA) and free antibody. Thus, a careful purification is thought to be desirable to obtain a pure product.

Biochemical Characterization

Anti-FAP hu36-IgG1-recNgA immunotoxin conjugates were produced and characterized as follows:

Conjugate HPS131-001-1
Concentration 0.277 mg/ml
Drug:antibody ratio (DAR): 1.8
PM: 182 kDa
Purity: 87% (13% of free mAb)

In Vitro Activity Testing

Figure 9:
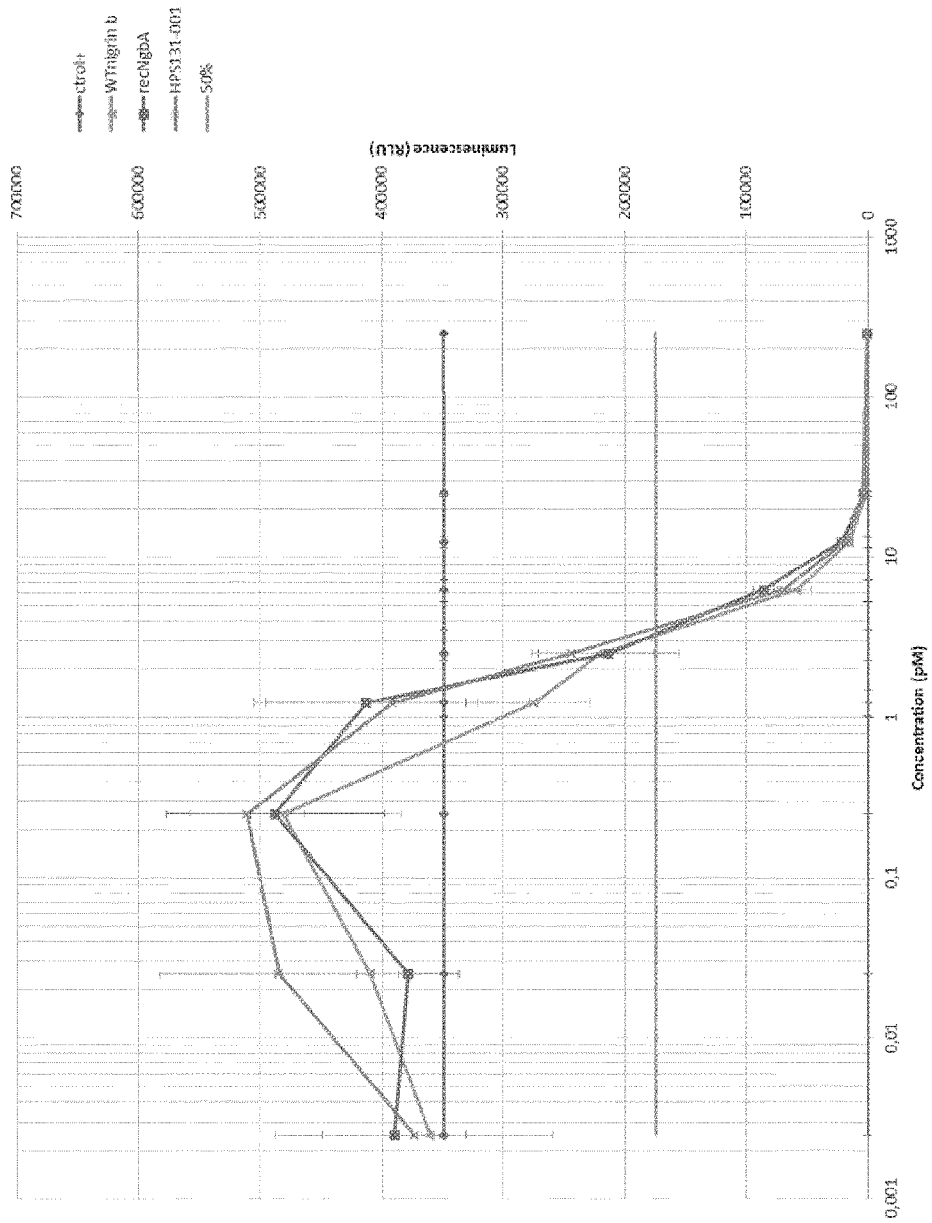
FIG. 9 shows RIP activity of anti-FAP hu36-IgG1-recNgbA immunotoxin conjugates (HSP131-001; crosses) in an RRL assay compared to native (WT) nigrin (triangles) and recombinant Nigrin-b A-chain (recNgA; squares).
Figure 10A:
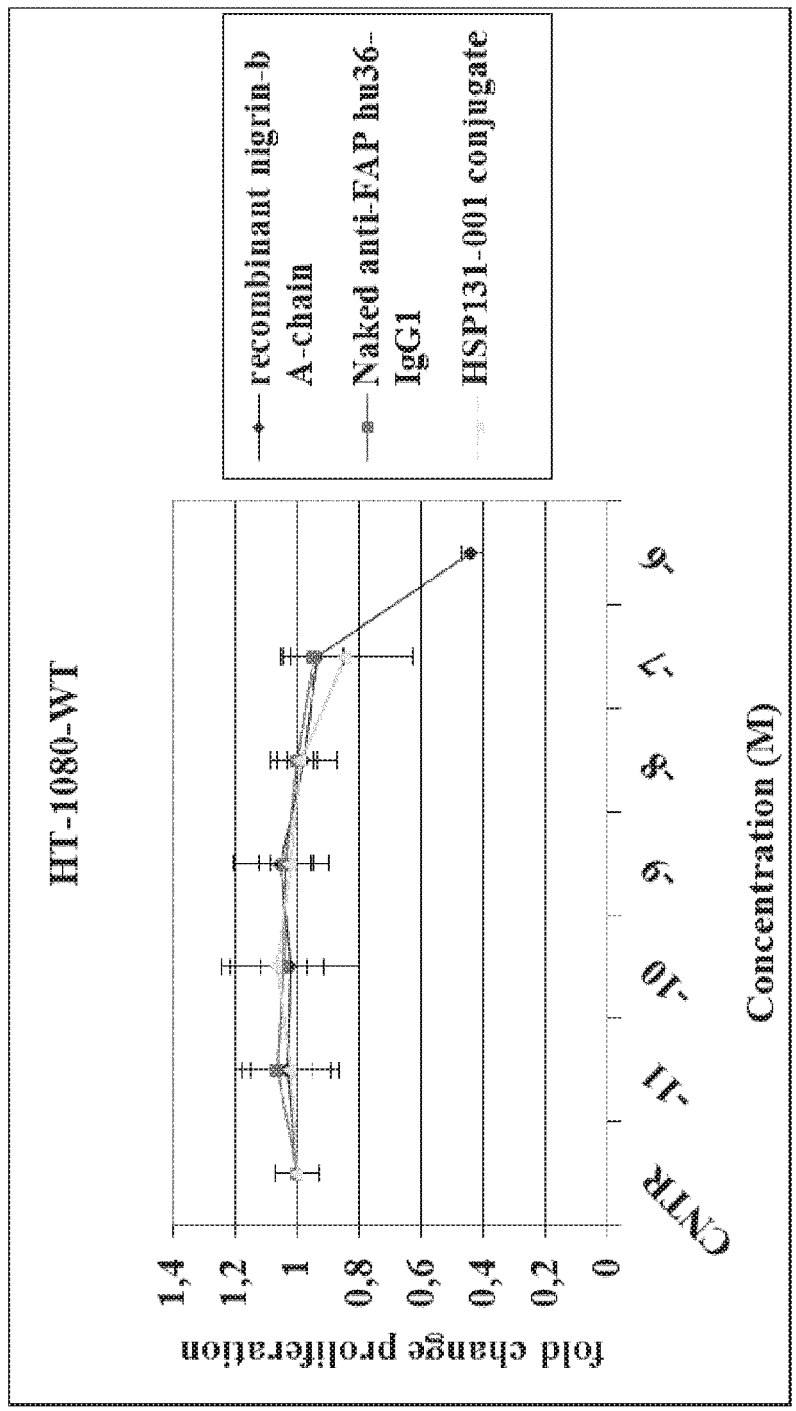
FIGS. 10A and 10B show cytotoxic activity of anti-FAP hu36-IgG1-recNgbA immunotoxin conjugates (HSP131-001; triangles), unconjugated (naked) anti-FAP hu36-IgG1 (squares) and recombinant Nigrin-b A-chain (recNgA; diamonds) on HT1080-WT cell line (FIG. 10A); and HT1080-FAP cell line (FIG. 10B). Fold-change in proliferation is plotted against antibody/immunotoxin concentration.
Figure 10B:
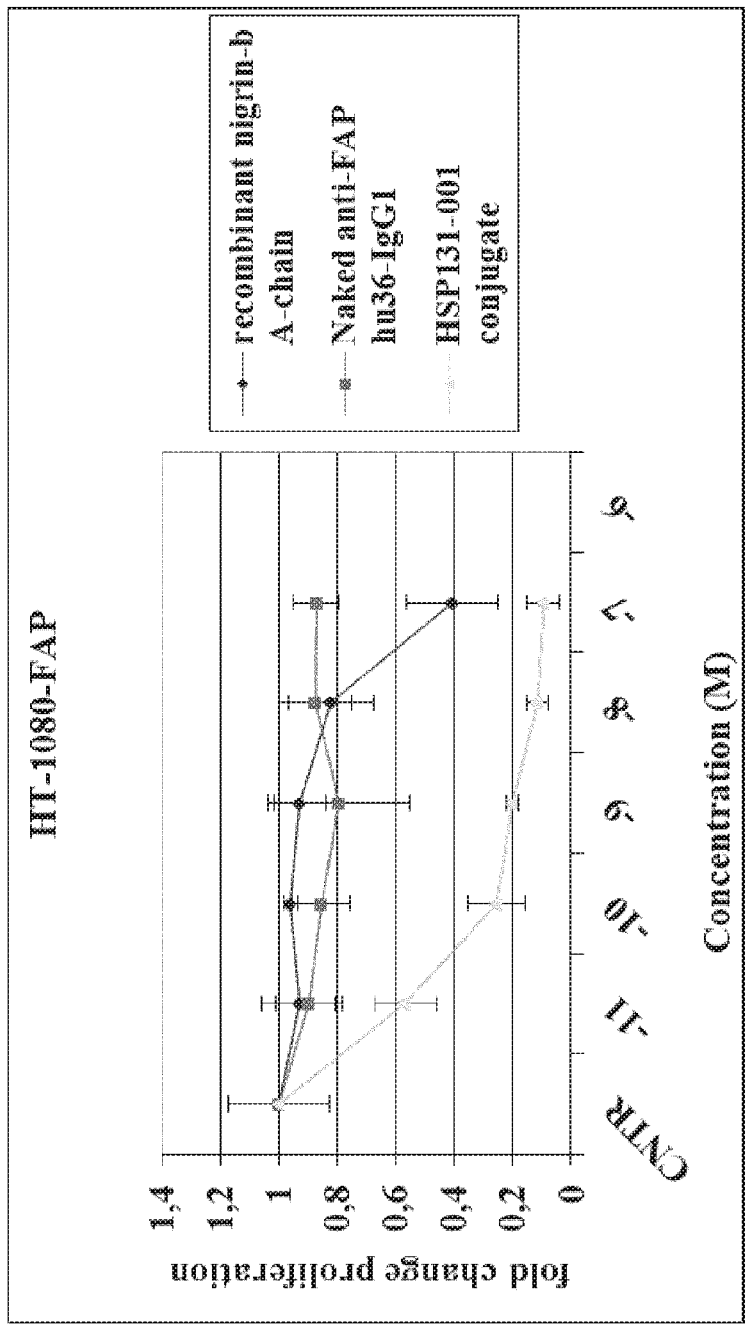

Activity testing on conjugates prepared as described above was performed though evaluation of RIP activity in rabbit reticulocyte cell-free lysate (RRL) assay (FIG. 9), and cytotoxic effect on cell cultures (FIGS. 10A and 10B).

The RRL assay results show that the anti-FAP hu36-IgG1-recNgA conjugates (HPS131-001-1) presented similar IC50 values as native Nigrin-b or recNgA and were in the 3 µM range, showing that antibody conjugation did not diminish the enzymatic activity of recNgA (see FIG. 9).

The cell cytotoxicity results show that, on HT1080 wild-type cells, conjugated antibody HPS131-001-1 displays only slight toxicity (if any) and only at highest concentration, naked anti-FAP hu36-IgG1 does not have any effect, and recNgA shows cytotoxic effect only at $10^{-6}$M and after 72 h incubation (see FIG. 10A).

However, on FAP-expressing cells, HT1080-FAP, only HPS131-001-1 conjugated anti-FAP antibodies strongly reduce HT-1080-FAP cell viability in the picomolar concentration range, with $IC_{50}$ values of 5 µM (see FIG. 10B).

Figure 8:
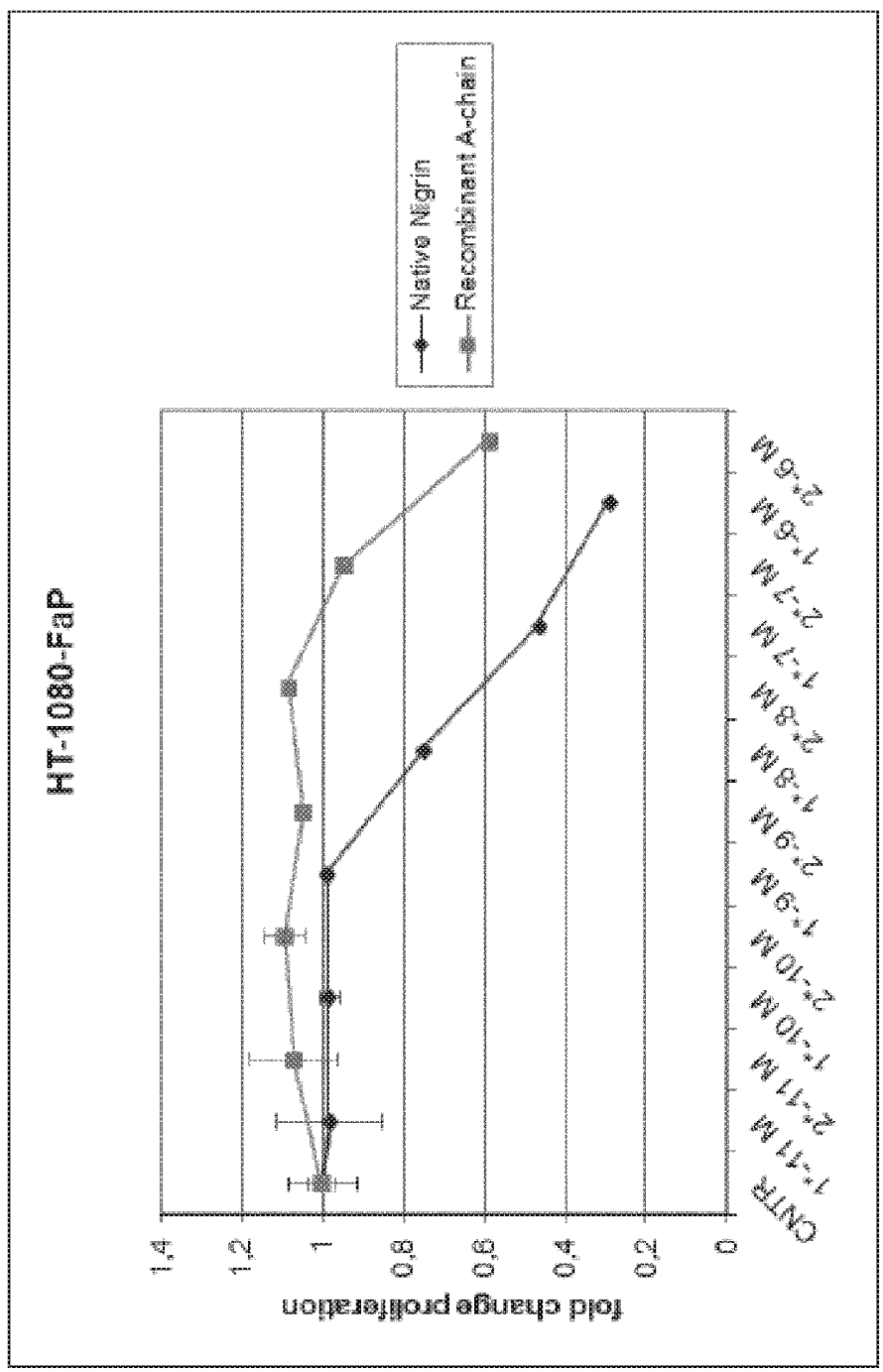
FIG. 8 shows cytotoxicity of recNgA tested on HT1080-FAP cell line through crystal violet viability assay (native Nigrin—diamonds; recombinant Nigrin-b A-chain—squares).

These results show that: 1) anti-FAP:recNgA immunotoxins are highly active in vitro, being cytotoxic at picomolar range; 2) Activity is highly specific to FAP-expression, since no significant effect was observed in HT1080-WT; 3) Anti-FAP hu36-IgG1 specificity for its target is not affected by the conjugation to recNgA, neither is the enzymatic RIP activity of recNgA; 4) Activity is specific of the conjugated anti-FAP hu36-IgG1, since no effect was observed with the naked IgG1; 5) Anti-FAP:recNgA immunotoxins are internalized, since non conjugated recNgA (lacking membrane binding domain) shows almost no cytotoxic effect ($IC_{50}$>1 µM)(see FIG. 8).

In summary, anti-FAP:recNgA immunotoxins have the ability in vitro to specifically recognize the target (FAP), to be internalized within the cytosol and release the recNgA effector moiety to actively inhibit ribosomes, resulting in cytotoxicity $IC_{50}$ values within the picomolar range.

In Vivo Evaluation of Anti-Tumoral Effect

Figure 13:
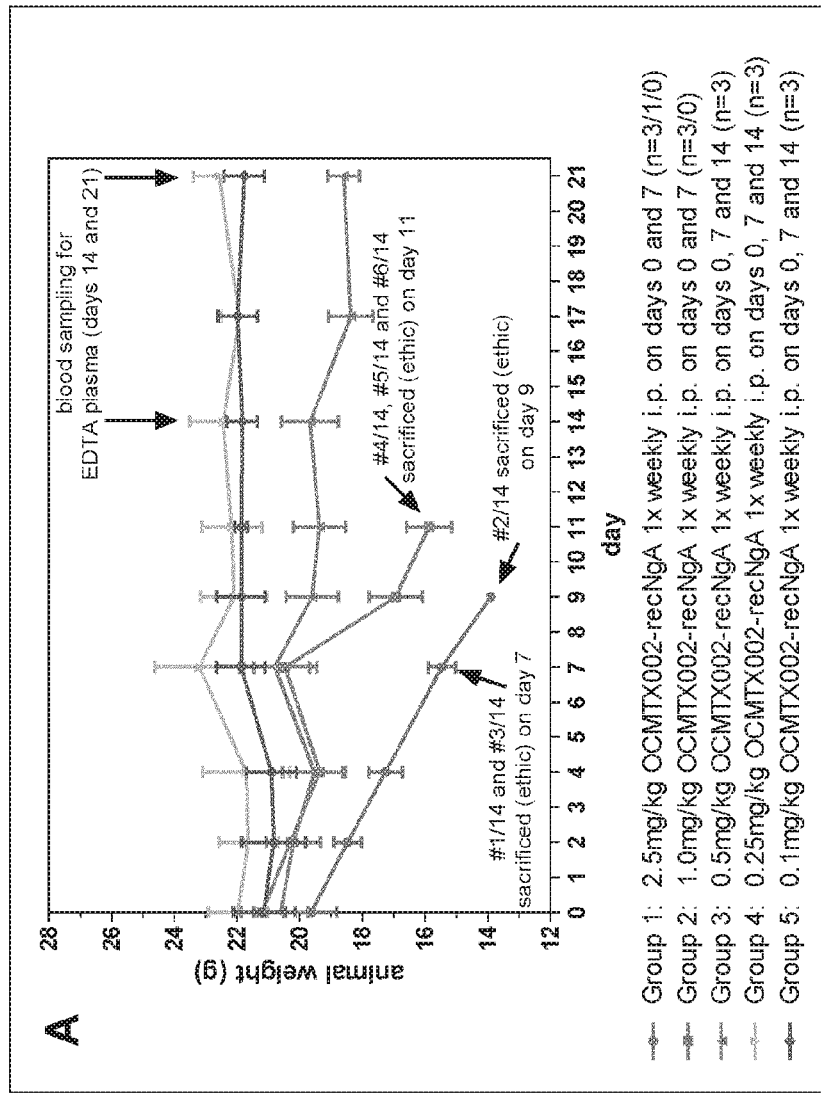
FIG. 13 shows animal weight monitored after treatment with anti-FAP:recNgA immunotoxin at different doses (2.5, 1, 0.5, 0.25, 0.1 mg/kg) administrated once a week. Significant weight loss and toxicity was observed in Group 1 and 2 (2.5 and 1 mg/kg, respectively), similarly to treatment with 5 mg/kg (not shown); 0.5 mg/kg was the highest tolerated dose when applied as single agent.

Immunotoxin anti-FAP:recNgA has been tested in vivo in both cell-derived and patient-derived xenograft mouse models for pancreas cancer. A dose range study was first performed to define the maximum tolerated dose in normal mice and each of these models: doses from 5 to 0.1 mg/kg were administrated intraperitoneally once a week during 3 weeks, and animal weight was monitored every 2 days to detect possible weight loss due to toxic effect of the immunotoxin. Results are presented in FIG. 13.

Figure 14A:
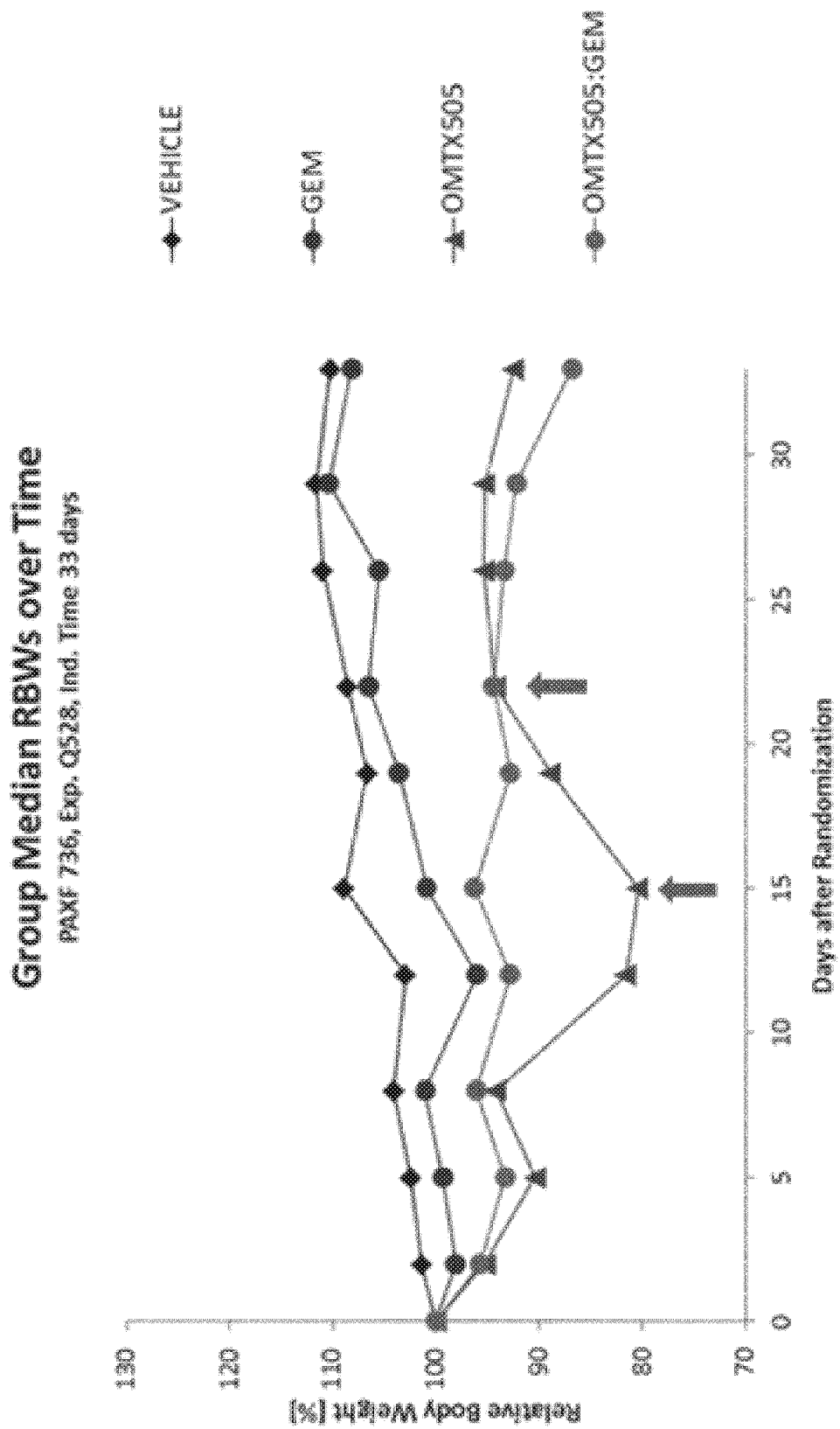
FIGS. 14A and 14B show Relative Body weight (FIG. 14A) and Tumor volume (FIG. 14B) measured from patient-derived xenograft mice (PAXF 736) untreated (Vehicle; 10 ml/kg/day; once a week), treated with Gemcitabine (GEM; 150 mg/kg; once a week), or antiFAP:recNgA immunotoxin (OMTX505; 0.5/0.25 mg/kg; once a week), or both (OMTX505 (0.25 mg/kg):GEM(150 mg/kg)), for 4 weeks (treatment days 1, 8, 15, 22, 29).

High doses (>0.5 mg/kg) induced hepatotoxicity in normal mice, while no FAP-dependent toxicity was observed after pathological analysis of uterus and skeletal muscle, where low FAP expression has been described (Dolznig H., et al., *Cancer Immun.*, 5:10, 2005; Roberts E. W., et al., *J. Exp. Med.*, 210:1137, 2013), nor in heart and kidney. Doses lower than 0.5 mg/kg did not induce any detectable non-specific toxicity in cell line-derived orthotopic (FIG. 13) and patient-derived subcutaneous (FIG. 14A) xenograft murine models of pancreas cancer.

Figure 14B:
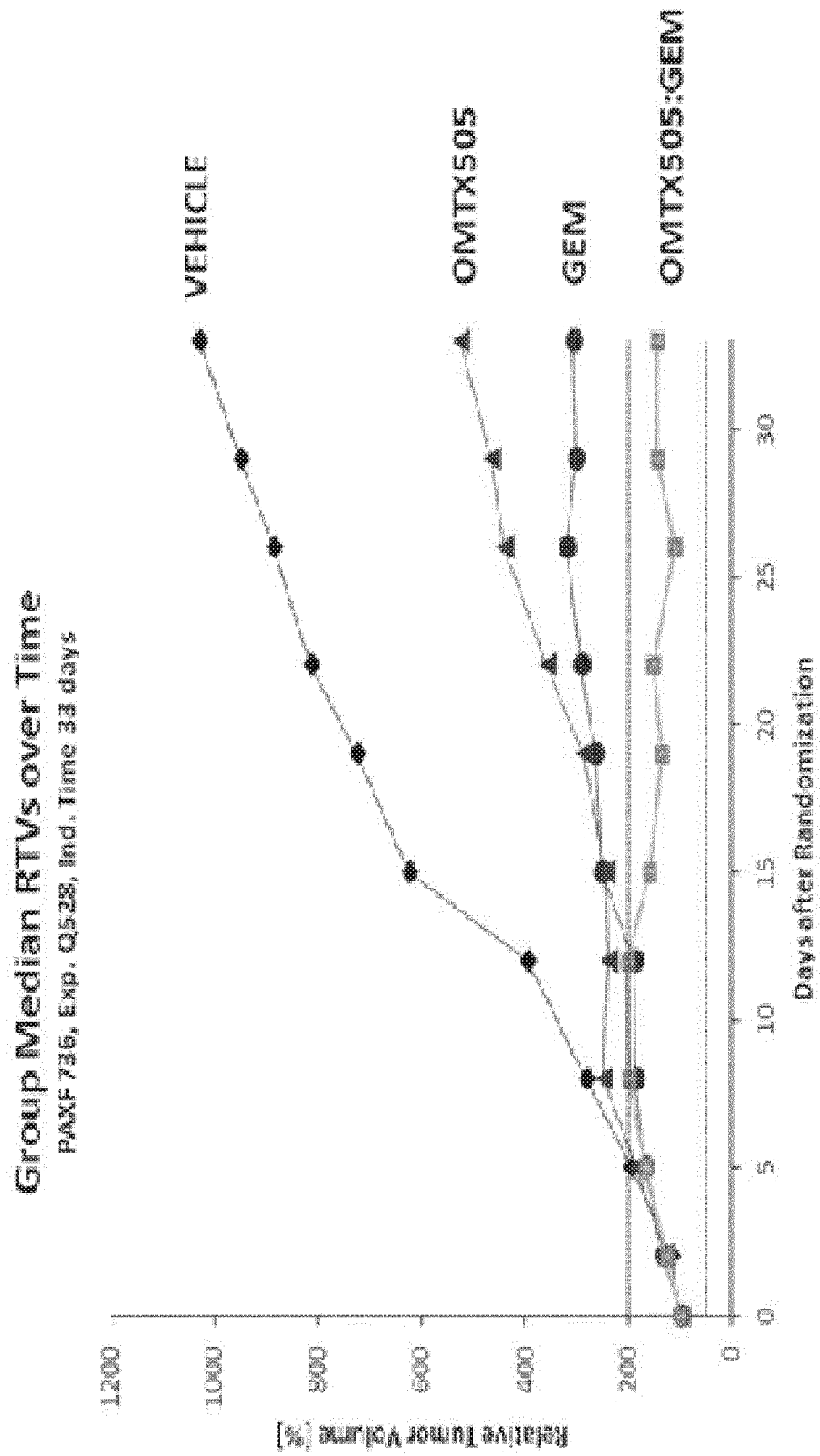

In efficacy studies performed then at nontoxic doses from 0.5 to 0.1 mg/kg, anti-FAP:recNgA immunotoxin, applied as single agent or in combination with Gemcitabine (240 mg/kg), has shown no in vivo antitumoral efficacy in FAP (−) cell line derived orthotopic xenograft murine models (not shown), while high in vivo antitumoral efficacy was evidenced at a dose of 0.5 mg/kg in FAP (+) patient-derived subcutaneous xenograft murine models of pancreas cancer (FIG. 14B). When combined with Gemcitabine (150 mg/kg), it even showed 100% tumor growth inhibition and tumor regression.

Example 5—Cytolysins and their Conjugation to Anti-FAP Antibodies

Tubulysins are recently discovered natural compounds isolated from Myxobacteria, able to destabilize the tubulin skeleton, inducing apoptosis with a very high activity.

Leading to a fast, irreversible and strong change in the cell morphology, tubulysins and their synthetic tetrapeptidic analogues, the cytolysins, are highly potent cell-killing agents (nM to pM activity). Tubulysin A inhibits tubulin polymerization in vitro with an $IC_{50}$ of 0.75-1 µM, thus blocking the formation of mitotic spindles and inducing cell cycle arrest in G2/M phase. Tubulysins compete strongly with vinblastine through binding on the vinblastine binding site of tubulin. Furthermore they are stable in lysosome enriched cell fractions (45-48).

Amenable to conjugation, many different tubulysin/cytolysin derivatives are accessible by total synthesis in sufficient quantities for preclinical and clinical development; functional groups in their structure can be adapted to several different linker technologies.

The cytolysins employed for conjugation studies were chosen from the general structure shown above (formula IV). These structures exhibit activity against different cancer cell lines (nM to pM range).

Various linker systems can be used and attached to either $R^2$ or $R^{17}$ position of the molecule.

Figure 11:
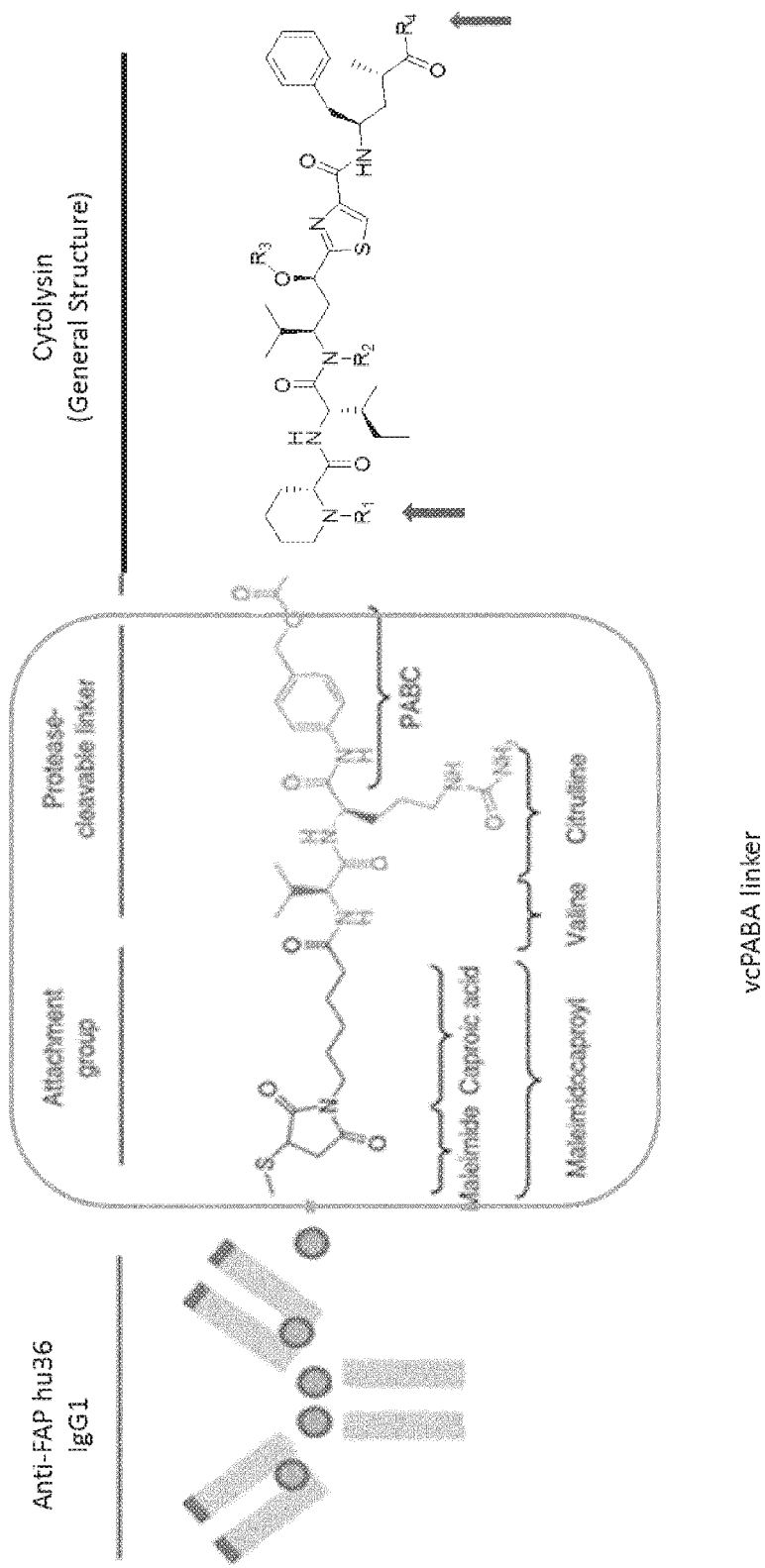
FIG. 11 shows the general antibody conjugate structure for a cytolysin-conjugated antibody via a vcPABA linker. Attachment of the cytolysin may be via $R_1$ or $R_4$ (identified by arrows).

The general outline of the cytolysin conjugates, including the vcPABA linker and anti-FAP antibody, is shown in FIG. 11 (in the structure depicted in FIG. 11, the attachment site of the cytolysin to the vcPABA linker is at position $R_1$ or $R_4$—the $R_1$ and $R_4$ numbering system used in FIG. 11 differs from the R group numbering system used, e.g., in the claims; it is intended that $R_1$ of FIG. 11 corresponds to $R^2$ in the claims and that $R_4$ of FIG. 11 corresponds to $R^{17}$ of the claims).

The vcPABA (valine-citrulline-PRBC) protease-cleavable linker has been previously used in the ADC molecule Brentuximab Vedotine, developed by Seattle Genetics and Takeda, and recently approved by the FDA and EMEA as Adcetris® (2011, and November 2012, respectively). In this ADC the vcPABA has been coupled at its free NH2 to maleimide caproyl for thiol-based conjugation on mAb (cAC10 anti-CD30 antibody). On the other side, vcPABA has been conjugated through its COOH to the Auristatin cytotoxic drug from Seattle Genetics (MMAE). (see 49)

The present inventors have used this linker (maleimide caproyl-vcPABA) to conjugate anti-FAP antibodies through thiol-based reaction with the maleimide caproyl, and on the other end, to the cytolysin cytotoxic molecules through its cyclic piperidine with vcPABA (R1 or R4 positions of the cytolysin shown in FIG. 11).

Synthesis of Maleimido-val-cit-PABOCO-Tubulysin/Cytolysin-TAM461:

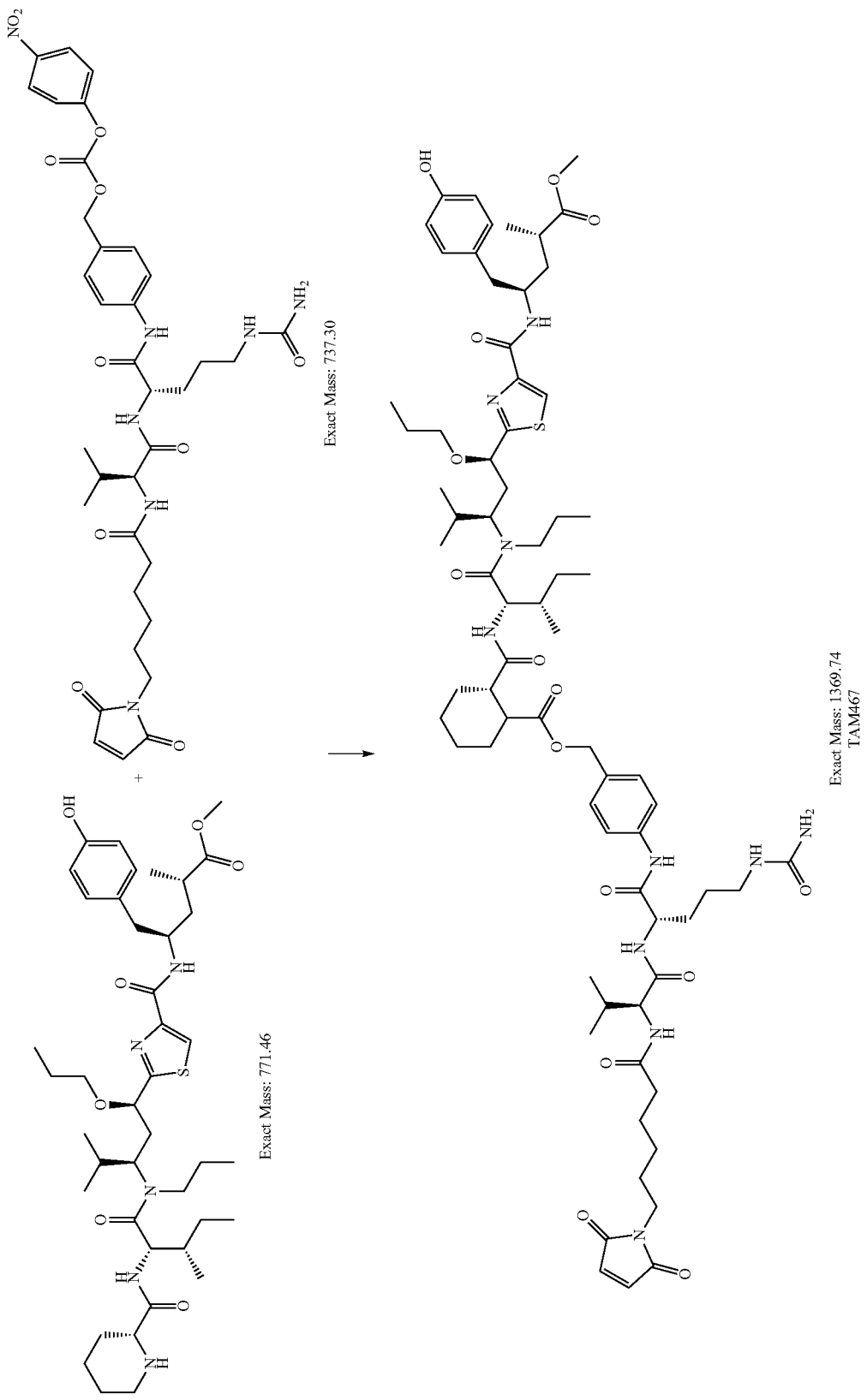

TAM461 (Tubulysin/Cytolysin): 30.0 mg (0.041 mmol)
DMF: 3 mL
TAM465 (Linker): 35 mg (0.045 mmol)
HOBt: 1.4 mg
DIPEA: 10 μL TAM461 and TAM465 were dissolved in anhydrous DMF under dry conditions and the resulting solution was treated with HOBt and DIPEA. The reaction was stirred at RT for 18 h. The reaction mixture was concentrated and the resulting oil was purified by column chromatography using 2-6% methanol: DCM to give 35 mg (64%) of TAM467 as a white solid. ESI-MS: m/z=1371 [M+H].

Synthesis of Maleimido-val-cit-PABOCO-Tubulysin/Cytolysin-TAM470:

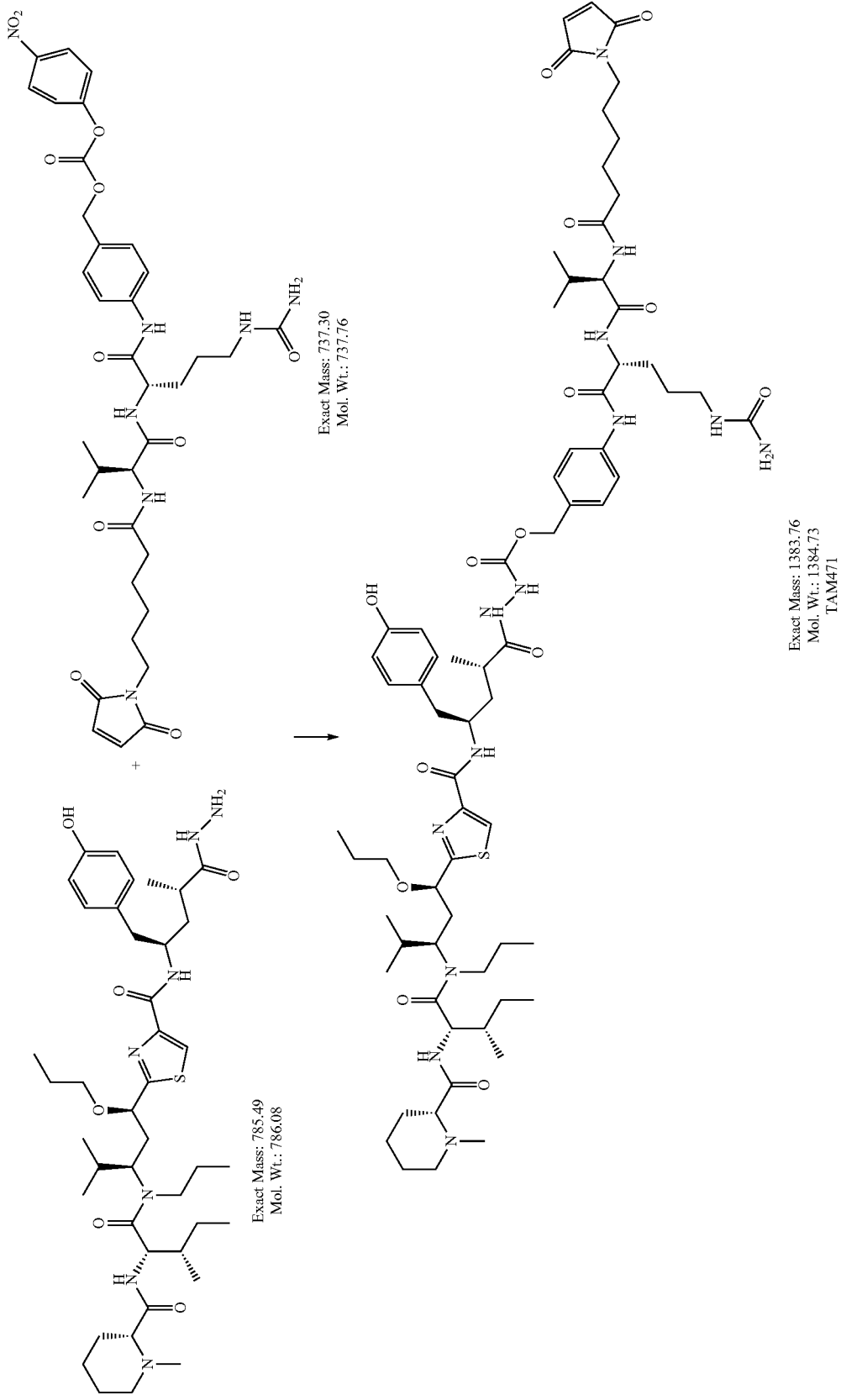

TAM470 (Tubulysin/Cytolysin): 0.07 mmol
DMF: 5 mL
TAM466 (Linker): 50 mg (0.065 mmol)
HOBt: 2.4 mg
DIPEA: 18 µL TAM470 and TAM466 were dissolved in anhydrous DMF under dry conditions and the resulting solution was treated with HOBt and DIPEA. The reaction was stirred at RT for 18 h and then analysed with TLC, indicating completion of reaction. The reaction mixture was concentrated and the resulting oil was purified with column chromatography using 4-12% methanol: DCM to give 56 mg of TAM471 (yield: 62%). ESI-MS: 1384.6 [M+1].

In vitro activity testing is performed. Functional activity will be evaluated through microtubule inhibition assay, while cytotoxic activity is determined through crystal violet viability assay.

Generation of Cytolysin-Linker Derivatives

Different cytolysin-linker derivatives were synthesized according to the general structure presented in FIG. 11, where vcPABA linker was added either in position R1 (TAM467, TAM551) or R4 (TAM471, TAM553, TAM558), alone or with ethylene-glycol spacer (EG; n=1 to 3), or substituted by ethylene glycol groups (n=3) (TAM552). The respective chemical structures are presented in Table 4.

TABLE 4
Chemical structures of cytolysin-linker derivatives
| Product | Code | Mol. Wt. |
|---|---|---|
| 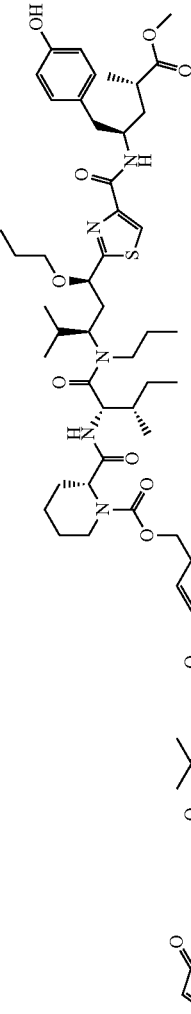 | TAM467 | 1370.7 |
| 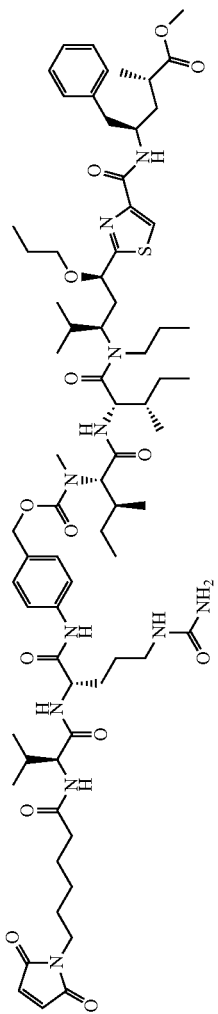 | TAM551 | 1356.7 |
| 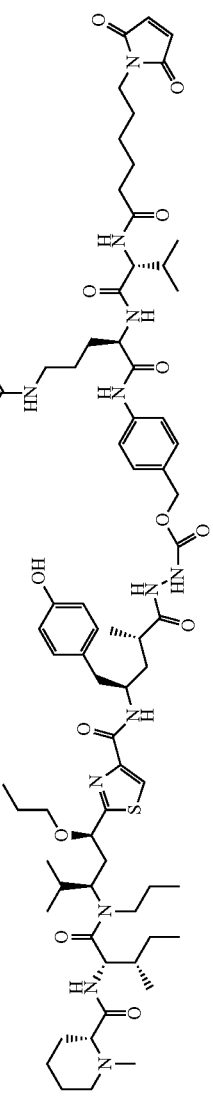 | TAM471 | 1384.7 |

TABLE 4-continued

Chemical structures of cytolysin-linker derivatives

| Product | Code | Mol. Wt. |
|---|---|---|
| (structure) | TAM552 | 1198.5 |
| (structure) | TAM553 | 1499.8 |
| (structure) | TAM558 | 1603.9 |

Microtubule inhibition inhibition activity and cytotoxic activity of each new derivative was evaluated through tubulin polymerization inhibition assay (TPI; Tubulin Polymerization assay kit; Cytoskeleton, Cat. #BK011P), and cell proliferation arrest on HT1080 cells (CPA; crystal violet). IC50 were calculated and results are presented in Table 5.

TABLE 5

Microtubule inhibition activity and Cell Cytotoxicity activity of cytolysin-linker derivatives.

| Compound | IC$_{50}$ (TPI assay; μM) | IC$_{50}$ (CPA assay; nM) |
|---|---|---|
| TAM467 (Linker in R1) | 150 | 230-420 |
| TAM551 (Linker in R1) | ND | 90 |
| TAM471 (Linker in R4; vcPABA) | 14 | 17-42 |

TABLE 5-continued

Microtubule inhibition activity and Cell Cytotoxicity activity of cytolysin-linker derivatives.

| Compound | IC$_{50}$ (TPI assay; μM) | IC$_{50}$ (CPA assay; nM) |
|---|---|---|
| TAM552 (Linker in R4; no vcPABA; 3EG) | 1.9 | 10 |
| TAM553 (Linker in R4; vcPABA; 1EG) | 6 | 98 |
| TAM558 (Linker in R4; vcPABA; 3EG) | 1.9 | 98 |
| TAM334 (parental cytolysin; no linker) | 2 | 0.3-0.6 |
| Tubulysin A | ND | 0.04-0.2 |
| Tubulysin A + linker | ND | 5-20 |
| MMAE (Seattle Genetics) | ND | 0.1-0.6 |
| DM1-DM4 (Immunogen) | ND | 0.01-0.1 |

(ND: Not determined)

In vitro activity of parental cytolysin TAM334 is within the same range of other payloads currently used for the generation of antibody-drug conjugates such as auristatins (MMAE) or maytansinoids (DM1-DM4). As expected and previously described for other compounds from the Tubulysin A family, upon addition of linker, cell cytotoxic activity of cytolysins was decreased with respect to the parental compound TAM334. In addition, TAM467 derivative was presenting significantly lowest activity in both assays. All the derivatives were used in conjugation to generate ADC molecules.

Conjugation and Chemical Characterization of ADCs

Each of the newly generated derivatives was conjugated to the anti-FAP hu36 following a non-site-specific conjugation method on cysteine residues. To this aim, one batch of antibody was reduced and reacted with each of the derivatives. Different TCEP ratios were tested to reach optimal DAR of 3-4, less than 10% of free antibody and drug. Optimal conjugation conditions were as follows: TCEP=2.5 and 3.57 Thiol levels Ellmann's. Conjugates were then purified on G25 Sephadex and analysed through Size Exclusion Chromatography (SEC) to determine their purity, as well as Hydrophobic Interaction Chromatography (HIC) and Polymeric liquid reversed-phase chromatography (PLRP) to determine DAR, content of free antibody and distribution profile of different ADC species (0-8 drugs/mAb). Content of free drug was evaluated by UV detection method at 280 nm. Results of chemical analysis (SEC, HIC and PRLP profiles) were determined for each ADC and for free antibody (data not shown). Biochemical characteristics of the ADCs is shown in Table 6.

TABLE 6

Summary of chemical characteristics of the different ADC molecules

| Lot | Drug | mAb Conc. | HIC free mAb | DAR | SEC purity 280 nm | Free Drug | Volume |
|---|---|---|---|---|---|---|---|
| HPS157-039-001 | TAM471 | 1.195 mg/mL | 10.1% | 3.38 | 92% | 0% | ~5.8 mL (6.931 mg) |
| HPS157-039-002 | TAM551 | 1.332 mg/mL | 22.4% | 3.08 | 74% | 0% | ~5.8 mL (7.726 mg) |
| HPS157-039-003 | TAM552 | 1.319 mg/mL | 5.1% | 3.84 | 97% | 0% | ~5.8 mL (7.650 mg) |
| HPS157-039-004 | TAM553 | 1.305 mg/mL | 7.0% | 4.10 | 84% | 0% | ~5.8 mL (7.569 mg) |
| HPS157-039-005 | TAM558 | 1.332 mg/mL | 5.8% | 3.92 | 93% | 0% | ~5.8 mL (7.726 mg) |

The various drugs produced different levels of aggregation. Specifically ADC HPS157-039-002 (TAM551) showed highest level of aggregation already at DAR=3.08, leaving 22.4% of unconjugated antibody. A preliminary conjugation with TAM467 also showed high level of aggregation: at DAR 3.27, SEC purity was already only 67% with 16% of free drug (data not shown). These data were suggesting that vcPABA linker in position R1 was apparently less than optimal for this type of cytolysin molecule under these conditions.

Target Binding of Conjugates

Figure 15A:
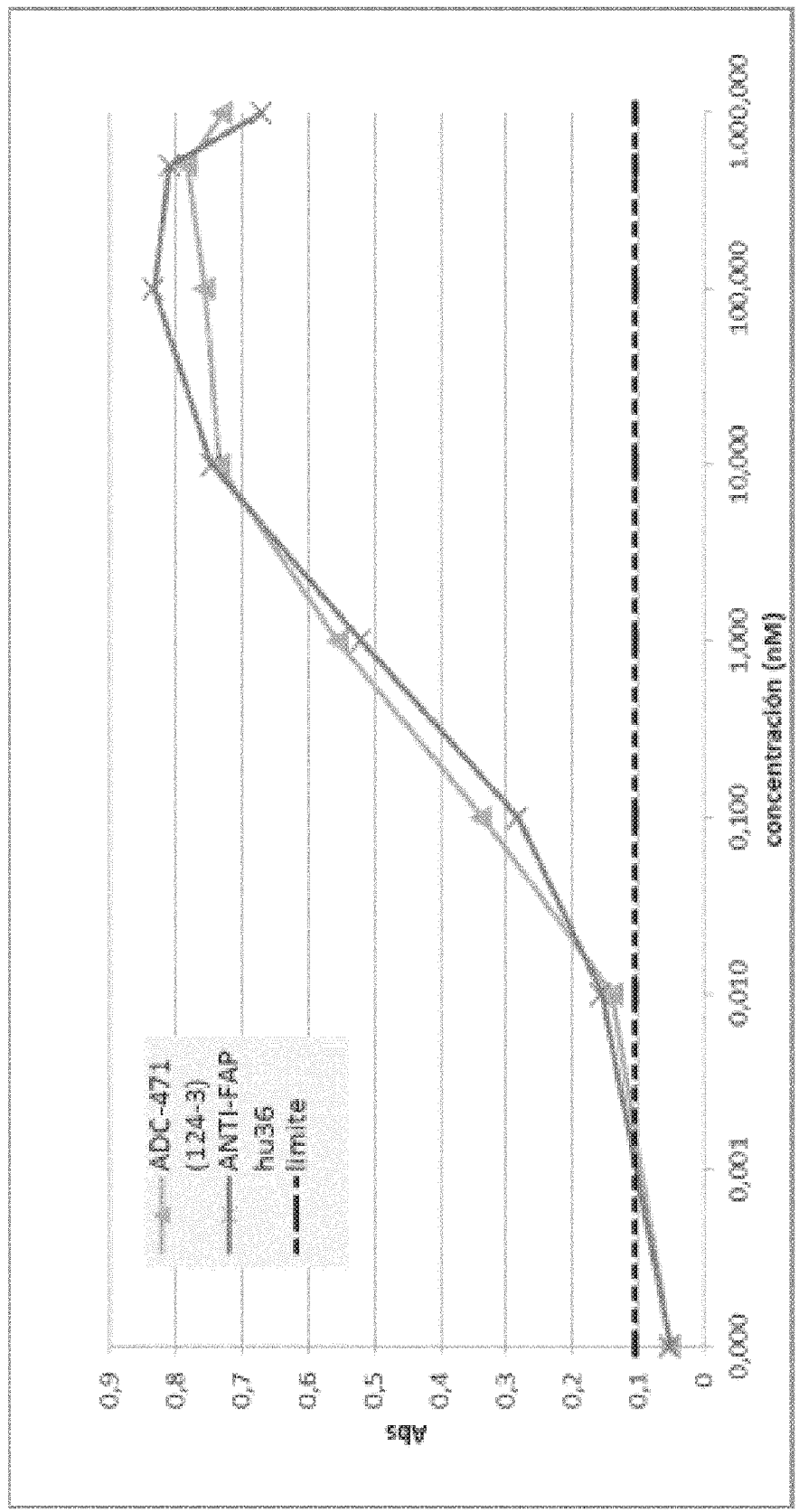
Figure 15C:
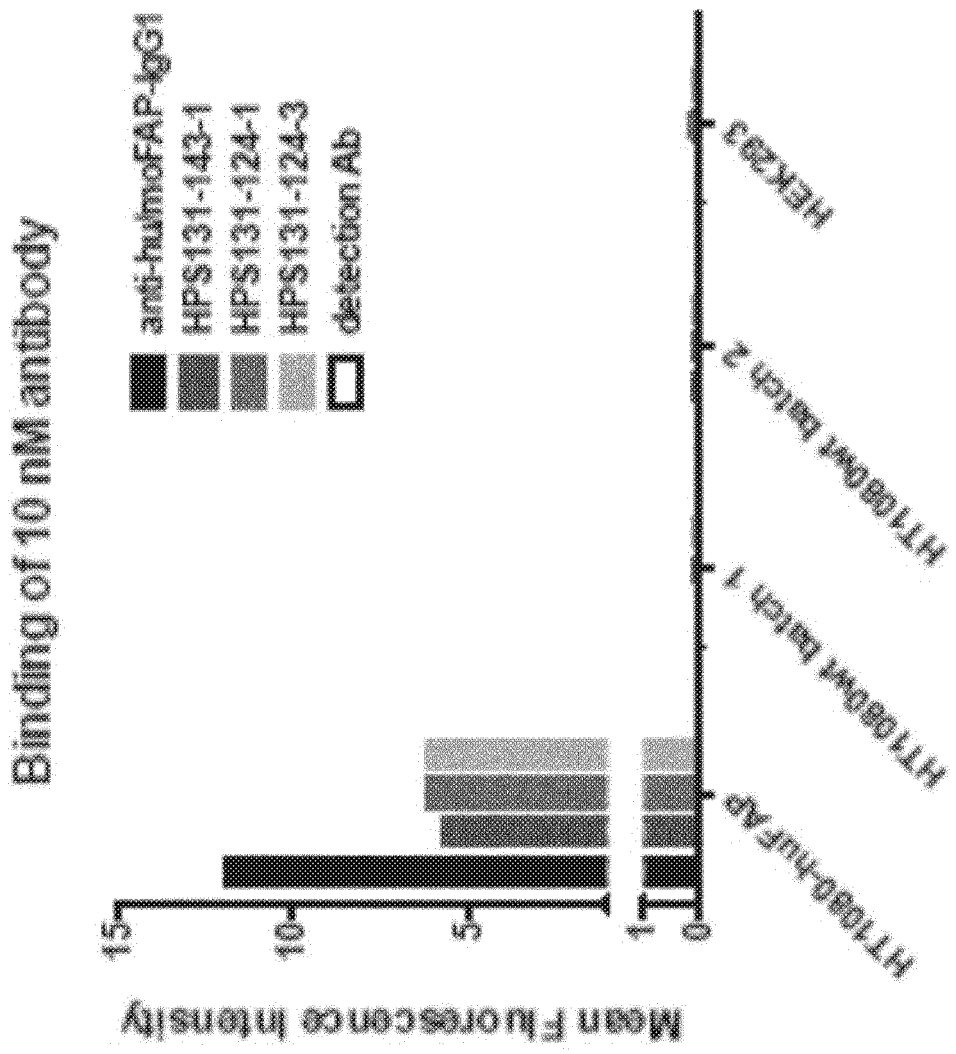

Anti-FAP hu36:TAM471 ADC binding to huFAP fusion protein was analysed by ELISA, and binding to HT1080-FAP cells by FACS (FIG. 15). For FACS analysis, compounds were incubated either at serial dilutions (FIG. 15B) or at one dilution (FIG. 15C; 10 nM) and detected with an anti-human IgG-PE (V chain specific).

EC$_{50}$ values obtained in both assays showed no significant difference with respect to naked anti-hu/moFAP hu36 antibody (FIGS. 15A & 15B). No binding was observed in FAP(−) cells such as HT1080-wt and HEK293 cells (FIG. 15C).

Figure 16:
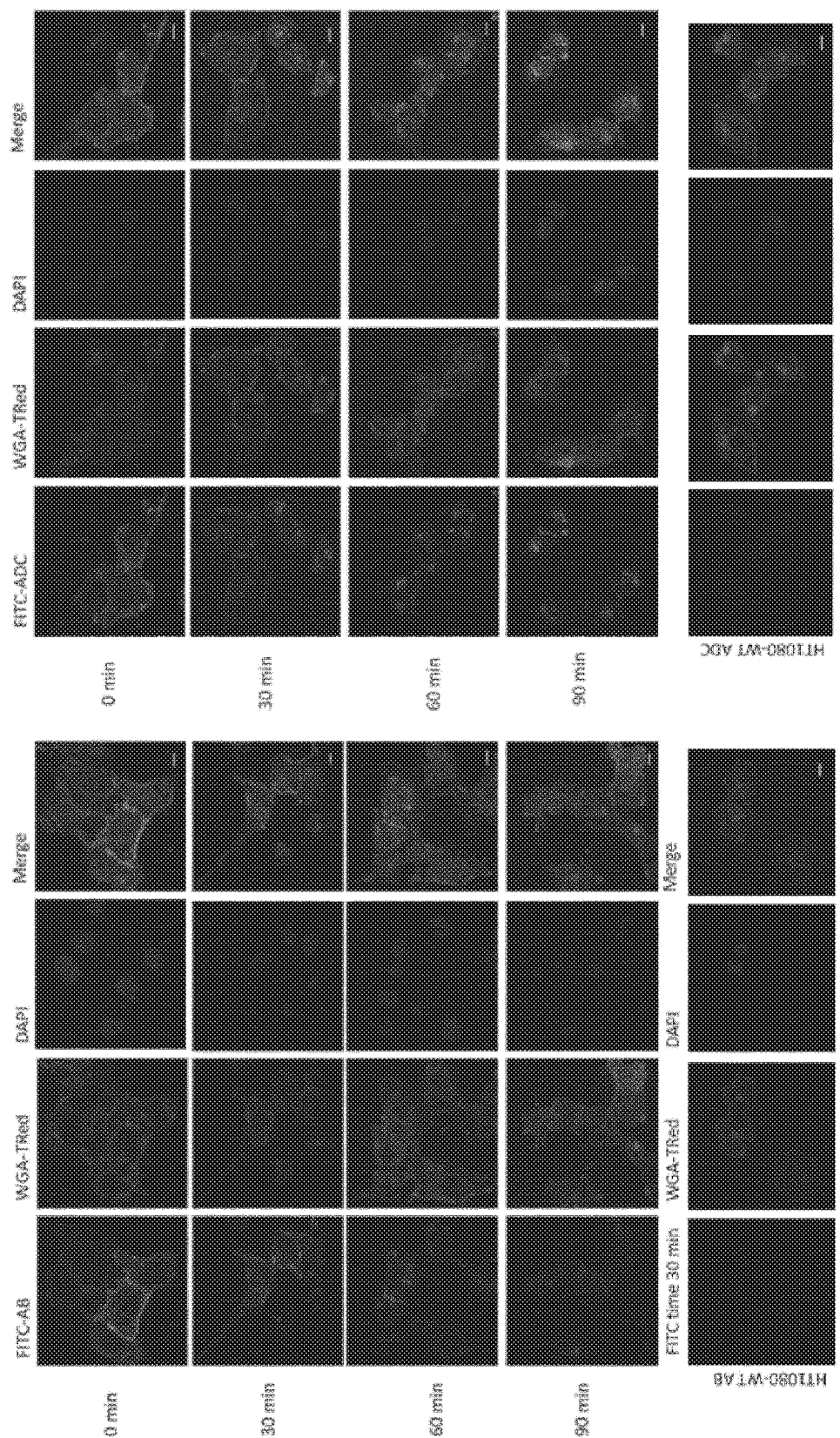
FIG. 16 shows Time-lapse immunofluorescence analysis of internalization capacity of anti-FAP hu36:cytolysin ADC (ADC-471; HPS131-124-3) on living HT1080-FAP cells. Left panel: Incubation with naked anti-hu/moFAP hu36 (FITC-AB; green); Right panel: Incubation with ADC-471 (FITC-ADC; green). Time 0, 30, 60, 90 min (upper panels): HT1080-FAP cells. Time 30 min (lower panels): HT1080-wild type cells.

FIG. 16 shows that ADC-471 (FIG. 16B) specifically binds and gets fully internalized after 90 min in HT1080-FAP cells, similarly to naked anti-FAP antibody (FIG. 16A). These results evidenced that conjugation did not affect target specificity and affinity, or internalization ability of the anti-FAP hu36 IgG1.

Example 6—Evaluation of In Vitro Cytotoxic Activity and In Vivo Anti-Tumoral Effect Anti-FAP:cytolysin ADC candidates were evaluated in vitro through proliferation arrest assay (crystal violet staining). Results are presented in FIG. 17 and IC$_{50}$ values in Table 7. Anti-tumoral effect of each ADC candidate was evaluated in a patient-derived xenograft (PDX) mouse model for pancreas cancer (PAXF-736). This model was previously selected for FAP expression level and stroma expansion. ADC compounds were administrated once a week intraperitoneally at 2.5 mg/kg. Tumor volume and body weight were measured twice a week. Vehicle-treated and Gemcitabine-treated (150 mg/kg) PDX mice were used as negative and positive control groups, respectively. Results are shown in FIG. 18.

Figure 17A:
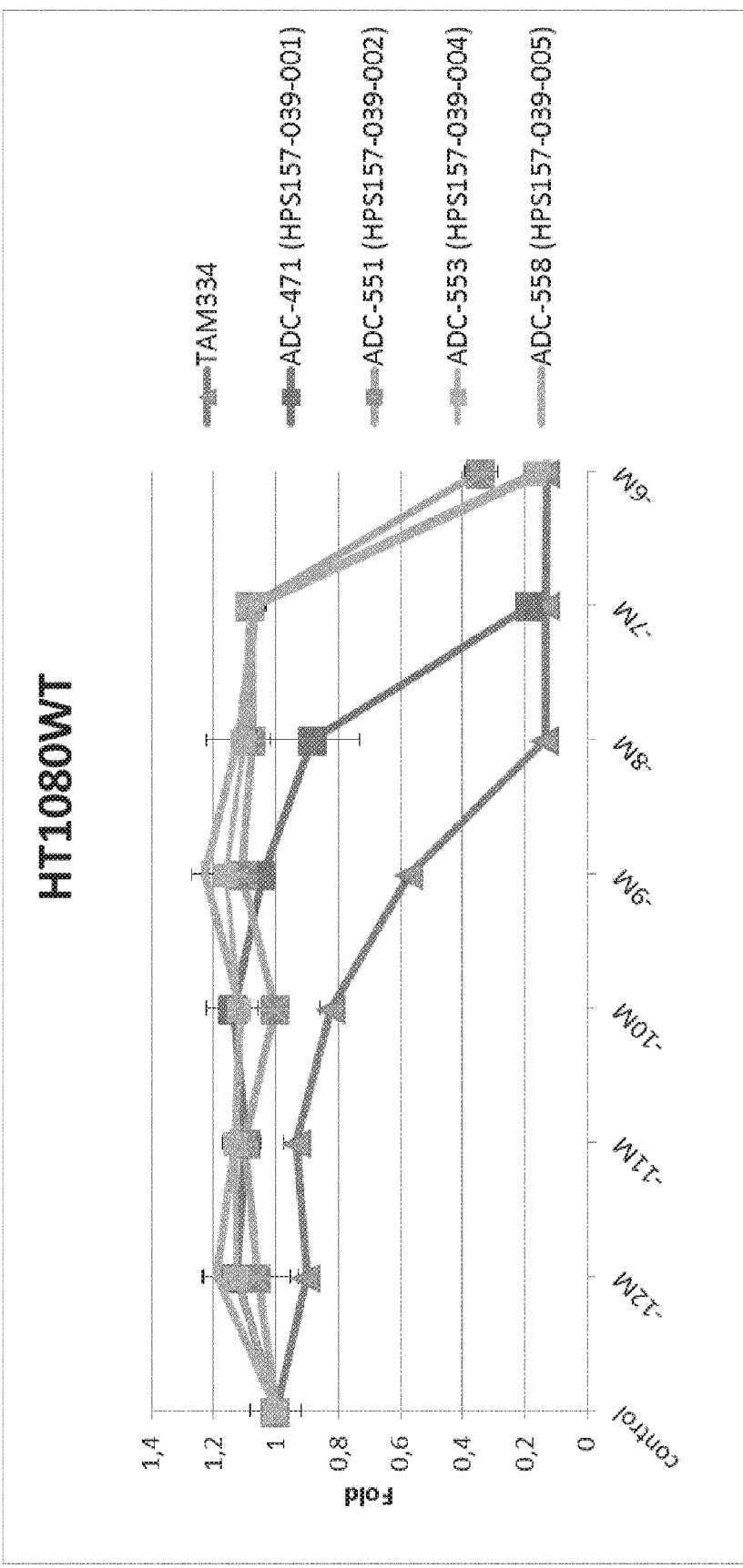
FIGS. 17A and 17B show in vitro cytotoxic effect of anti-hu/moFAP hu36: cytolysin ADCs on HT1080-wt (FIG. 17A) and FAP(+) cells (FIG. 17B). Cell proliferation arrest was evidenced through crystal violet staining after 72 h incubation of each compound at a concentration range from $10^{-6}$ to $10^{-12}$M. Parental TAM334 cytolysin was used as positive control for unspecific cytotoxicity.
Figure 17B:
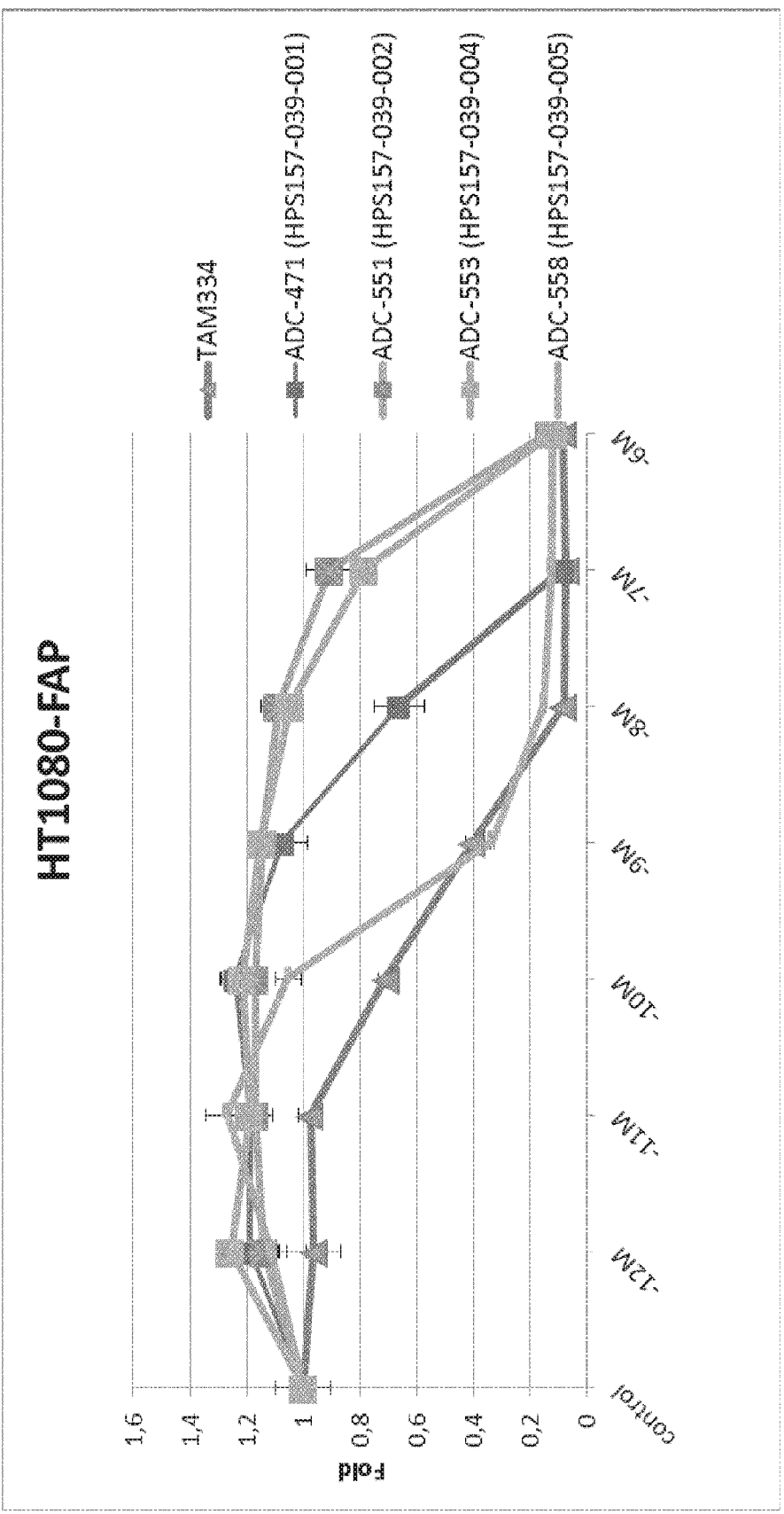

Location of vcPABA linker alone in R1 position (ADC-551) generated conjugates with much less cytotoxic activity in vitro in comparison with conjugates utilizing the R4 position (ADC-471) (FIG. 17; Table 7) and no anti-tumoral activity in vivo (FIG. 18).

Figure 18A:
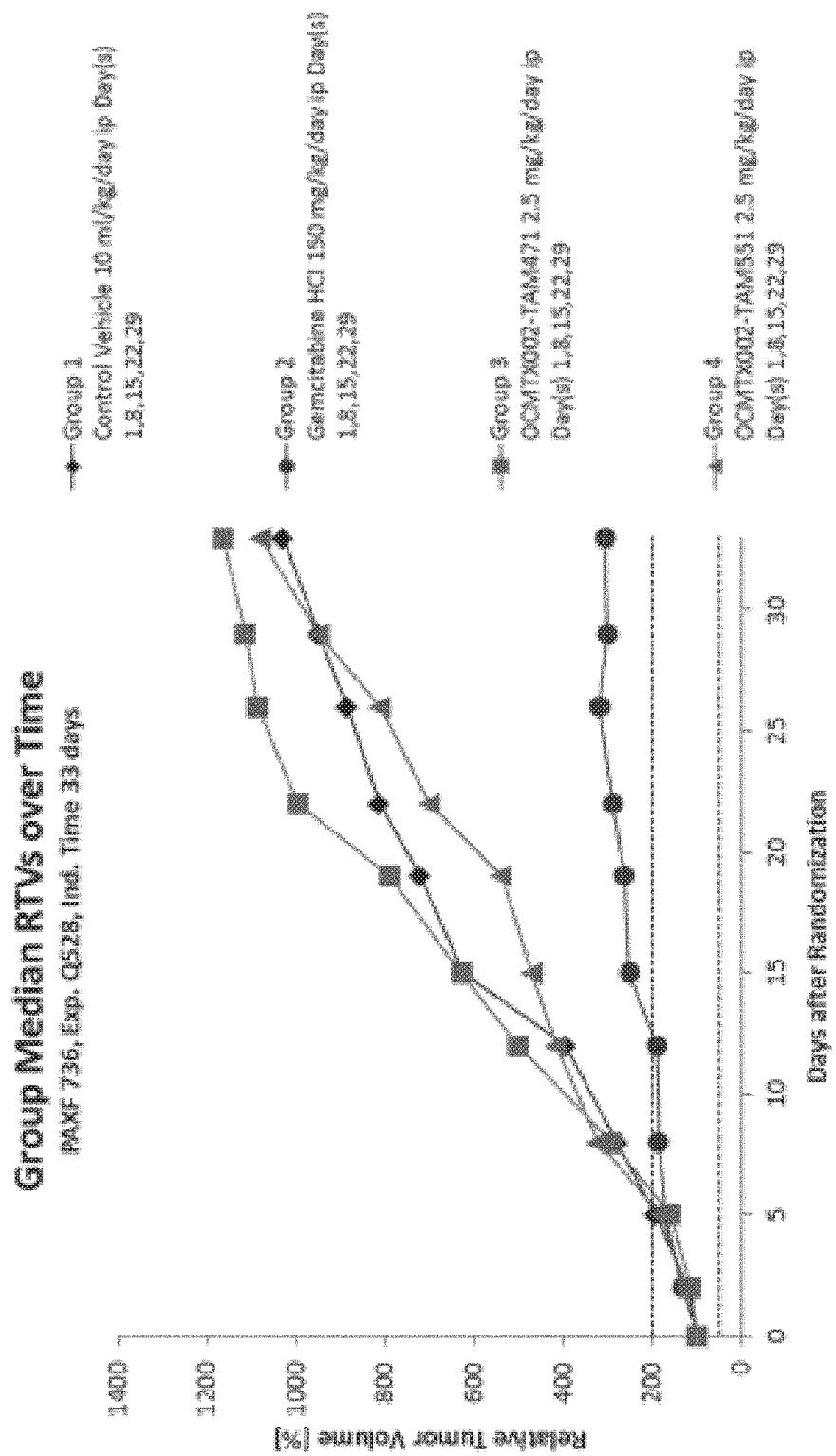
FIGS. 18A and 18B show tumor growth inhibition effect of anti-hu/moFAP hu36:cytolysin ADC candidates. DC471 versus ADC551 (FIG. 18A); ADC471 and ADC553 (OMTX705-553) versus ADC558 (OMTX705-558) (FIG. 18B). Vehicle and GEM (Gemcitabine): negative and positive control groups.
Figure 18B:
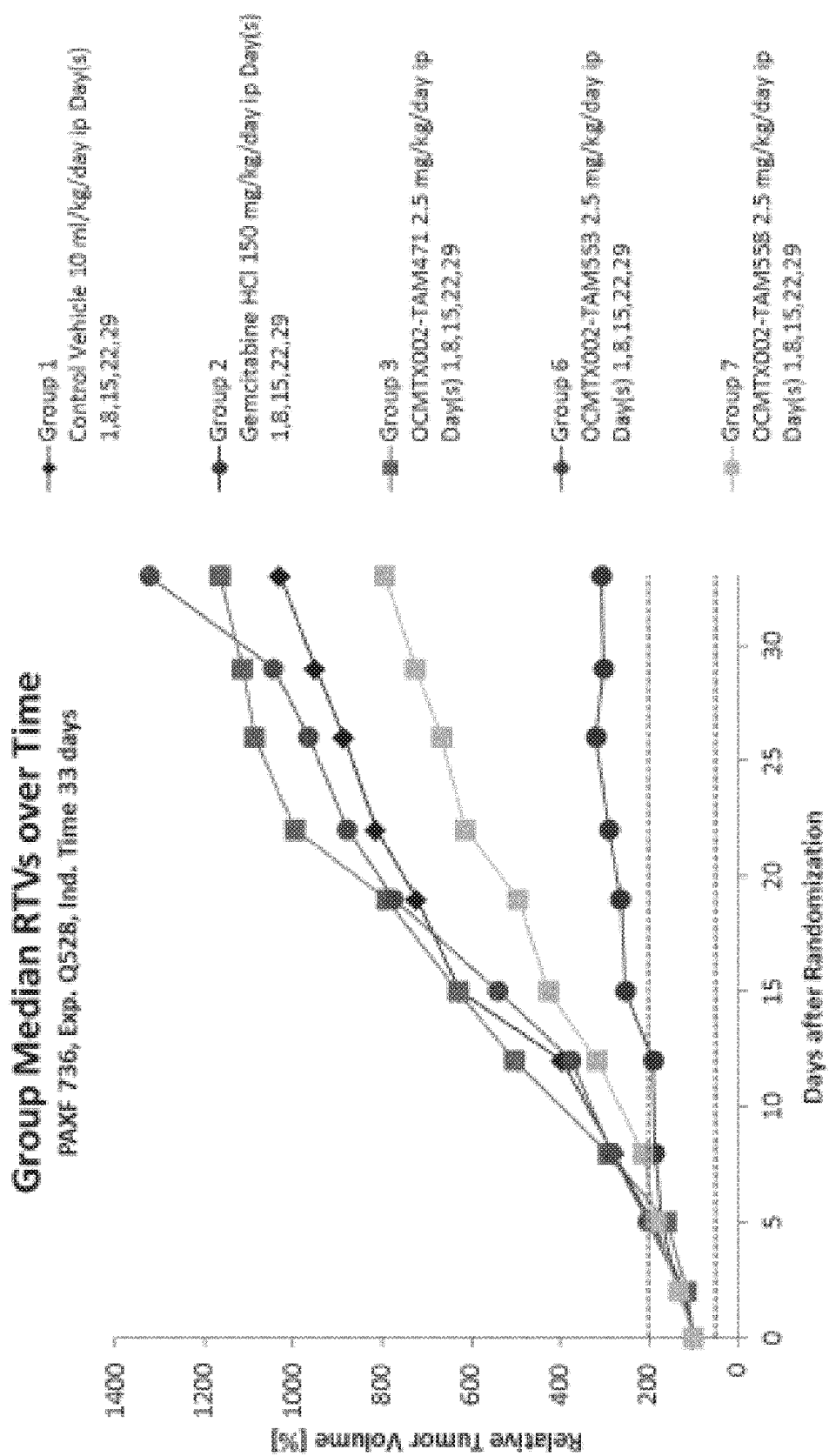

Increasing the number of ethylene-glycol groups as spacer to vcPABA linker in R4 position (ADC-471 (n=0) versus ADC-553 (n=1) and ADC-558 (n=3)) was shown to increase FAP-specific cytotoxic activity in vitro (FIG. 17) and anti-tumoral effect in vivo (FIG. 18). The TAM552 conjugate (ADC-552), having a 3 ethylene glycol spacer, but no vcPABA present in the linker was found to exhibit minimal or no in vivo anti-tumoral activity (data not shown). While ADC-471 and ADC-553 showed low and no FAP-specific cytotoxic activity (10 nM and 100 nM $IC_{50}$ range, respectively) with no difference between HT1080-WT and FAP cells nor anti-tumoral effect in vivo, ADC-558 presented a 1 nM range FAP-specific cytotoxic activity with a specificity ratio of 500 between FAP(+) and FAP(−) HT1080 cells, and a 40% tumor growth inhibition effect at 2.5 mg/kg dose in PDX mouse model for pancreas cancer. No weight loss, nor toxic effect was observed for none of the candidates at this dose (not shown).

TABLE 7

| $IC_{50}$ values obtained in Proliferation Arrest Assay (nM) | | |
|---|---|---|
| Compound | HT1080-WT | HT1080-FAP |
| TAM334 | 1.04 | 0.77 |
| ADC-471 (HPS-157-039-001) | 5.6 | 10.33 |
| ADC-551 (HPS-157-039-002) | 964 | 552 |
| ADC-553 (HPS-157-039-004) | 90 | 108 |
| ADC-558 (HPS-157-039-005) | 555 | 0.96 |

Further investigation was carried out using ADC-558. Maximum tolerated dose (MTD) was performed in normal mice and ADC-558 was found to be non-toxic within 2.5 to 25 mg/kg dose range with a weekly treatment for 3 weeks. Doses from 20, 10, and 5 mg/kg were then administrated weekly for 4 weeks to a PDX mouse model (Panc185) with high FAP expression level and stroma expansion to confirm tumor growth inhibition and full regression efficacy of the ADC-558 conjugate.

All references cited herein are incorporated herein by reference in their entirety and for all purposes to the same extent as if each individual publication or patent or patent application was specifically and individually indicated to be incorporated by reference in its entirety.

The specific embodiments described herein are offered by way of example, not by way of limitation. Any sub-titles herein are included for convenience only, and are not to be construed as limiting the disclosure in any way.

REFERENCES

1. Weinberg, R. A., et al., Garland science, Taylor & Francis Group LLC, New York, N.Y., USA, 2007
2. Nieman, K. M., et al., Nat. Med., 2011, 17: 1498-1503
3. Joyce, J. A., et al., Nat. Rev. Cancer, 2009, 9: 239-252
4. Hanahan, D., et al., Cancer Cell, 2012, 21: 309-322
5. Gupta, G. P., et al., Cell, 2006: 127: 679-695
6. Valastyan, S., et al., Cell, 2011, 147: 275-292
7. Meads, M. B, et al., Nat. Rev. Cancer, 2009, 9: 665-674
8. Olive, K. P., et al., Science, 2009, 324: 1457-1461
9. Acharyya, S., et al., Cell, 2012, 150: 165-178
10. Crawford, Y., et al. Cancer Cell, 2009, 15: 21-34
11. Straussman, R., et al., Nature, 2012, 487: 500-504
12. Joyce, J. A., et al., Cancer Cell, 2005, 7: 513-520
13. Hanahan, D., et al., Cell, 2011, 144: 646-674
14. Kalluri, R., Nat. Rev. Cancer, 2006, 6: 392-401
15. Pietras, K., et al., Exp. Cell Res., 2010, 316: 1324-1331
16. Orimo, A., et al., Cell, 2005, 121: 335-348
17. Erez, N., et al., Cancer Cell, 2010, 17: 135-147
18. Olumi, A. F., et al., Cancer Res., 1999, 59: 5002-5011
19. Yang, G., et al., Proc. Natl. Acad. Sci. USA, 2006, 103: 16472-16477
20. Hwang, R. F., et al., Cancer Res., 2008, 68: 918-926
21. Hu, M., et al., Proc. Natl. Acad. Sci. USA, 2009, 106: 3372-3377
22. Medema, J. P., et al., Nature, 2011, 474: 318-326
23. Malanchi, I., et al., Nature, 2012, 481: 85-89
24. Strell, C., et al., Ups. J. Med. Sci., 2012, 117: 187-195
25. Horimoto, Y., et al., Cell Adhes. Migr., 2012, 6: 193202
26. Wu, et al., J. Cancer Mol., 2008, 4: 37-45
27. Mersmann M., et al., Int. J. Cancer, 2001, 92: 240-248
28. Brocks B., et al., Molecular Medicine, 2001, 7: 461-469
29. Schmidt A., et al., Eur. J. Biochem., 2001, 268: 1730-1738
30. Messerschmidt, S. K., et al., J Control Release, 2009, 137: 69-77
31. Ostermann E., et al., Clin. Cancer Res., 2008, 14: 4584-4592
32. Shi, M., et al., World J. Gastroenterology, 2012, 28: 840-846.
33. Munoz et al., Cancer Res., 2001
34. Trush et al., *Annu. Rev. Immunol.,* 1996, 14:49-71
35. Lambert et al., 1988,
36. Barbieri, et al., *Methods in Mol. Biol.,* 2001, 166: 71-85
37. Ghetie and Vitetta, *Mol. Biotechnol.,* 2001, 18: 251-286
38. Munoz R., et al., Cancer Lett., 2007, 256: 73-80.
39. Munoz R., et al., Cancer Immunol. Immunother., 2012
40. Thorpe et al., *Cancer Res.,* 1987, 47:5924-5931
41. Fracasso et al., *Mini Rev. Med. Chem.,* 2004, 4: 545-562
42. Marsh et al., "*Immunotoxins*", Frankel A. E. ed., Kluwer Academic Publishers, Boston, Mass., 1988, 213-237
43. Riddles et al., *Anal. Biochem.,* 1979, 94:75-81
44. Riener et al., *Anal. Bioanal. Chem,* 2002, 373:266-276
45. Sasse, F., et al., Journal of Antibiotics, 2000, 53:879-885.
46. Kaur, G., et al., Biochem. J., 2006, 396:235-242.
47. Schluep, T., et al., Clin. Cancer Res., 2009, 15:181-189
48. Reddy, J. A., et al., Mol. Pharmaceutics, 2009.
49. Gualberto A. *Expert Opin Investig Drugs.* 2012; 21(2): 205-16
50. Perez-Soler et al., *Clin. Cancer Res.,* 2000, 6: 4932-4938;
51. Yabuchi et al., *Cancer Letters,* 2013

The invention claimed is:

1. A conjugate having the formula I:

A-(L-D)$_p$  (I)

or a pharmaceutically acceptable salt or solvate thereof, wherein:

A is an antibody that selectively binds FAP;
L is a linker comprising a spacer;

D is a drug comprising a cytolysin of formula IV:

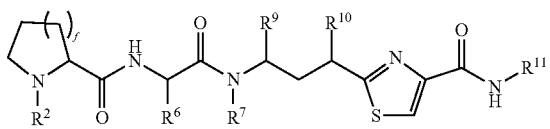

wherein:
$R^2$ is H or $C_1$-$C_4$ alkyl;
$R^6$ is $C_1$-$C_6$ alkyl;
$R^7$ is $C_1$-$C_6$ alkyl, $CH_2OR^{19}$ or $CH_2OCOR^{20}$, wherein $R^{19}$ is alkyl, $R^{20}$ is $C_2$-$C_6$-alkenyl, phenyl, or $CH_2$-phenyl;
$R^9$ is $C_1$-$C_6$ alkyl;
$R^{10}$ is H, OH, O-alkyl or O-acetyl;
f is 1 or 2;
$R^{11}$ has the following structure:
$R^{21}$

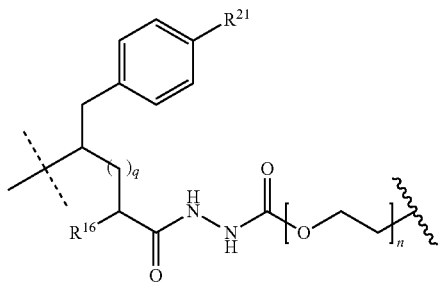

wherein
$R^{21}$ is H, OH, halogen, $NH_2$, alkyloxy, phenyl, alkyl amino or dialkyl amino;
$R^{16}$ is H or a $C_1$-$C_6$-alkyl group;
n=2, 3 or 4;
q is 0, 1, 2 or 3; and
p is 1 to 10.

2. The conjugate of claim 1, wherein A comprises heavy chain complementarity determining regions 1-3 (CDRH1-3) and light chain complementarity determining regions 1-3 (CDRL1-3) having the following amino acid sequences:
(i) CDRH1: SEQ ID NO: 7;
(ii) CDRH2: SEQ ID NO: 8;
(iii) CDRH3: SEQ ID NO: 9;
(iv) CDRL1: SEQ ID NO: 10;
(v) CDRL2: SEQ ID NO: 11; and
(vi) CDRL3: SEQ ID NO: 12.

3. The conjugate of claim 1, wherein L comprises an attachment group for attachment to A and a protease cleavable portion.

4. The conjugate of claim 3, wherein L comprises maleimidocaproyl-valine-citrulline-p-aminobenzylcarbamate.

5. The conjugate of claim 1, wherein $R^2$ is methyl, f=2, $R^6$ is $C_4$ alkyl, $R^7$ is $C_3$ alkyl, $R^9$ is $C_3$ alkyl, $R^{10}$ is O-alkyl, $R^{21}$ is OH, q is 1, and $R^{16}$ is methyl.

6. The conjugate of claim 1, wherein n=3.

7. A method of treating a tumor in a mammalian subject, wherein said tumor and/or stroma surrounding said tumor expresses fibroblast activation protein alpha (FAP), said method comprising administering a therapeutically effective amount of a conjugate of claim 1 to a subject in need thereof.

8. The method of claim 7, wherein said conjugate is administered simultaneously, sequentially or separately with one or more other antitumor drugs.

9. The method of claim 8, wherein said one or more other antitumor drugs comprise a cytotoxic chemotherapeutic agent or an anti-angiogenic agent or an immunotherapeutic agent.

10. The method of claim 9, wherein said one or more other antitumor drugs comprise Gemcitabine, Abraxane, bevacizumab, itraconazole, or carboxyamidotriazole, an anti-PD-1 molecule or an anti-PD-L1 molecule.

11. The method of claim 10, wherein said anti-PD-1 molecule or anti-PD-L1 molecule comprises nivolumab or pembrolizumab.

12. The method of claim 7, wherein the FAP expressing tumor is a solid tumor.

13. The method of claim 12, wherein the solid tumor is an FAP expressing solid tumor of pancreatic cancer, breast cancer, melanoma, lung cancer, head and neck cancer, ovarian cancer, bladder cancer or colon cancer.

14. A method of treating a fibroblast activation protein alpha (FAP) expressing inflammatory condition in a mammalian subject, comprising administering a therapeutically effective amount of a conjugate of claim 1 to a subject in need thereof.

15. The method of claim 14, wherein said FAP expressing inflammatory condition is FAP expressing rheumatoid arthritis.

16. A conjugate having the formula I:

$$A\text{-}(L\text{-}D)_p \qquad (I)$$

or a pharmaceutically acceptable salt or solvate thereof, wherein:
A is an antibody that selectively binds FAP;
L is a linker;
D is a drug having the structure:

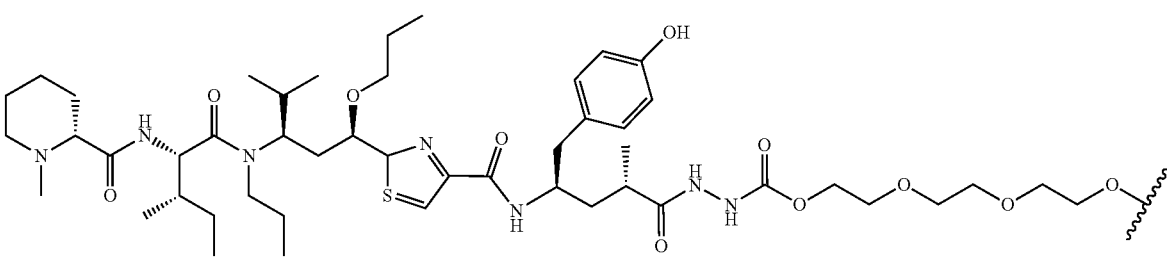

wherein p is 1 to 10.

17. The conjugate of claim 16, wherein L comprises maleimidocaproyl-valine-citrulline-p-aminobenzylcarbamate.

* * * * *

SEQUENCE LISTING

<160> NUMBER OF SEQ ID NOS: 16

<210> SEQ ID NO 1
<211> LENGTH: 469
<212> TYPE: PRT
<213> ORGANISM: Artificial sequence
<220> FEATURE:
<223> OTHER INFORMATION: Synthetic sequence: Anti-FAP hu36-IgG1-HC

<400> SEQUENCE: 1

Met Glu Thr Asp Thr Leu Leu Leu Trp Val Leu Leu Trp Val Pro
1               5                   10                  15

Gly Ser Thr Gly Gln Val Gln Leu Val Gln Ser Gly Ala Glu Val Lys
            20                  25                  30

Lys Pro Gly Ala Ser Val Lys Val Ser Cys Lys Ala Ser Gly Tyr Thr
        35                  40                  45

Phe Thr Glu Asn Ile Ile His Trp Val Arg Gln Ala Pro Gly Gln Gly
    50                  55                  60

Leu Glu Trp Met Gly Trp Phe His Pro Gly Ser Gly Ser Ile Lys Tyr
65                  70                  75                  80

Asn Glu Lys Phe Lys Asp Arg Val Thr Met Thr Ala Asp Thr Ser Thr
                85                  90                  95

Ser Thr Val Tyr Met Glu Leu Ser Ser Leu Arg Ser Glu Asp Thr Ala
            100                 105                 110

Val Tyr Tyr Cys Ala Arg His Gly Gly Thr Gly Arg Gly Ala Met Asp
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Pro
                245                 250                 255

Val Ala Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Gly Leu Pro Ser
            340                 345                 350

Ser Ile Glu Lys Thr Ile Ser Lys Ala Lys Gly Gln Pro Arg Glu Pro

```
                355                 360                 365
Gln Val Tyr Thr Leu Pro Pro Ser Arg Asp Glu Leu Thr Lys Asn Gln
        370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
        420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
465

<210> SEQ ID NO 2
<211> LENGTH: 238
<212> TYPE: PRT
<213> ORGANISM: Artificial sequence
<220> FEATURE:
<223> OTHER INFORMATION: Synthetic sequence: Anti-FAP hu36-IgG1-LC

<400> SEQUENCE: 2

Met Glu Thr Asp Thr Leu Leu Leu Trp Val Leu Leu Leu Trp Val Pro
1               5                   10                  15

Gly Ser Thr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Lys Ser
        35                  40                  45

Val Ser Thr Ser Ala Tyr Ser Tyr Met His Trp Tyr Gln Gln Lys Pro
    50                  55                  60

Gly Lys Ala Pro Lys Leu Leu Ile Tyr Leu Ala Ser Asn Leu Glu Ser
65                  70                  75                  80

Gly Val Pro Ser Arg Phe Ser Gly Ser Gly Ser Gly Thr Asp Phe Thr
                85                  90                  95

Leu Thr Ile Ser Ser Leu Gln Pro Glu Asp Phe Ala Thr Tyr Tyr Cys
            100                 105                 110

Gln His Ser Arg Glu Leu Pro Tyr Thr Phe Gly Gln Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

```
<210> SEQ ID NO 3
<211> LENGTH: 449
<212> TYPE: PRT
<213> ORGANISM: Artificial sequence
<220> FEATURE:
<223> OTHER INFORMATION: Synthetic sequence: hu36-IgG1-HC - without
      signal sequence

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Asn
                20                  25                  30

Ile Ile His Trp Val Arg Gln Ala Pro Gly Gln Gly Leu Glu Trp Met
            35                  40                  45

Gly Trp Phe His Pro Gly Ser Gly Ser Ile Lys Tyr Asn Glu Lys Phe
        50                  55                  60

Lys Asp Arg Val Thr Met Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg His Gly Gly Thr Gly Arg Gly Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365
```

```
Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 4
<211> LENGTH: 218
<212> TYPE: PRT
<213> ORGANISM: Artificial sequence
<220> FEATURE:
<223> OTHER INFORMATION: Synthetic sequence: hu36-IgG1-LC - without
      signal sequence

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Val Ser Thr Ser
            20                  25                  30

Ala Tyr Ser Tyr Met His Trp Tyr Gln Gln Lys Pro Gly Lys Ala Pro
        35                  40                  45

Lys Leu Leu Ile Tyr Leu Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Arg
                85                  90                  95

Glu Leu Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 5
<211> LENGTH: 120
<212> TYPE: PRT
<213> ORGANISM: Artificial sequence
<220> FEATURE:
<223> OTHER INFORMATION: Synthetic sequence: hu36-VH

<400> SEQUENCE: 5
```

```
Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Glu Asn
            20                  25                  30

Ile Ile His Trp Val Arg Gln Ala Pro Gly Gln Gly Leu Glu Trp Met
            35                  40                  45

Gly Trp Phe His Pro Gly Ser Gly Ser Ile Lys Tyr Asn Glu Lys Phe
50                  55                  60

Lys Asp Arg Val Thr Met Thr Ala Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg His Gly Gly Thr Gly Arg Gly Ala Met Asp Tyr Trp Gly Gln
                100                 105                 110

Gly Thr Leu Val Thr Val Ser Ser
        115                 120
```

<210> SEQ ID NO 6
<211> LENGTH: 112
<212> TYPE: PRT
<213> ORGANISM: Artificial sequence
<220> FEATURE:
<223> OTHER INFORMATION: Synthetic sequence: hu36-VL

<400> SEQUENCE: 6

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Val Ser Thr Ser
            20                  25                  30

Ala Tyr Ser Tyr Met His Trp Tyr Gln Gln Lys Pro Gly Lys Ala Pro
            35                  40                  45

Lys Leu Leu Ile Tyr Leu Ala Ser Asn Leu Glu Ser Gly Val Pro Ser
50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Arg
                85                  90                  95

Glu Leu Pro Tyr Thr Phe Gly Gln Gly Thr Lys Leu Glu Ile Lys Arg
                100                 105                 110
```

<210> SEQ ID NO 7
<211> LENGTH: 5
<212> TYPE: PRT
<213> ORGANISM: Artificial sequence
<220> FEATURE:
<223> OTHER INFORMATION: Synthetic sequence: hu36-CDRH1

<400> SEQUENCE: 7

```
Glu Asn Ile Ile His
1               5
```

<210> SEQ ID NO 8
<211> LENGTH: 17
<212> TYPE: PRT
<213> ORGANISM: Artificial sequence
<220> FEATURE:
<223> OTHER INFORMATION: Synthetic sequence: hu36-CDRH2

<400> SEQUENCE: 8

```
Trp Phe His Pro Gly Ser Gly Ser Ile Lys Tyr Asn Glu Lys Phe Lys
1               5                   10                  15

Asp

<210> SEQ ID NO 9
<211> LENGTH: 11
<212> TYPE: PRT
<213> ORGANISM: Artificial sequence
<220> FEATURE:
<223> OTHER INFORMATION: Synthetic sequence: hu36-CDRH3

<400> SEQUENCE: 9

His Gly Gly Thr Gly Arg Gly Ala Met Asp Tyr
1               5                   10

<210> SEQ ID NO 10
<211> LENGTH: 15
<212> TYPE: PRT
<213> ORGANISM: Artificial sequence
<220> FEATURE:
<223> OTHER INFORMATION: Synthetic sequence: hu36-CDRL1

<400> SEQUENCE: 10

Arg Ala Ser Lys Ser Val Ser Thr Ser Ala Tyr Ser Tyr Met His
1               5                   10                  15

<210> SEQ ID NO 11
<211> LENGTH: 7
<212> TYPE: PRT
<213> ORGANISM: Artificial sequence
<220> FEATURE:
<223> OTHER INFORMATION: Synthetic sequence: hu36-CDRL2

<400> SEQUENCE: 11

Leu Ala Ser Asn Leu Glu Ser
1               5

<210> SEQ ID NO 12
<211> LENGTH: 9
<212> TYPE: PRT
<213> ORGANISM: Artificial sequence
<220> FEATURE:
<223> OTHER INFORMATION: Synthetic sequence: hu36-CDRL3

<400> SEQUENCE: 12

Gln His Ser Arg Glu Leu Pro Tyr Thr
1               5

<210> SEQ ID NO 13
<211> LENGTH: 256
<212> TYPE: PRT
<213> ORGANISM: Artificial sequence
<220> FEATURE:
<223> OTHER INFORMATION: Synthetic sequence: Recombinant Nigrin-b A-
      chain amino acid sequence

<400> SEQUENCE: 13

Met Ile Asp Tyr Pro Ser Val Ser Phe Asn Leu Asp Gly Ala Lys Ser
1               5                   10                  15

Ala Thr Tyr Arg Asp Phe Leu Ser Asn Leu Arg Lys Val Ala Thr
            20                  25                  30

Gly Thr Tyr Glu Val Asn Gly Leu Pro Val Leu Arg Arg Glu Ser Glu
        35                  40                  45

Val Gln Val Lys Ser Arg Phe Val Leu Val Pro Leu Thr Asn Tyr Asn
    50                  55                  60
```

```
Gly Asn Thr Val Thr Leu Ala Val Asp Val Thr Asn Leu Tyr Val Val
65                  70                  75                  80

Ala Phe Ser Gly Asn Ala Asn Ser Tyr Phe Phe Lys Asp Ala Thr Glu
                85                  90                  95

Val Gln Lys Ser Asn Leu Phe Val Gly Thr Lys Gln Asn Thr Leu Ser
            100                 105                 110

Phe Thr Gly Asn Tyr Asp Asn Leu Glu Thr Ala Ala Asn Thr Arg Arg
        115                 120                 125

Glu Ser Ile Glu Leu Gly Pro Ser Pro Leu Asp Gly Ala Ile Thr Ser
    130                 135                 140

Leu Tyr His Gly Asp Ser Val Ala Arg Ser Leu Leu Val Val Ile Gln
145                 150                 155                 160

Met Val Ser Glu Ala Ala Arg Phe Arg Tyr Ile Glu Gln Glu Val Arg
                165                 170                 175

Arg Ser Leu Gln Gln Ala Thr Ser Phe Thr Pro Asn Ala Leu Met Leu
            180                 185                 190

Ser Met Glu Asn Asn Trp Ser Ser Met Ser Leu Glu Ile Gln Gln Ala
        195                 200                 205

Gly Asn Asn Val Ser Pro Phe Phe Gly Thr Val Gln Leu Leu Asn Tyr
    210                 215                 220

Asp His Thr His Arg Leu Val Asp Asn Phe Glu Glu Leu Tyr Lys Ile
225                 230                 235                 240

Thr Gly Ile Ala Ile Leu Leu Phe Arg Cys Ser Ser Pro Ser Asn Asp
                245                 250                 255
```

<210> SEQ ID NO 14
<211> LENGTH: 765
<212> TYPE: DNA
<213> ORGANISM: Artificial sequence
<220> FEATURE:
<223> OTHER INFORMATION: Synthetic sequence: Nucleotide sequence encoding recombinant Nigrin-b A-chain

<400> SEQUENCE: 14

```
atagactatc cctccgtctc cttcaacttg gatggagcca agtcggctac atacagggac     60
ttcctcagca acctgcgaaa aacagtggca actggcacct atgaagtaaa cggtttacca    120
gtactgaggc gcgaaagtga agtacaggtc aagagtcggt tcgttctcgt ccctctcacc    180
aattacaatg gaaacaccgt cacgttggca gtagatgtga ccaaccttta cgtggtggct    240
tttagtggaa atgcaaactc ctactttttc aaggacgcta cggaagttca aaagagtaat    300
ttattcgttg gcaccaagca aaatacgtta tccttcacgg gtaattatga caaccttgag    360
actgcggcga atactaggag ggagtctatc gaactgggac ccagtccgct agatggagcc    420
attacaagtt tgtatcatgg tgatagcgta gcccgatctc tccttgtggt aattcagatg    480
gtctcggaag cggcaaggtt cagatacatt gagcaagaag tgcgccgaag cctacagcag    540
gctacaagct tcacaccaaa tgctttgatg ctgagcatgg agaacaactg gtcgtctatg    600
tccttggaga tccagcaggc gggaaataat gtatcaccct tctttgggac cgttcagctt    660
ctaaattacg atcacactca ccgcctagtt gacaactttg aggaactcta taagattacg    720
gggatagcaa ttcttctctt ccgttgctcc tcaccaagca atgat                    765
```

<210> SEQ ID NO 15
<211> LENGTH: 760
<212> TYPE: PRT
<213> ORGANISM: Homo sapiens

<400> SEQUENCE: 15

```
Met Lys Thr Trp Val Lys Ile Val Phe Gly Val Ala Thr Ser Ala Val
1               5                   10                  15

Leu Ala Leu Leu Val Met Cys Ile Val Leu Arg Pro Ser Arg Val His
            20                  25                  30

Asn Ser Glu Glu Asn Thr Met Arg Ala Leu Thr Leu Lys Asp Ile Leu
        35                  40                  45

Asn Gly Thr Phe Ser Tyr Lys Thr Phe Pro Asn Trp Ile Ser Gly
    50                  55                  60

Gln Glu Tyr Leu His Gln Ser Ala Asp Asn Ile Val Leu Tyr Asn
65                  70                  75                  80

Ile Glu Thr Gly Gln Ser Tyr Thr Ile Leu Ser Asn Arg Thr Met Lys
                85                  90                  95

Ser Val Asn Ala Ser Asn Tyr Gly Leu Ser Pro Asp Arg Gln Phe Val
            100                 105                 110

Tyr Leu Glu Ser Asp Tyr Ser Lys Leu Trp Arg Tyr Ser Tyr Thr Ala
        115                 120                 125

Thr Tyr Tyr Ile Tyr Asp Leu Ser Asn Gly Glu Phe Val Arg Gly Asn
    130                 135                 140

Glu Leu Pro Arg Pro Ile Gln Tyr Leu Cys Trp Ser Pro Val Gly Ser
145                 150                 155                 160

Lys Leu Ala Tyr Val Tyr Gln Asn Asn Ile Tyr Leu Lys Gln Arg Pro
                165                 170                 175

Gly Asp Pro Pro Phe Gln Ile Thr Phe Asn Gly Arg Glu Asn Lys Ile
            180                 185                 190

Phe Asn Gly Ile Pro Asp Trp Val Tyr Glu Glu Met Leu Ala Thr
        195                 200                 205

Lys Tyr Ala Leu Trp Trp Ser Pro Asn Gly Lys Phe Leu Ala Tyr Ala
210                 215                 220

Glu Phe Asn Asp Thr Asp Ile Pro Val Ile Ala Tyr Ser Tyr Tyr Gly
225                 230                 235                 240

Asp Glu Gln Tyr Pro Arg Thr Ile Asn Ile Pro Tyr Pro Lys Ala Gly
                245                 250                 255

Ala Lys Asn Pro Val Val Arg Ile Phe Ile Asp Thr Thr Tyr Pro
            260                 265                 270

Ala Tyr Val Gly Pro Gln Glu Val Pro Val Pro Ala Met Ile Ala Ser
        275                 280                 285

Ser Asp Tyr Tyr Phe Ser Trp Leu Thr Trp Val Thr Asp Glu Arg Val
    290                 295                 300

Cys Leu Gln Trp Leu Lys Arg Val Gln Asn Val Ser Val Leu Ser Ile
305                 310                 315                 320

Cys Asp Phe Arg Glu Asp Trp Gln Thr Trp Asp Cys Pro Lys Thr Gln
                325                 330                 335

Glu His Ile Glu Glu Ser Arg Thr Gly Trp Ala Gly Gly Phe Val
            340                 345                 350

Ser Thr Pro Val Phe Ser Tyr Asp Ala Ile Ser Tyr Lys Ile Phe
        355                 360                 365

Ser Asp Lys Asp Gly Tyr Lys His Ile His Tyr Ile Lys Asp Thr Val
    370                 375                 380

Glu Asn Ala Ile Gln Ile Thr Ser Gly Lys Trp Glu Ala Ile Asn Ile
385                 390                 395                 400

Phe Arg Val Thr Gln Asp Ser Leu Phe Tyr Ser Ser Asn Glu Phe Glu
```

```
            405                 410                 415
Glu Tyr Pro Gly Arg Arg Asn Ile Tyr Arg Ile Ser Ile Gly Ser Tyr
            420                 425                 430

Pro Pro Ser Lys Lys Cys Val Thr Cys His Leu Arg Lys Glu Arg Cys
            435                 440                 445

Gln Tyr Tyr Thr Ala Ser Phe Ser Asp Tyr Ala Lys Tyr Tyr Ala Leu
            450                 455                 460

Val Cys Tyr Gly Pro Gly Ile Pro Ile Ser Thr Leu His Asp Gly Arg
465                 470                 475                 480

Thr Asp Gln Glu Ile Lys Ile Leu Glu Glu Asn Lys Glu Leu Glu Asn
                485                 490                 495

Ala Leu Lys Asn Ile Gln Leu Pro Lys Glu Glu Ile Lys Lys Leu Glu
                500                 505                 510

Val Asp Glu Ile Thr Leu Trp Tyr Lys Met Ile Leu Pro Pro Gln Phe
                515                 520                 525

Asp Arg Ser Lys Lys Tyr Pro Leu Leu Ile Gln Val Tyr Gly Gly Pro
                530                 535                 540

Cys Ser Gln Ser Val Arg Ser Val Phe Ala Val Asn Trp Ile Ser Tyr
545                 550                 555                 560

Leu Ala Ser Lys Glu Gly Met Val Ile Ala Leu Val Asp Gly Arg Gly
                565                 570                 575

Thr Ala Phe Gln Gly Asp Lys Leu Leu Tyr Ala Val Tyr Arg Lys Leu
                580                 585                 590

Gly Val Tyr Glu Val Glu Asp Gln Ile Thr Ala Val Arg Lys Phe Ile
                595                 600                 605

Glu Met Gly Phe Ile Asp Glu Lys Arg Ile Ala Ile Trp Gly Trp Ser
                610                 615                 620

Tyr Gly Gly Tyr Val Ser Ser Leu Ala Leu Ala Ser Gly Thr Gly Leu
625                 630                 635                 640

Phe Lys Cys Gly Ile Ala Val Ala Pro Val Ser Ser Trp Glu Tyr Tyr
                645                 650                 655

Ala Ser Val Tyr Thr Glu Arg Phe Met Gly Leu Pro Thr Lys Asp Asp
                660                 665                 670

Asn Leu Glu His Tyr Lys Asn Ser Thr Val Met Ala Arg Ala Glu Tyr
                675                 680                 685

Phe Arg Asn Val Asp Tyr Leu Leu Ile His Gly Thr Ala Asp Asp Asn
                690                 695                 700

Val His Phe Gln Asn Ser Ala Gln Ile Ala Lys Ala Leu Val Asn Ala
705                 710                 715                 720

Gln Val Asp Phe Gln Ala Met Trp Tyr Ser Asp Gln Asn His Gly Leu
                725                 730                 735

Ser Gly Leu Ser Thr Asn His Leu Tyr Thr His Met Thr His Phe Leu
                740                 745                 750

Lys Gln Cys Phe Ser Leu Ser Asp
                755                 760
```

<210> SEQ ID NO 16
<211> LENGTH: 761
<212> TYPE: PRT
<213> ORGANISM: Mus musculus

<400> SEQUENCE: 16

```
Met Lys Thr Trp Leu Lys Thr Val Phe Gly Val Thr Thr Leu Ala Ala
1               5                   10                  15

Leu Ala Leu Val Val Ile Cys Ile Val Leu Arg Pro Ser Arg Val Tyr
            20                  25                  30

Lys Pro Glu Gly Asn Thr Lys Arg Ala Leu Thr Leu Lys Asp Ile Leu
        35                  40                  45

Asn Gly Thr Phe Ser Tyr Lys Thr Tyr Phe Pro Asn Trp Ile Ser Glu
50                  55                  60

Gln Glu Tyr Leu His Gln Ser Glu Asp Asp Asn Ile Val Phe Tyr Asn
65                  70                  75                  80

Ile Glu Thr Arg Glu Ser Tyr Ile Ile Leu Ser Asn Ser Thr Met Lys
                85                  90                  95

Ser Val Asn Ala Thr Asp Tyr Gly Leu Ser Pro Asp Arg Gln Phe Val
            100                 105                 110

Tyr Leu Glu Ser Asp Tyr Ser Lys Leu Trp Arg Tyr Ser Tyr Thr Ala
        115                 120                 125

Thr Tyr Tyr Ile Tyr Asp Leu Gln Asn Gly Glu Phe Val Arg Gly Tyr
130                 135                 140

Glu Leu Pro Arg Pro Ile Gln Tyr Leu Cys Trp Ser Pro Val Gly Ser
145                 150                 155                 160

Lys Leu Ala Tyr Val Tyr Gln Asn Asn Ile Tyr Leu Lys Gln Arg Pro
                165                 170                 175

Gly Asp Pro Pro Phe Gln Ile Thr Tyr Thr Gly Arg Glu Asn Arg Ile
            180                 185                 190

Phe Asn Gly Ile Pro Asp Trp Val Tyr Glu Glu Met Leu Ala Thr
        195                 200                 205

Lys Tyr Ala Leu Trp Trp Ser Pro Asp Gly Lys Phe Leu Ala Tyr Val
210                 215                 220

Glu Phe Asn Asp Ser Asp Ile Pro Ile Ile Ala Tyr Ser Tyr Tyr Gly
225                 230                 235                 240

Asp Gly Gln Tyr Pro Arg Thr Ile Asn Ile Pro Tyr Pro Lys Ala Gly
                245                 250                 255

Ala Lys Asn Pro Val Val Arg Val Phe Ile Val Asp Thr Thr Tyr Pro
            260                 265                 270

His His Val Gly Pro Met Glu Val Pro Val Pro Glu Met Ile Ala Ser
        275                 280                 285

Ser Asp Tyr Tyr Phe Ser Trp Leu Thr Trp Val Ser Ser Glu Arg Val
290                 295                 300

Cys Leu Gln Trp Leu Lys Arg Val Gln Asn Val Ser Val Leu Ser Ile
305                 310                 315                 320

Cys Asp Phe Arg Glu Asp Trp His Ala Trp Glu Cys Pro Lys Asn Gln
                325                 330                 335

Glu His Val Glu Glu Ser Arg Thr Gly Trp Ala Gly Gly Phe Phe Val
            340                 345                 350

Ser Thr Pro Ala Phe Ser Gln Asp Ala Thr Ser Tyr Tyr Lys Ile Phe
        355                 360                 365

Ser Asp Lys Asp Gly Tyr Lys His Ile His Tyr Ile Lys Asp Thr Val
```

```
            370                 375                 380
Glu Asn Ala Ile Gln Ile Thr Ser Gly Lys Trp Glu Ala Ile Tyr Ile
385                 390                 395                 400

Phe Arg Val Thr Gln Asp Ser Leu Phe Tyr Ser Ser Asn Glu Phe Glu
                405                 410                 415

Gly Tyr Pro Gly Arg Arg Asn Ile Tyr Arg Ile Ser Ile Gly Asn Ser
            420                 425                 430

Pro Pro Ser Lys Lys Cys Val Thr Cys His Leu Arg Lys Glu Arg Cys
            435                 440                 445

Gln Tyr Tyr Thr Ala Ser Phe Ser Tyr Lys Ala Lys Tyr Tyr Ala Leu
        450                 455                 460

Val Cys Tyr Gly Pro Gly Leu Pro Ile Ser Thr Leu His Asp Gly Arg
465                 470                 475                 480

Thr Asp Gln Glu Ile Gln Val Leu Glu Glu Asn Lys Glu Leu Glu Asn
                485                 490                 495

Ser Leu Arg Asn Ile Gln Leu Pro Lys Val Glu Ile Lys Lys Leu Lys
            500                 505                 510

Asp Gly Gly Leu Thr Phe Trp Tyr Lys Met Ile Leu Pro Pro Gln Phe
            515                 520                 525

Asp Arg Ser Lys Lys Tyr Pro Leu Leu Ile Gln Val Tyr Gly Gly Pro
        530                 535                 540

Cys Ser Gln Ser Val Lys Ser Val Phe Ala Val Asn Trp Ile Thr Tyr
545                 550                 555                 560

Leu Ala Ser Lys Glu Gly Ile Val Ile Ala Leu Val Asp Gly Arg Gly
                565                 570                 575

Thr Ala Phe Gln Gly Asp Lys Phe Leu His Ala Val Tyr Arg Lys Leu
            580                 585                 590

Gly Val Tyr Glu Val Glu Asp Gln Leu Thr Ala Val Arg Lys Phe Ile
            595                 600                 605

Glu Met Gly Phe Ile Asp Glu Glu Arg Ile Ala Ile Trp Gly Trp Ser
        610                 615                 620

Tyr Gly Gly Tyr Val Ser Ser Leu Ala Leu Ala Ser Gly Thr Gly Leu
625                 630                 635                 640

Phe Lys Cys Gly Ile Ala Val Ala Pro Val Ser Ser Trp Glu Tyr Tyr
                645                 650                 655

Ala Ser Ile Tyr Ser Glu Arg Phe Met Gly Leu Pro Thr Lys Asp Asp
            660                 665                 670

Asn Leu Glu His Tyr Lys Asn Ser Thr Val Met Ala Arg Ala Glu Tyr
            675                 680                 685

Phe Arg Asn Val Asp Tyr Leu Leu Ile His Gly Thr Ala Asp Asp Asn
        690                 695                 700

Val His Phe Gln Asn Ser Ala Gln Ile Ala Lys Ala Leu Val Asn Ala
705                 710                 715                 720

Gln Val Asp Phe Gln Ala Met Trp Tyr Ser Asp Gln Asn His Gly Ile
                725                 730                 735

Ser Ser Gly Arg Ser Gln Asn His Leu Tyr Thr His Met Thr His Phe
            740                 745                 750

Leu Lys Gln Cys Phe Ser Leu Ser Asp
            755                 760
```